(12) United States Patent
Lamble et al.

(10) Patent No.: US 12,275,991 B2
(45) Date of Patent: Apr. 15, 2025

(54) NUCLEIC ACID DETECTION METHOD

(71) Applicant: Sense Biodetection Limited, Abingdon (GB)

(72) Inventors: Henry John Lamble, Abingdon (GB); David Lloyd, Abingdon (GB); Eryk Dunski, Abingdon (GB); Steven Watson, Abingdon (GB)

(73) Assignee: Sense Biodetection Limited, Abingdon (GB)

( * ) Notice: Subject to any disclaimer, the term of this patent is extended or adjusted under 35 U.S.C. 154(b) by 543 days.

(21) Appl. No.: 16/773,289

(22) Filed: Jan. 27, 2020

(65) Prior Publication Data
US 2021/0024998 A1 Jan. 28, 2021
US 2025/0075271 A9 Mar. 6, 2025

Related U.S. Application Data

(63) Continuation-in-part of application No. PCT/GB2019/052089, filed on Jul. 25, 2019.

(30) Foreign Application Priority Data

Jul. 25, 2018 (GB) .................................... 1812149

(51) Int. Cl.
*C12Q 1/6876* (2018.01)
*C12Q 1/6806* (2018.01)
(Continued)

(52) U.S. Cl.
CPC ......... *C12Q 1/6876* (2013.01); *C12Q 1/6806* (2013.01); *C12Q 1/6816* (2013.01);
(Continued)

(58) Field of Classification Search
CPC ............................ C12Q 1/683; C12Q 1/6834; C12Q 2521/301; C12Q 2525/113;
(Continued)

(56) References Cited

U.S. PATENT DOCUMENTS 5,200,313 A 4/1993 Carrico
5,455,166 A 10/1995 Walker
(Continued)

FOREIGN PATENT DOCUMENTS

CN 102428191 A 4/2012
CN 104685066 A 6/2015
(Continued)

OTHER PUBLICATIONS

Wang et al., "Amplified Voltammetric Detection of DNA Hybridization via Oxidation of Ferrocene Caps on Gold Nanoparticles/Streptavidin Conjugates," Analytical Chemistry, vol. 75, pp. 3941-3945. (Year: 2003).*
(Continued)

*Primary Examiner* — Young J Kim
(74) *Attorney, Agent, or Firm* — Choate, Hall & Stewart LLP

(57) ABSTRACT

The present invention relates to methods for the detection of nucleic acids of defined sequence and kits and devices for use in said methods. The methods employ restriction enzymes, polymerase and oligonucleotide primers to produce an amplification product in the presence of a target nucleic acid, which is contacted with oligonucleotide probes to produce a detector product.

27 Claims, 16 Drawing Sheets

Specification includes a Sequence Listing.

(51) Int. Cl.
*C12Q 1/6816* (2018.01)
*C12Q 1/683* (2018.01)
*G01N 33/543* (2006.01)

(52) U.S. Cl.
CPC ....... *C12Q 1/683* (2013.01); *G01N 33/54306* (2013.01); *C12Q 2600/178* (2013.01)

(58) Field of Classification Search
CPC ........ C12Q 2525/125; C12Q 2525/131; C12Q 2531/119; C12Q 2565/543; C12Q 2565/519; C12Q 2520/00; C12Q 2500/00; C12Q 2525/00; C12Q 2547/00; C12Q 1/6876; C12Q 1/6806; C12Q 1/6816; G01N 1/00; G01N 25/00; G01N 27/00
See application file for complete search history.

(56) References Cited

U.S. PATENT DOCUMENTS

| | | | |
|---|---|---|---|
| 5,712,124 | A | 1/1998 | Walker |
| 6,136,533 | A | 10/2000 | Bekkaoui et al. |
| 6,309,833 | B1 | 10/2001 | Edman et al. |
| 10,077,467 | B2 | 9/2018 | Shaffer et al. |
| 2006/0035231 | A1 | 2/2006 | Van Beuningen et al. |
| 2010/0279295 | A1 | 11/2010 | Roy et al. |
| 2016/0265070 | A1 | 9/2016 | Hudson et al. |
| 2017/0247689 | A1 | 8/2017 | Brown |
| 2018/0127815 | A1* | 5/2018 | Belousov ............ C12Q 1/6818 |
| 2021/0147830 | A1 | 5/2021 | Liss |
| 2021/0246487 | A1* | 8/2021 | Lamble ................ C12Q 1/6806 |

FOREIGN PATENT DOCUMENTS

| | | |
|---|---|---|
| EP | 0497272 A1 | 8/1992 |
| JP | 2005-537002 A | 12/2005 |
| WO | 00/60919 A2 | 10/2000 |
| WO | 2004/020667 A1 | 3/2004 |
| WO | 2009/012246 | 1/2009 |
| WO | 2014/164479 | 10/2014 |
| WO | 2015/195949 A2 | 12/2015 |
| WO | 2018/002649 | 1/2018 |

OTHER PUBLICATIONS

Product Description, Biotin-TEG, [retrieved on line, retrieved from https://www.metabion.com/learning-platform/modifications/attachment-moieties-purification/biotin-teg/#:~:text=Biotin%20can%20be%20used%20as,Biotin%20moiety%20and%20the%20oligonucleotide. retrieval date Apr. 3, 2023]. (Year: 2023).*

Walker et al. Strand displacement amplification—an isothermal, in vitro amplification technique. Nucleic Acids Research, vol. 20, No. 7, 1992, pp. 1691-1696.

Forster, et al., "A human gut bacterial genome and culture collection for improved metagenomic analyses," Nature Biotechnology, vol. 37, pp. 186-192, Feb. 2019.

Yan et al. Isothermal amplified detection of DNA and RNA. Molecular BioSystems, vol. 10, 2014, pp. 970-1003.

Wei Wu et al. A sensitive aptasensor for the detection of Vibrio parahaemolyticus. Sensors and Actuators B: Chemical, vol. 272, Jun. 5, 2018, pp. 550-558.

Toley et al. Isothermal strand displacement amplification (iSDA): a rapid and sensitive method of nucleic acid amplification for point-of-care diagnosis. Analyst, vol. 140, No. 22, Sep. 8, 2015, pp. 7540-7549.

Walker et al. Molecular Methods for Virus Detection. Academic Press, Chapter 15, 1995, pp. 329-349.

Edman, et al., "Pathogen Analysis and Genetic Predisposition Testing Using Microelectronic Arrays and Isothermal Amplification," Journal of Investigative Medicine, vol. 48, No. 2, pp. 93-101, Mar. 2000.

Nie, et al., "Evaluation of Alere I Influenza A&B for Rapid Detection of Influenza Viruses A and B," Journal of Clinical Microbiology, vol. 52, No. 9, pp. 3339-3344, Sep. 2014.

Spargo, et al., "SDA Target Amplification," Springer Second Edition, vol. 2, pp. 356-366, Jan. 2000.

"Animal", Wikipedia.com, pp. 1-19, accessed Jan. 23, 2018. (Year: 2018).

"Complete genome sequence of a 2019 novel coronavirus (SARS-CoV-2) Strain isolated in Nepal", Microbiology Resource Announcements, American Society for Microbiology, pp. 1-3, access Apr. 23, 2020. (Year: 2020).

"Human Genome", Wikipedia.com, pp. 1-16, accessed Aug. 4, 2021. (Year: 2021).

"Influenza Hemagglutinin (HA) subtypes and Flu Virus Strains" https://www.sinobiological.com/research/virus/influenza-hemagglutinin-subtypes, accessed May 5, 2023 (Year: 2023).

Kessler, C. (ed.), Nonradioactive analysis of biomolecules—2nd ed., 2000, Springer-Verlag Berlin Heidelberg, Chapter 29, pp. 356-366, DOI 10.1007/978-3-642-57206-7.

* cited by examiner

```
                       SEQUENCE LISTING

<160> NUMBER OF SEQ ID NOS: 11

<210> SEQ ID NO 1
<211> LENGTH: 34
<212> TYPE: DNA
<213> ORGANISM: Artificial Sequence
<220> FEATURE:
<223> OTHER INFORMATION: Oligonucleotide

<400> SEQUENCE: 1
tttttttttt agagagagag agagagagag agag                                   34

<210> SEQ ID NO 2
<211> LENGTH: 47
<212> TYPE: DNA
<213> ORGANISM: Artificial Sequence
<220> FEATURE:
<223> OTHER INFORMATION: Oligonucleotide

<400> SEQUENCE: 2
tttttttttt taataataat aataataata ataataataa taataat                     47

<210> SEQ ID NO 3
<211> LENGTH: 45
<212> TYPE: DNA
<213> ORGANISM: Artificial Sequence
<220> FEATURE:
<223> OTHER INFORMATION: Oligonucleotide

<400> SEQUENCE: 3
ttttttttta ccaccaccac caccaccacc accaccacca ccacc                       45

<210> SEQ ID NO 4
<211> LENGTH: 42
<212> TYPE: DNA
<213> ORGANISM: Artificial Sequence
<220> FEATURE:
<223> OTHER INFORMATION: Oligonucleotide

<400> SEQUENCE: 4
tttttttttt aactaactaa ctaactaact aactaactaa ct                          42

<210> SEQ ID NO 5
<211> LENGTH: 42
<212> TYPE: DNA
<213> ORGANISM: Artificial Sequence
<220> FEATURE:
```

<223> OTHER INFORMATION: Oligonucleotide

<400> SEQUENCE: 5
tttttttttt gagtgagtga gtgagtgagt gagtgagtga gt                42

<210> SEQ ID NO 6
<211> LENGTH: 44
<212> TYPE: DNA
<213> ORGANISM: Artificial Sequence
<220> FEATURE:
<223> OTHER INFORMATION: Oligonucleotide

<400> SEQUENCE: 6
tttttttttt tgtcgactcg gagtcgactc ggagtcgact cgga             44

<210> SEQ ID NO 7
<211> LENGTH: 44
<212> TYPE: DNA
<213> ORGANISM: Artificial Sequence
<220> FEATURE:
<223> OTHER INFORMATION: Oligonucleotide

<400> SEQUENCE: 7
tttttttttt tggatatccc gtggatatcc cgtggatatc ccgt             44

<210> SEQ ID NO 8
<211> LENGTH: 41
<212> TYPE: DNA
<213> ORGANISM: Artificial Sequence
<220> FEATURE:
<223> OTHER INFORMATION: Oligonucleotide

<400> SEQUENCE: 8
tttttttttt tgccatcac gtgccatcac gtgccatcac g                 41

<210> SEQ ID NO 9
<211> LENGTH: 47
<212> TYPE: DNA
<213> ORGANISM: Artificial Sequence
<220> FEATURE:
<223> OTHER INFORMATION: Oligonucleotide

<400> SEQUENCE: 9
tttttttttt tcagttgcgt gaacagttgc gtgaacagtt gcgtgaa          47

<210> SEQ ID NO 10
<211> LENGTH: 44
<212> TYPE: DNA
<213> ORGANISM: Artificial Sequence
<220> FEATURE:
<223> OTHER INFORMATION: Oligonucleotide

<400> SEQUENCE: 10
tttttttttt tcgctgtatt cacgctgtat tcacgctgta ttca             44

<210> SEQ ID NO 11
<211> LENGTH: 53
<212> TYPE: DNA
<213> ORGANISM: Artificial Sequence
<220> FEATURE:
<223> OTHER INFORMATION: Oligonucleotide

<400> SEQUENCE: 11
tttttttttt ttaacagtat ggaaataaca gtatggaaat aacagtatgg aaa   53

NUCLEIC ACID DETECTION METHOD

CROSS REFERENCE TO RELATED APPLICATIONS

This application is a continuation in part of International Application No. PCT/GB2019/052089, filed on Jul. 25, 2019, which claims the benefit of U.K. Patent Application No. 1812149.1, filed Jul. 25, 2018, each of which is incorporated herein by reference in its entirety.

BACKGROUND

Technical Field

The present invention is directed to methods for the detection of nucleic acids of defined sequence and kits and devices for use in said methods.

Related Art

Methods of nucleic acid sequence amplification based on polymerases are widely used in the field of molecular diagnostics. The most established method, polymerase chain reaction (PCR), typically involves two primers for each target sequence and uses temperature cycling to achieve primer annealing, extension by DNA polymerase and denaturation of newly synthesised DNA in a cyclical exponential amplification process. The requirement for temperature cycling necessitates complex equipment which limits the use of PCR-based methods in certain applications.

Strand Displacement Amplification (SDA) (EP0497272; U.S. Pat. No. 5,455,166; U.S. Pat. No. 5,712,124) was developed as an isothermal alternative to PCR that does not require temperature cycling to achieve the annealing and denaturation of double stranded DNA during polymerase amplification, and instead uses restriction enzymes combined with a strand-displacement polymerase to separate the two DNA strands.

In SDA, a restriction enzyme site at the 5' end of each primer is introduced into the amplification product in the presence of one or more alpha thiol nucleotide, and a restriction enzyme is used to nick the restriction sites by virtue of its ability to cleave only the unmodified strand of a hemiphosphorothioate form of its recognition site. A strand displacement polymerase extends the 3'-end of each nick and displaces the downstream DNA strand. Exponential amplification results from coupling sense and antisense reactions in which strands displaced from a sense reaction serve as target for an antisense reaction and vice versa. SDA typically takes over 1 hour to perform, which has greatly limited its potential for exploitation in the field of clinical diagnostics. Furthermore, the requirement for separate processes for specific detection of the product following amplification and to initiate the reaction add significant complexity to the method.

Maples et al. (WO2009/012246) subsequently performed SDA using nicking enzymes, a sub-class of restriction enzymes that are only capable of cleaving one of the two strands of DNA following binding to their specific double stranded recognition sequence. They referred to the method as Nicking and Extension Amplification Reaction (NEAR). NEAR, which employs nicking enzymes instead of restriction enzymes, has subsequently also been employed by others, who have attempted to improve the method using software optimised primers (WO2014/164479) and through a warm start or controlled reduction in temperature (WO2018/002649). However, only a very small number of nicking enzymes are available and thus it is more challenging to find an enzyme with the desired properties for a particular application.

A crucial disadvantage of SDA using either restriction enzymes or nicking enzymes (NEAR) is that it produces a double stranded nucleic acid product and thus does not provide an intrinsic process for efficient detection of the amplification signal. This has significantly limited its utility in, for example, low-cost diagnostic devices. The double stranded nature of the amplified product produced presents a challenge for coupling the amplification method to signal detection since it is not possible to perform hybridisation-based detection without first separating the two strands. Therefore more complex detection methods are required, such as molecular beacons and fluorophore/quencher probes, which can complicate assay protocols by requiring a separate process step and significantly reduces the potential to develop multiplex assays.

There is an important requirement for enhanced amplification methods for rapid, sensitive and specific nucleic acid sequence detection to overcome the limitations of SDA. The present invention relates to a method of target nucleic acid sequence amplification and detection which, in addition to a pair of primers with 5' restriction sites, utilises additional oligonucleotide probes to produce a detector species that enables efficient signal detection.

SUMMARY

The invention provides a method for detecting the presence of a single stranded target nucleic acid of defined sequence in a sample comprising:
a) contacting the sample with:
  i. a first oligonucleotide primer and a second oligonucleotide primer wherein said first primer comprises in the 5' to 3' direction one strand of a restriction enzyme recognition sequence and cleavage site and a region that is capable of hybridising to a first hybridisation sequence in the target nucleic acid, and said second primer comprises in the 5' to 3' direction one strand of a restriction enzyme recognition sequence and cleavage site and a region that is capable of hybridising to the reverse complement of a second hybridisation sequence upstream of the first hybridisation sequence in the target nucleic acid;
  ii. a strand displacement DNA polymerase;
  iii. dNTPs;
  iv. one or more modified dNTP;
  v. a first restriction enzyme that is not a nicking enzyme but is capable of recognising the recognition sequence of the first primer and cleaving only the first primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP; and
  vi. a second restriction enzyme that is not a nicking enzyme but is capable of recognising the recognition sequence of the second primer and cleaving only the second primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP;

to produce, without temperature cycling, in the presence of said target nucleic acid, amplification product;

b) contacting the amplification product of step a) with:
   i. a first oligonucleotide probe which is capable of hybridising to a first single stranded detection sequence in at least one species within the amplification product and which is attached to a moiety that permits its detection; and
   ii. a second oligonucleotide probe which is capable of hybridising to a second single stranded detection sequence upstream or downstream of the first single stranded detection sequence in said at least one species within the amplification product and which is attached to a solid material or to a moiety that permits its attachment to a solid material;

where hybridisation of the first and second probes to said at least one species within the amplification product produces a detector species; and c) detecting the presence of the detector species produced in step b) wherein the presence of the detector species indicates the presence of the target nucleic acid in said sample.

An embodiment of the method is illustrated in FIG. 1.

In various embodiments, in the presence of target nucleic acid, the method rapidly produces many copies of the detector species which is ideally suited to sensitive detection.

The present invention in various aspects is advantageous over known methods because it encompasses rapid amplification without temperature cycling in addition to providing an intrinsic process for efficient detection of the amplified product.

The method of the invention overcomes a major disadvantage of SDA, including SDA with nicking enzymes (NEAR), which is that SDA does not provide an intrinsic process for efficient detection of the amplification signal due to the double stranded nature of the amplification product. The present method overcomes this limitation by utilising two additional oligonucleotide probes which hybridise to at least one species in the amplification product to facilitate its rapid and specific detection. The use of these two additional oligonucleotide probes, the first of which is attached to a moiety that permits its detection and the second of which is attached to a solid material or a moiety that permits it attachment to a solid material, provide a number of further advantages to the present invention over known methods such as SDA. For example, in embodiments of the invention wherein one of the oligonucleotide probes is blocked at the 3' end from extension by the DNA polymerase, is not capable of being cleaved by the restriction enzyme(s) and is contacted with the sample simultaneously to the performance of step a), surprisingly no significant detrimental inhibition of the amplification is observed and a pre-detector species containing a single stranded region is produced efficiently. This aspect of the invention is counter-intuitive as it may be assumed that such a blocked probe would lead to asymmetric amplification that is biased to the opposite amplification product strand to that comprised in the pre-detector species. In fact, said pre-detector species is efficiently produced and ideally suited to efficient detection because the exposed single stranded region is readily available for hybridisation of the other oligonucleotide probe.

The intrinsic sample detection approach of the present method contrasts fundamentally with prior attempts to overcome this important limitation of SDA which involved performing "asymmetric" amplification, for example, by using an unequal primer ratio with a goal of producing an excess of one amplicon strand over the other. The present method does not require asymmetric amplification nor does it have any requirement to produce an excess of one strand of the amplicon over the other and instead it is focussed on production of the detector species following hybridisation of the first and second oligonucleotide probes. The intrinsic sample detection approach of the present method involving production of a detector species is ideally suited to its coupling with, amongst other detection methods, nucleic acid lateral flow, providing a simple, rapid and low-cost means of performing detection in step c), for example, by printing the second oligonucleotide probe on the lateral flow strip. When coupled to nucleic acid lateral flow the method also permits efficient multiplexing based upon differential hybridisation of multiple second oligonucleotide probes attached at discrete locations on the lateral flow strip, each with a different sequence designed for a different target nucleic acid sequence in the sample. In further embodiments of the method, the efficiency of the lateral flow detection is enhanced by the use of a single stranded oligonucleotide as the moiety within the second oligonucleotide probe that permits its attachment to a solid material, and the reverse complementary sequence to said moiety is printed on the strip. The latter approach also permits the lateral flow strip to be optimised and manufactured as a single "universal" detection system across multiple target applications because the sequences attached to the lateral flow strip can be defined and do not need to correspond to the sequence of the target nucleic acid(s). The integral requirement for two additional oligonucleotide probes in the method of the invention thus provides many advantages over SDA, including SDA with nicking enzymes (NEAR).

Since the present invention requires the use of restriction enzyme(s) that are not nicking enzymes and one or more modified dNTP, it is fundamentally different to SDA performed using nicking enzymes (NEAR) and has a number of further advantages over such nicking enzyme dependent methods. For example, a much greater number of restriction enzymes that are not nicking enzymes are available than nicking enzymes, which means that the restriction enzyme(s) for use in the method of the invention can be selected from a large number of potential enzymes to identify those with superior properties for a given application, e.g. reaction temperature, buffer compatibility, stability and reaction rate (sensitivity). Due to this key advantage of the present method, we have been able to select restriction enzymes with a lower temperature optimum and a faster rate than would be possible to achieve with nicking enzymes. Such restriction enzymes are much better suited to exploitation in a low-cost diagnostic device. Furthermore the requirement to use one or more modified dNTP is an integral feature of the present invention which offers important advantages in addition to providing for the restriction enzymes to cleave only one strand of their restriction sites. For example, certain modified dNTPs, such as alpha thiol dNTPs, lead to a reduction in the melting temperature (Tm) of the DNA into which they are incorporated which means the oligonucleotide primers and probes in the method have a greater affinity for hybridisation to the species within the amplification product than any competing complementary strand containing modified dNTP produced during the amplification. Furthermore, the reduction in Tm of the amplification product as a result of modified dNTP base insertion facilitates the separation of double stranded DNA species and thus enhances the rate of amplification, reduces the temperature optimum and improves the sensitivity. Alternatively, other modified dNTPs can increase the Tm of the DNA into which they are incorporated presenting further opportunities to tailor the performance of the method for a given application.

Together the numerous advantages of the present invention over SDA, using either restriction enzymes or nicking enzymes (NEAR), provide for the utility of the method in low-cost, single-use diagnostic devices, by virtue of the improved rate of amplification and simple visualisation of the amplification signal that are not possible with known methods.

Various embodiments of the above mentioned aspects of the invention, and further aspects, are described in more detail below.

DETAILED DESCRIPTION

Figure 1:
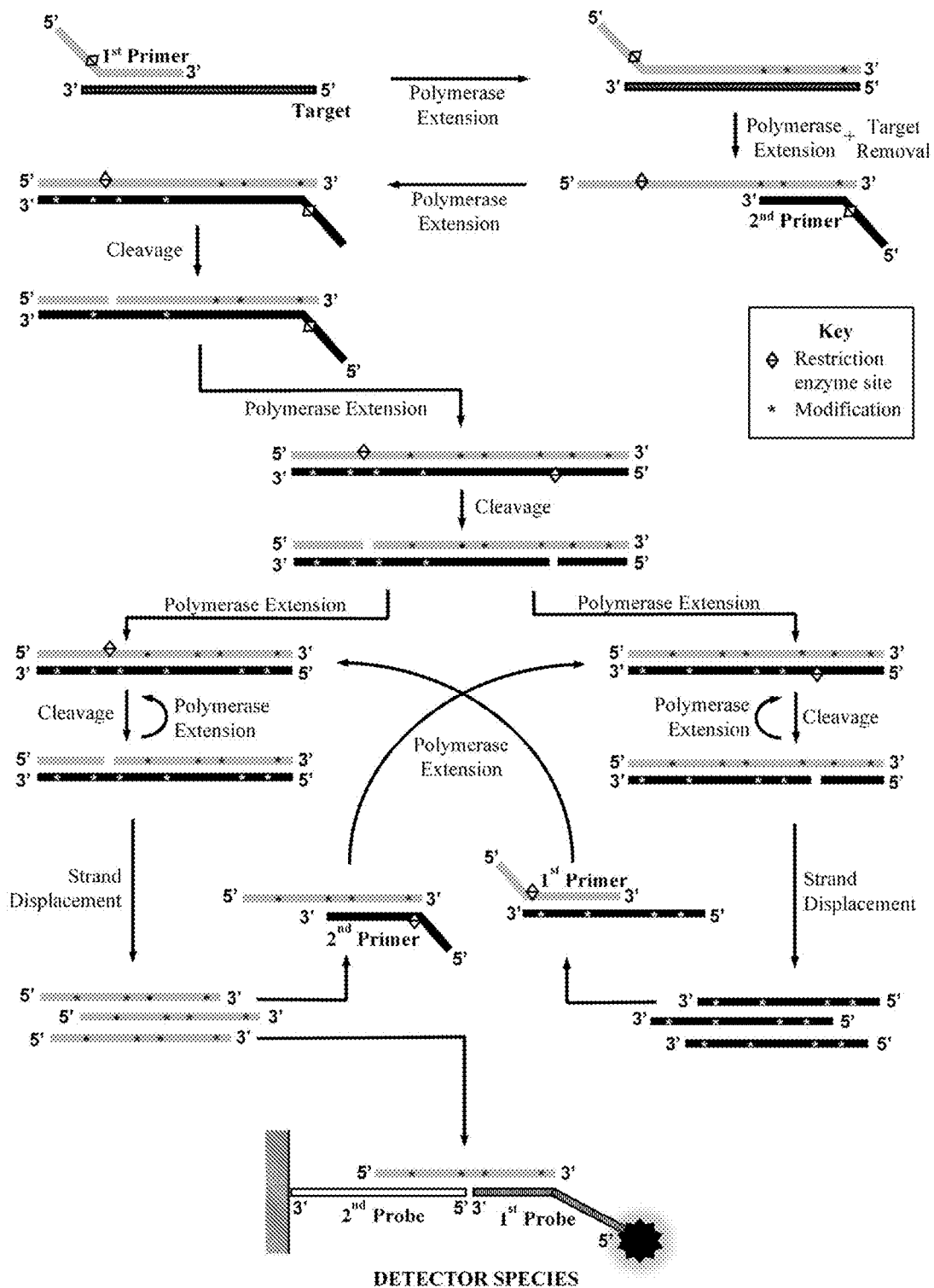
FIG. 1. Schematic representation of the method according to one aspect of the invention.

The present invention provides a method for detecting the presence of a single stranded target nucleic acid of defined sequence in a sample. The target nucleic acid may be single stranded DNA, including single stranded DNA derived from double stranded DNA following disassociation of the two strands in the sample such as by heat denaturation or through strand displacement activity of a polymerase, or derived from RNA e.g. by the action of reverse transcriptase, or derived from double stranded DNA e.g. by use of a nuclease, such as a restriction endonuclease or exonuclease III, or derived from a RNA/DNA hybrid e.g. through an enzyme such as Ribonuclease H. The target nucleic acid may be single stranded DNA derived from DNA in the sample by a DNA polymerase, helicase or recombinase. Single stranded sites within double stranded DNA may be exposed sufficiently for hybridisation and extension of the first oligonucleotide primer to initiate the method, for example by "strand invasion" wherein transient opening of one or more DNA base pairs within the double stranded DNA occurs sufficiently to permit hybridisation and extension of the 3' hydroxyl of the first oligonucleotide primer, or by spontaneous opening of DNA base pairs, transient conversion to Hoogsteen pairs or productive nicking of DNA by restriction enzyme or thermochemical approaches. The target nucleic acid may be single stranded RNA, including single stranded RNA derived from double stranded RNA in the sample following disassociation of the two strands such as by heat denaturation or single stranded RNA derived from double stranded DNA e.g. by transcription.

The method involves in step a) contacting the sample with: (i) a first oligonucleotide primer and a second oligonucleotide primer wherein said first primer comprises in the 5' to 3' direction one strand of a restriction enzyme recognition sequence and cleavage site and a region that is capable of hybridising to a first hybridisation sequence in the target nucleic acid, and said second primer comprises in the 5' to 3' direction one strand of a restriction enzyme recognition sequence and cleavage site and a region that is capable of hybridising to the reverse complement of a second hybridisation sequence upstream of the first hybridisation sequence in the target nucleic acid; (ii) a strand displacement DNA polymerase; (iii) dNTPs; (iv) one or more modified dNTP; (v) a first restriction enzyme that is not a nicking enzyme but is capable of recognising the recognition sequence of the first primer and cleaving only the first primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP; and (vi) a second restriction enzyme that is not a nicking enzyme but is capable of recognising the recognition sequence of the second primer and cleaving only the second primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP.

When the target nucleic acid to be detected in the sample is double stranded either strand may be deemed the single stranded target nucleic acid of the method since one of the two oligonucleotide primers is capable of hybridisation to one strand and the other oligonucleotide primer is capable of hybridisation to the other strand. Typically, the oligonucleotide primers used in the method are DNA primers which form with the DNA or RNA target a double stranded DNA or a hybrid duplex comprising strands of both RNA and DNA. However, primers comprising other nucleic acids, such as non-natural bases and/or alternative backbone structures, may also be used.

In the presence of the target nucleic acid the first oligonucleotide primer hybridises to the first hybridisation sequence in the target nucleic acid. Following said hybridisation, the 3' hydroxyl group of the first primer is extended by the strand displacement DNA polymerase or, optionally, in the case of an RNA target nucleic acid a reverse transcriptase (e.g. M-MuLV), to produce a double stranded species containing the extended first primer and the target nucleic acid (see FIG. 1). The strand displacement DNA polymerase or, when present, the reverse transcriptase use the dNTPs and the one or more modified dNTP in said extension. The one strand of a restriction enzyme recognition sequence and cleavage site at the 5' end of the first primer does not typically hybridise as the reverse complementary sequence thereto is generally not present in the target nucleic acid sequence. Thus the first primer is generally used to introduce said one strand of a restriction enzyme recognition sequence and cleavage site into subsequent amplification product species. Following extension of the first primer, "target removal" occurs. Target removal makes accessible the extended first primer species for hybridisation of the second oligonucleotide primer to the reverse complement of the second hybridisation sequence. When the target nucleic acid is RNA, target removal may be accomplished, for example, by RNase H degradation of the RNA, accomplished through the RNase H activity of the reverse transcriptase if present or through separate addition of this enzyme. Alternatively, when the target nucleic acid is single stranded DNA, including a single-stranded region within double stranded DNA, it may be accomplished by strand displacement using an additional upstream primer or bump primer. Alternatively, such target removal may occur following spontaneous disassociation, particularly if only a short extension product has been produced from a given target nucleic acid molecule, or it may occur through strand invasion wherein transient opening of one or more DNA base pairs within the double stranded extended first primer species occurs sufficiently to permit hybridisation and extension of the 3' hydroxyl of the second oligonucleotide primer with strand displacement.

Following hybridisation of the second oligonucleotide primer to the reverse complement of the second hybridisation sequence, the strand displacement DNA polymerase extends the 3' hydroxyl of said primer using the dNTPs and the one or more modified dNTP. The double stranded restriction recognition sequence and cleavage site for the first restriction enzyme is formed with one or more modified dNTP base(s) incorporated into the reverse complementary strand acting to block the cleavage of said strand by said first restriction enzyme. The first restriction enzyme recognises its recognition sequence and cleaves only the first primer strand of the cleavage site, creating a 3' hydroxyl that is extended by the strand displacement DNA polymerase using the dNTPs and the one or more modified dNTP and displacing the first primer strand. The double stranded restriction recognition sequence and cleavage site for the second restriction enzyme is formed with one or more modified dNTP base(s) incorporated into the reverse complementary strand acting to block the cleavage of said strand by said second restriction enzyme. A double stranded species is thus produced in which the two primer sequences are juxtaposed and the partially blocked restriction site of the first restriction enzyme and second restriction enzyme are present. The cleavage by the first restriction enzyme of the first primer strand and by the second restriction enzyme of the second primer strand then occur, and two double stranded species are produced, one comprising the first primer sequence and the other comprising a second primer sequence. The sequential cleavage and displacement of the first primer strand and the second primer strand then occur in a cyclical amplification process wherein the displaced first primer strand acts as a target for the second primer and the displaced second primer strand acts as a target for the first primer.

In the presence of target nucleic acid, amplification product is produced without any requirement for temperature cycling.

An integral aspect of the present invention is that rather than direct detection of the amplification product of step a), a detector species is produced following the specific hybridisation of both a first and a second oligonucleotide probe to at least one species within the amplification product. The first oligonucleotide probe, which is attached to a moiety that permits its detection, hybridises to a first single stranded detection sequence in said at least one species. The second oligonucleotide probe, which is attached to a solid material or to a moiety that permits its attachment to a solid material, hybridises to a second single stranded detection sequence upstream or downstream of the first single stranded detection sequence in said at least one species.

It will be apparent to a skilled person, with reference to FIG. 1, that amplification product comprises a number of different species, such as species comprising single stranded detection sequences, consisting of the full or partial sequence or reverse complementary sequence of both the first primer and second primer, which sequences may be separated by target-derived sequence in the event that the primer binding first and second hybridisation sequences in the target nucleic acid are separated by one or more bases. It will further be apparent that any of said species may be selected to hybridise to the first and second oligonucleotide probe to form the detector species.

The detector species produced in step b) is detected in step c), wherein the presence of the detector species indicates the presence of the target nucleic acid in the sample.

By utilising two oligonucleotide probes, one for detection and one for attachment to a solid material, the method of the invention provides for rapid and efficient signal detection, which overcomes the requirement for more complex secondary detection methods and provides for efficient visualisation of the signal produced in the presence of target, such as by nucleic acid lateral flow.

The method of the invention may be performed wherein one of the first and second oligonucleotide probes is blocked at the 3' end from extension by the strand displacement DNA polymerase and is not capable of being cleaved by either the first or second restriction enzymes. Thus according to a further embodiment the invention provides a method for detecting the presence of a single stranded target nucleic acid of defined sequence in a sample comprising:
a) contacting the sample with:
i. a first oligonucleotide primer and a second oligonucleotide primer wherein said first primer comprises in the 5' to 3' direction one strand of a restriction enzyme recognition sequence and cleavage site and a region that is capable of hybridising to a first hybridisation sequence in the target nucleic acid, and said second primer comprises in the 5' to 3' direction one strand of a restriction enzyme recognition sequence and cleavage site and a region that is capable of hybridising to the reverse complement of a second hybridisation sequence upstream of the first hybridisation sequence in the target nucleic acid;
ii. a strand displacement DNA polymerase;
iii. dNTPs;
iv. one or more modified dNTP;
v. a first restriction enzyme that is not a nicking enzyme but is capable of recognising the recognition sequence of the first primer and cleaving only the first primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP; and
vi. a second restriction enzyme that is not a nicking enzyme but is capable of recognising the recognition sequence of the second primer and cleaving only the second primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP;
to produce, without temperature cycling, in the presence of said target nucleic acid, amplification product;
b) contacting the amplification product of step a) with:
i. a first oligonucleotide probe which is capable of hybridising to a first single stranded detection sequence in at least one species within the amplification product and which is attached to a moiety that permits its detection; and
ii. a second oligonucleotide probe which is capable of hybridising to a second single stranded detection sequence upstream or downstream of the first single stranded detection sequence in said at least one species within the amplification product and which is attached to a solid material or to a moiety that permits its attachment to a solid material;
wherein one of the first and second oligonucleotide probes is blocked at the 3' end from extension by the DNA polymerase and is not capable of being cleaved by either the first or second restriction enzymes, and where hybridisation of the first and second probes to said at least one species within the amplification product produces a detector species; and
c) detecting the presence of the detector species produced in step b) wherein the presence of the detector species indicates the presence of the target nucleic acid in said sample.

In an embodiment said one blocked oligonucleotide probe is rendered not capable of being cleaved by either the first or second restriction enzymes due to the presence of one or more sequence mismatch and/or one or more modifications such as a phosphorothioate linkage. In a further embodiment the one blocked oligonucleotide probe is contacted with the sample simultaneously to the performance of step a), i.e. during the performance of step a) such that it is present during the production of amplification product in the presence of the target nucleic acid. Thus according to a further embodiment the invention provides a method for detecting the presence of a single stranded target nucleic acid of defined sequence in a sample comprising:
a) contacting the sample with:
i. a first oligonucleotide primer and a second oligonucleotide primer wherein said first primer comprises in the 5' to 3' direction one strand of a restriction enzyme recognition sequence and cleavage site and a region that is capable of hybridising to a first hybridisation sequence in the target nucleic acid, and said second primer comprises in the 5' to 3' direction one strand of a restriction enzyme recognition sequence and cleavage site and a region that is capable of hybridising to the reverse complement of a second hybridisation sequence upstream of the first hybridisation sequence in the target nucleic acid;
ii. a strand displacement DNA polymerase;
iii. dNTPs;
iv. one or more modified dNTP;
v. a first restriction enzyme that is not a nicking enzyme but is capable of recognising the recognition sequence of the first primer and cleaving only the first primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP; and
vi. a second restriction enzyme that is not a nicking enzyme but is capable of recognising the recognition sequence of the second primer and cleaving only the second primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP;
to produce, without temperature cycling, in the presence of said target nucleic acid, amplification product;
b) contacting the amplification product of step a) with:
i. a first oligonucleotide probe which is capable of hybridising to a first single stranded detection sequence in at least one species within the amplification product and which is attached to a moiety that permits its detection; and
ii. a second oligonucleotide probe which is capable of hybridising to a second single stranded detection sequence upstream or downstream of the first single stranded detection sequence in said at least one species within the amplification product and which is attached to a solid material or to a moiety that permits its attachment to a solid material;
wherein one of the first and second oligonucleotide probes is blocked at the 3' end from extension by the DNA polymerase, is not capable of being cleaved by either the first or second restriction enzymes and is contacted with the sample simultaneously to the performance of step a), and where hybridisation of the first and second probes to said at least one species within the amplification product produces a detector species; and c) detecting the presence of the detector species produced in step b) wherein the presence of the detector species indicates the presence of the target nucleic acid in said sample.

Figure 2:
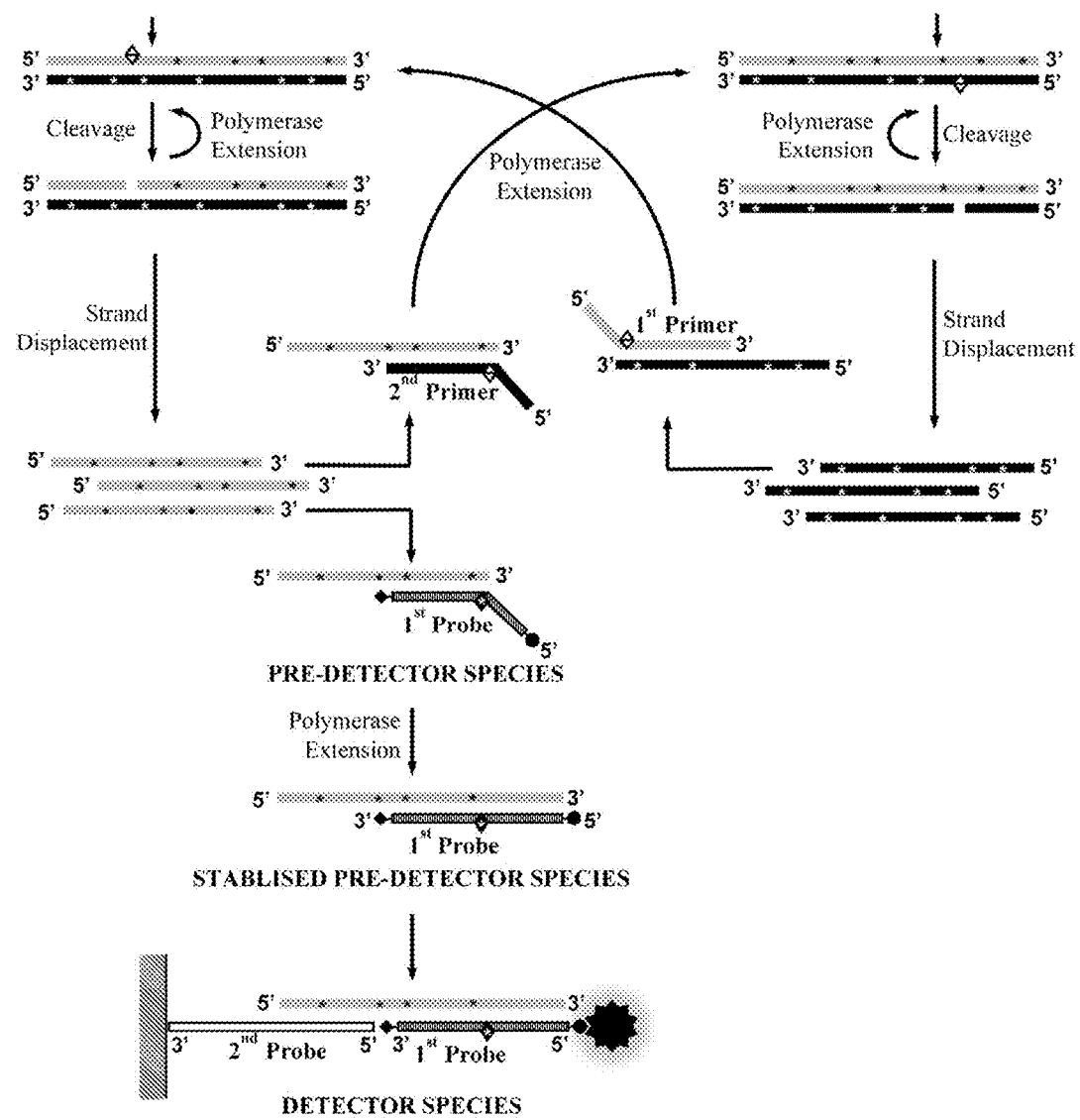
FIG. 2. Schematic representation of the method wherein the first oligonucleotide probe is blocked at the 3' end from extension by the DNA polymerase and is not capable of being cleaved by either the first or second restriction enzyme and is contacted with the sample in step a).
Figure 3:
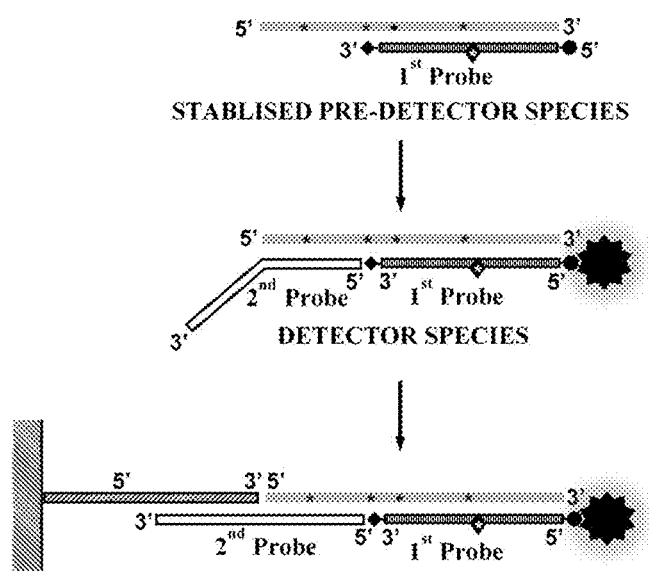
FIG. 3. Schematic representation of steps b) and c) of the method wherein the moiety that permits the attachment of the second oligonucleotide probe to a solid material is a single stranded oligonucleotide.

For example, in the embodiment illustrated in FIG. 2, the first oligonucleotide probe is blocked and hybridises to the first single stranded detection sequence in at least one species within the amplification product to form a pre-detector species containing a single stranded region. Said at least one species may be extended by the strand displacement DNA polymerase extending its 3' hydroxyl group and thus further stabilising said pre-detector species. Thus, in said embodiment the blocked oligonucleotide probe comprises an additional region such that the 3' end of the species within the amplification product to which the blocked oligonucleotide probe hybridises can be extended by the strand displacement DNA polymerase. A "Stabilised Pre-detector Species" is produced as displayed in FIG. 2. The skilled person will appreciate that this additional pre-detector species stabilisation region in the blocked oligonucleotide probe will be upstream of the region that hybridises to either the first or second single stranded detection sequence in the at least one species within the amplification product In embodiments using a blocked oligonucleotide probe the hybridisation sequence of the blocked oligonucleotide probe and the relevant concentrations of the primers may be optimised such that a certain proportion of the relevant species produced in the amplification product hybridises to the blocked oligonucleotide probe in each cycle and the remaining copies of such species remain available to participate in the cyclical amplification process. The oligonucleotide probe is blocked from extension, for example, by use of a 3' phosphate modification and, in this embodiment, is also attached to a moiety that permits its detection, such as a 5' biotin modification. Alternatively a single 3' modification may be used to block extension and as a moiety that permits its detection. Various other modifications are available to block the 3' end of oligonucleotides such as a C-3 spacer; alternatively mismatch base(s) may be employed. Said pre-detector species is ideally suited to efficient detection because the exposed single stranded region remains readily available for hybridisation to the second oligonucleotide probe. The second oligonucleotide probe may be attached to the nitrocellulose surface of a nucleic acid lateral flow strip such that when the pre-detector species flows over it sequence specific hybridisation readily occurs and the detector species becomes located at a defined location on the strip. A dye which attaches to the detection moiety, such as a streptavidin attached carbon, gold or polystyrene particle, that may be present in the conjugate pad of the nucleic acid lateral flow strip or during the amplification reaction, provides a rapid colour-based visualisation of the presence of the detector species produced in the presence of the target nucleic acid.

In another embodiment it is the second oligonucleotide probe that is blocked at the 3' end from extension by the strand displacement DNA polymerase and is not capable of being cleaved by either the first or second restriction enzymes and is contacted with the sample simultaneously to the performance of step a). The second oligonucleotide probe may be attached to a solid material, such as the surface of an electrochemical probe, 96-well plate, beads or array surface, prior to being contacted with the sample, or may be attached to a moiety that permits its attachment to a solid material. A certain proportion of at least one species produced during the amplification hybridises to the second oligonucleotide probe following its production, instead of hybridising to the relevant reaction primer to participate further in the cyclical amplification process. Following hybridisation to the second oligonucleotide probe, said species are extended by the polymerase onto the oligonucleotide probe to produce the stabilised pre-detector species. The first oligonucleotide probe and detection moiety may also be contacted with the sample simultaneously to the performance of step a) and would become localised to said surface at the site of the second oligonucleotide probe. By detecting the accumulation of the detection moiety at the site during the amplification process a real-time signal would be obtained providing for a quantitation of the number of copies of target nucleic acid present in the sample. Thus according to an embodiment of the invention, two or more of steps a), b) and c) are performed simultaneously.

In the performance of those embodiments wherein one of the first and second oligonucleotide probes is blocked at the 3' end from extension by the DNA polymerase and is not capable of being cleaved by either the first or second restriction enzymes and is contacted with the sample simultaneously to the performance of step a), we have not observed any significant inhibition of the rate of the amplification, indicating that the pre-detector species accumulates in real-time without disrupting the optimal cyclical amplification process. This contrasts with attempts to engineer asymmetric SDA by utilising an unequal primer ratio with the goal of producing an excess of one amplicon strand over the other. Rather than seeking to use the blocked oligonucleotide probe to remove one amplicon strand from the reaction and thus increase the proportion of the other strand, the present invention is focussed on the production and detection of the detector species exploiting a blocked probe to facilitate the exposure of a single stranded region during the amplification process. Thus not only did we not observe any inhibitory effects on the amplification process in said embodiments but we observed a surprising enhancement of the signal produced corresponding to an increased amount of detector species, of at least 100-fold in certain embodiments, see Example 2 (FIG. 6).

Further, said embodiments of the method of the invention wherein one of the first and second oligonucleotides probes is blocked at the 3' end from extension by the DNA polymerase and is not capable of being cleaved by either the first or second restriction enzymes and is contacted with the sample simultaneously to the performance of step a), represent a fundamental advantage over reported attempts to integrate NEAR with nucleic acid lateral flow in a multistep process without blocked probes. For example, in WO2014/164479 a long incubation of 30 minutes at 48° C. was required to visualise amplification product using nucleic acid lateral flow, which represents a major impediment to the use of that method in a point-of-care diagnostic device, particularly a low-cost or single-use device. In stark contrast, the method of the invention readily performs an equivalent amplification in under 5 minutes and at a lower temperature of incubation, e.g. 40-45° C. In a further direct comparative study (see Example 10), the method of the invention demonstrates a surprising vastly superior rate compared to a the prior art method (WO2014/164479) resulting from a combination of the use of a restriction enzyme that is not a nicking enzyme, the use of a modified dNTP base and the use of said blocked oligonucleotide probe.

It will also be appreciated that the other of the first and second oligonucleotide probes may be blocked at the 3' end from extension by the DNA polymerase, and/or is not capable of being cleaved by either the first or second restriction enzymes, as described above.

An integral aspect of the method is the use of one or more restriction enzyme that is not a nicking enzyme, but is capable of recognising its recognition sequence and cleaving only one strand of its cleavage site when said recognition sequence and cleavage site are double stranded, the cleavage of the reverse complementary strand being blocked due to the presence of one or more modifications incorporated into said reverse complementary strand by a strand displacement DNA polymerase using one or more modified dNTP, e.g. a dNTP that confers nuclease resistance following its incorporation by a polymerase.

A "restriction enzyme" [or "restriction endonuclease"] is a broad class of enzyme which cleaves one or more phosphodiester bond on one or both strands of a double stranded nucleic acid molecule at specific cleavage sites following binding to a specific recognition sequence. A large number of restriction enzymes are available, with over 3,000 reported and over 600 commercially available, covering a wide range of different physicochemical properties and recognition sequence specificities.

A "nicking enzyme" [or "nicking endonuclease"] is a particular subclass of restriction enzyme, that is only capable of cleaving one strand of a double stranded nucleic acid molecule at a specific cleavage site following binding to a specific recognition sequence, leaving the other strand intact. Only a very small number (c.10) nicking enzymes are available including both naturally occurring and engineered enzymes. Nicking enzymes include bottom strand cutters Nb.BbvCI, Nb.BsmI, Nb.BsrDI, Nb.BssSI and Nb.BtsI and top strand cutters Nt.AlwI, Nt.BbvCI, Nt.BsmAI, Nt.BspQI, Nt.BstNBI and Nt.CviPII.

Restriction enzymes that are not nicking enzymes, which are exclusively employed in the method of the invention, despite being capable of cleaving both strands of a double stranded nucleic acid, can in certain circumstances also cleave or nick only one strand of their double stranded DNA cleavage site following binding to their recognition sequence. This can be accomplished in a number of ways. Of particular relevance to the present method this can be accomplished when one of the strands within the double stranded nucleic acid at the cleavage site is rendered not capable of being cleaved due to one strand of the double stranded nucleic acid target site being modified such that the phosphodiester bond of the cleavage site on one of the strands is protected using a nuclease resistant modification, such as a phosphorothioate (PTO), boranophosphate, methylphosphate or peptide internucleotide linkage. Certain modified internucleotide linkages, e.g. PTO linkages, can be chemically synthesised within oligonucleotides probes and primers or integrated into a double stranded nucleic acid by a polymerase, such as by using one or more alpha thiol modified deoxynucleotide. Thus, in an embodiment the one or more modified dNTP is an alpha thiol modified dNTP. Typically the S isomer is employed which is incorporated and confers nuclease resistance more effectively.

Due to the very large number of restriction enzymes that are not nicking enzymes available, a wide range of enzymes with different properties are available to be screened for the desired performance characteristics, e.g. temperature profile, rate, buffer compatibility, polymerase cross-compatibility, recognition sequence, thermostability, manufacturability etc., for use in the method for a given application. In contrast the fact that only a small number of nicking enzymes are available limits the potential of prior art methods that use nicking enzymes, and can lead to a lower reaction rate (sensitivity, time to result) and a higher reaction temperature, for example. Restriction enzymes that are not nicking enzymes selected for use in the method may be naturally occurring or engineered enzymes.

In selecting the restriction enzyme that is not a nicking enzyme for use in the method the skilled person will recognise that it is necessary to identify an enzyme with an appropriate cleavage site in order to ensure that a modification is incorporated at the correct position to block the cleavage of the relevant strand and not the other strand. For example, in an embodiment in which a modified dNTP, such as an alpha thiol dNTP, is used it may be preferable to select a restriction enzyme with a cleavage site that falls outside of the recognition sequence, such as an asymmetric restriction enzyme with a non-palindromic recognition sequence, in order to provide sufficient flexibility to position the primers such that the target nucleic acid sequence contains the modified nucleotide base at the appropriate location to block the cleavage of the relevant strand following its incorporation. For example, if alpha thiol dATP is used the reverse complementary sequence of the restriction enzyme cleavage site in the relevant oligonucleotide primer would contain an Adenosine base downstream of the cleavage position in said reverse complementary strand but not contain an Adenosine base downstream of the cleavage site in the primer sequence, in order to ensure that primer is cleaved appropriately in the performance of the method. Therefore asymmetric restriction enzymes with a non-palindromic recognition sequence that cleave outside of their recognition sequence are ideally suited for use in the present invention. Partial or degenerate palindromic sequence recognising restriction enzymes that cleave within their recognition site may also be used. Nuclease resistant nucleotide linkage modifications, e.g. PTO, may be used to block the cleavage of either strand by a wide range of commercially available double strand cleaving agents of various different classes, including type IIS and type IIG restriction enzymes with both partial or degenerate palindromic and asymmetric restriction recognition sequences, in order to enable their use in the method of the invention.

Restriction enzyme(s) are typically employed in the method in an amount of 0.1-100 Units, where one unit is defined as the amount of agent required to digest 1 μg T7 DNA in 1 hour at a given temperature (e.g. 37° C.) in a total reaction volume of 50 μl. However, the amount depends on a number of factors such as the activity of the enzyme selected, the concentration and form of the enzyme, the anticipated concentration of the target nucleic acid, the volume of the reaction, the concentration of the primers and the reaction temperature, and should not be considered limiting in any way. Those skilled in the art will understand that a restriction enzyme employed in the method will require a suitable buffer and salts, e.g. divalent metal ions, for effective and efficient function, control of pH and stabilisation of the enzyme.

In an embodiment the first and second restriction enzyme are the same restriction enzyme. By using only a single restriction enzyme the method is simplified in a number of ways. For example, only a single enzyme that is compatible with other reaction components needs to be identified, optimised for performance of the method, manufactured and stabilised. Utilising a single restriction enzyme also simplifies design of oligonucleotide primers and supports the symmetry of the amplification process.

In the method the restriction enzymes cleave only one strand of the nucleic acid duplex, and thus following cleavage they present an exposed 3' hydroxyl group which can act as an efficient priming site for a polymerase. A polymerase is an enzyme that synthesises chains or polymers of nucleic acids by extending a primer and generating a reverse complementary "copy" of a DNA or RNA template strand using base-pairing interactions. A polymerase with strand displacement capability is employed in the performance of the method in order that strands are appropriately displaced to affect the amplification process. The term "strand displacement" refers to the ability of a polymerase to displace downstream DNA encountered during synthesis. A range of polymerases with strand displacement capability that operate at different temperatures have been characterised and are commercially available. For example, Phi29 polymerase has a very strong ability to strand displace. Polymerases from *Bacillus* species, such as Bst DNA Polymerase Large Fragment, typically exhibit high strand displacing activity and are well-suited to use in the performance of the method. *E. coli* Klenow fragment (exo-) is another widely used strand displacement polymerase. Strand displacement polymerases may be readily engineered, such as KlenTaq such as by cloning of only the relevant active polymerase domain of an endogenous enzyme and knock-out of any exonuclease activity. For the performance of the method wherein the single stranded target nucleic acid is RNA, RNA dependent DNA synthesis (reverse transcriptase) activity is also required, which activity may be performed by the strand displacement polymerase and/or by a separate additional reverse transcriptase enzyme in step a), e.g. M-MuLV or AMV.

Polymerase(s) are typically employed in the relevant steps of the method in an appropriate amount which is optimised dependent on the enzyme, concentration of reagents and desired temperature of the reaction. For example, of 0.1-100 Units of a *Bacillus* polymerase may be used, where one unit is defined as the amount of enzyme that will incorporate 25 nmol of dNTP into acid insoluble material in 30 minutes at 65° C. However, the amount depends on a number of factors such as the activity of the polymerase, its concentration and form, the anticipated concentration of the target nucleic acid, the volume of the reaction, the number and concentration of the oligonucleotide primers and the reaction temperature, and should not be considered limiting in any way.

Those skilled in the art will know that polymerases require dNTP monomers to have polymerase activity and also that they require an appropriate buffer, with components such as buffer salts, divalent ions and stabilising agents. In addition, one or more modified dNTP is used in the method in order to block the cleavage of the reverse complementary strand of the primers following incorporation by the strand displacement polymerase. Typically when a single modified dNTP is used, the dNTPs used in the method shall omit the corresponding base. For example, in an embodiment in which the modified dNTP is alpha thiol dATP, the dNTPs shall comprise only dTTP, dCTP and dGTP and shall not include dATP. Removing the corresponding natural dNTP base ensures that the all of the required bottom strand cleavage sites within the reverse complementary sequence of the primers are blocked because only the modified base is available for incorporation by the polymerase, however complete or partial removal of the corresponding natural dNTP base is not essential. dNTPs may typically be used in the method at similar concentrations to those employed in other polymerase methods, such as concentrations ranging from 10 micromolar to 1 millimolar, although the concentration of dNTP for the method may be optimised for any given enzyme and reagents, in order to maximise activity and minimise ab initio synthesis to avoid background signal generation. Given that certain polymerases can exhibit a lower rate of incorporation with one or more modified dNTP base the one or more modified base may be used in the method at a higher relative concentration that the unmodified dNTPs, such as at a five-fold higher concentration, although this should be considered non-limiting.

The use of one or more modified dNTP is an integral feature of the present invention which offers an important advantage in addition to providing for the restriction enzymes to cleave only one strand of their restriction sites. For example, certain modified dNTPs, such as alpha thiol dNTPs, lead to a reduction in the melting temperature (Tm) of the DNA into which they are incorporated which means the oligonucleotide primers and probes used in the method have a greater affinity for hybridisation to species within the amplification product than any competing modified dNTP complementary strands produced during the amplification. This key feature enhances the amplification rate because, for example, when one of the displaced strands hybridises to its reverse complement to produce an "unproductive" end-point species, it more readily dissociates than the "productive" hybridisation of said displaced strand to a further primer due to the presence of one or more modified bases leading to a reduction in the Tm of hybridisation. It has been reported that phosphorothioate internucleotide linkages can reduce the Tm, the temperature at which exactly one half the single strands of a duplex are hybridised, by 1-3° C. per addition, a substantial change in the physicochemical properties. We have also observed an enhanced rate of strand displacement when phosphorothioate nucleotide linkages are present in a DNA sequence. Furthermore, the oligonucleotide probes used in the method, whether contacted with the sample simultaneously to the performance of step a) or subsequently, possess a higher affinity for those species within the amplification product than any competing modified species and can thus preferentially hybridise or even displace hybridised strands to facilitate production of the detector species. The reduced Tm and enhanced displacement of amplification product species as a result of the modified internucleotide linkages they contain serve to fundamentally enhance the rate of the method and reduce the temperature required for rapid amplification to occur.

In addition to the rate enhancement resulting from the use of one or more modified nucleotide, the specificity of hybridisation of the oligonucleotide primers and probes of the method is also enhanced. Given that typically all of the bases of one particular nucleotide are substituted within amplification product, the hybridisation sites of the primers and probes typically contain modified bases and the reduced Tm resulting from phosphorothioate internucleotide linkages, for example, means that sequence mismatches from non-specific hybridisation are less likely to be tolerated.

Thus the integral feature of the method of the invention for one or more modified dNTP leads to fundamental benefits that enhance both the sensitivity and specificity of amplification and are in stark contrast to known methods without such a requirement for modified nucleotides, such as NEAR (WO2009/012246), including NEAR variants with software optimised primers (WO2014/164479) or a warm start or controlled reduction in temperature (WO2018/002649).

A number of different modified dNTPs, such as modified dNTPs that confer nuclease resistance following their incorporation by a polymerase, exist and can be employed in the method to accomplish resistance to cleavage by the restriction enzyme and, in embodiments, other features to enhance the performance of the method for a given application. In addition to alpha thiol dNTPs which provide for nuclease resistance and a reduction in Tm, modified dNTPs that are reported to have potential for polymerase incorporation and to confer nuclease resistance, include equivalent nucleotide derivatives, such as Borano derivatives, 2'-O-Methyl (2'OMe) modified bases and 2'-Fluoro bases. Other modified dNTPs or equivalent compounds that may be incorporated by polymerases and used in embodiments of the method to enhance particular properties of the method, include those that decrease binding affinity, e.g. Inosine-5'-Triphosphate or 2'-Deoxyzebularine-5'-Triphosphate, those that increase binding specificity, e.g. 5-Methyl-2'-deoxycytidine-5'-Triphosphate or 5-[(3-Indolyl)propionamide-N-allyl]-2'-deoxyuridine-5'-Triphosphate, and those that enhance the synthesis of GC rich regions, e.g. 7-deaza-dGTP. Certain modifications can increase Tm providing further potential for control of the hybridisation events in embodiments of the method.

Steps a), b) and c) may be performed over a wide range of temperatures. The optimal temperature for each step is determined by the temperature optimum of the relevant polymerase and restriction enzymes and the melting temperature of the hybridising regions of the oligonucleotide primers. Notably the method does not use temperature cycling in step a). Furthermore, the amplification step a) does not require any controlled oscillation of temperature, nor any hot or warm start, pre-heating or a controlled temperature decrease. The method allows the steps to be performed over a wide temperature range, e.g. 15° C. to 60° C., such as 20 to 60° C., or 15 to 45° C. According to an embodiment, step a) is performed at a temperature of not more than 50° C., or about 50° C. Given the wide range of restriction enzymes that are not nicking enzymes available for use in the method, it is possible to select restriction enzymes with a rapid rate at relatively low temperatures compared to alternative methods using nicking enzymes. The use of one or more modified nucleotides also reduces the temperature of amplification required. In addition to having the potential for a lower optimal temperature profile compared to known methods, the method of the invention can be performed over an unusually broad range of temperatures. Such features are highly attractive for use of the method in a low-cost diagnostic device, where controlled heating imposes complex physical constraints that increase the cost-of-goods of such a device to a point where a single-use or instrument-free device is not commercially viable. A number of assays have been developed using the method that can perform rapid detection of target nucleic acid at ambient temperature or at around 37° C., for example. As such, in a further embodiment step a) is performed at a temperature of not more than 45° C., or about 45° C. It may be preferable to initiate the method at a temperature lower than the targeted temperature in order to simplify the user steps and decrease the overall time to result. As such in a further embodiment of the method, the temperature of step a) is increased during the amplification. For example, the temperature of the method may start at ambient temperature, such as 20° C., and increase over a period, such as two minutes, to the final temperature, such as approximately 45° C. or 50° C. In an embodiment the temperature is increased during the performance of step a), such as an increase from an ambient starting temperature, e.g. in the range of 15-30° C., up to a temperature in the range of 40-50° C.

The low temperature potential and versatility of the method of the invention means that, in contrast to known methods, it is compatible with the conditions required for a range of other assays, such as immunoassays or enzymatic assays for the detection of other biomarkers, such as proteins or small molecules. Therefore the method can be used, for example, for the simultaneous detection of both nucleic acids and proteins or small molecules of interest within a sample. The components required for performance of the method, including restriction enzymes that are not nicking enzymes, strand displacement DNA polymerase, oligonucleotide primers, oligonucleotide probes, dNTPs and one or more modified dNTP, may be lyophilised or freeze-dried for stable storage and the reaction may then be triggered by rehydration, such as upon addition of the sample. Such lyophilisation or freeze-drying for stable storage typically requires addition of one or more excipients, such as trehalose, prior to drying the components. A very wide range of such excipients and stabilisers for lyophilisation or freeze-drying are known and available for testing in order to identify a suitable composition for the components required for the performance of the method.

It will be apparent to one skilled in the art that the method of the invention, being a polymerase-based amplification method, may be enhanced by the addition of one or more additive that has been shown to enhance PCR or other polymerase based amplification methods. Such additives include but are not limited to tetrahydrothiophene 1-oxide, L-lysine free base, L-arginine, glycine, histidine, 5-aminovaleric acid, 1,5-diamino-2-methylpentane, N,N'-diisopropylethylenediamine, tetramethylenediamine (TEMED), tetramethylammonium chloride, tetramethylammonium oxylate, methyl sulfone acetamide, hexadecyltrimethylammonium bromide, betaine aldehyde, tetraethylammoniumchloride, (3-carboxypropyl)trimethylammoniumchloride, tetrabutylammoniumchloride, tetrapropylammoniumchloride, formamide, dimethylformamide (DMF), N-methylformamide, N-methylacetamide, N,N-dimethylacetamide, L-threonine, N,N-dimethylethylenediamine, 2-pyrrolidone, HEP (N-hydroxyethylpyrrolidone), NMP (N-methylpyrrolidone) and 1-methyl, 1-cyclohexyl-2-pyrrolidone (pyrrolidinones), δ-valerolactam, N-methylsuccinimide, 1-formylpyrrolidine, 4-formylmorpholine, DMSO, sulfolane, trehalose, glycerol, Tween-20, DMSO, betaine and BSA.

Our investigations have revealed that the present method is effective over a wide range of target nucleic acid levels including detection down to very low, even single, copy numbers. The oligonucleotide primers are typically provided in vast excess over target nucleic acid. Typically the concentration of each primer is in the range 10 to 200 nM although that should be considered non-limiting. A higher primer concentration can enhance the efficiency of hybridisation and therefore increase the rate of the reaction. However, non-specific background effects, such as primer dimers, can also be observed at high concentration and therefore the concentration of the first and second oligonucleotide primers forms part of the optimisation process for any given assay employing the method. In an embodiment the first and the second oligonucleotide primers are provided at the same concentration. In an alternative embodiment one of the first and second oligonucleotide primers is provided in excess of the other. The rate of reaction may be reduced in embodiments wherein one of the primers is provided in excess of the other due to the natural symmetry of the cyclical amplification process, however in certain circumstances it can be used to reduce non-specific background signal in the method and/or to enhance the ability of the first and second oligonucleotide probes to hybridise to produce the detector species. It is desirable that both primers are present at such as level as to not become limiting before sufficient detector species has been produced for detection with the selected means of detection.

There are a number of considerations for the design of the oligonucleotide primers for performance of the method. Each of the first and second oligonucleotide primers must comprise in the 5' to 3' direction one strand of a restriction enzyme recognition sequence and cleavage site and a hybridising region, wherein said hybridising region is capable of hybridising to a first hybridisation region in the target nucleic acid in the case of the first primer and to the reverse complement of a second hybridisation sequence upstream of the first hybridisation sequence in the target nucleic acid in the case of the second primer. Thus a pair of primers is designed to amplify a region of the target nucleic acid. The restriction enzyme recognition sequence of the primers is not typically present within the target nucleic acid sequence and thus forms an overhang during the initial hybridisation events before being introduced to the amplicon (see FIG. 1). In the event that an asymmetric restriction enzyme is used the cleavage site is typically downstream of the recognition sequence and may therefore, optionally, be present within the hybridising sequence of the primer.

The oligonucleotide primers are designed such that following their cleavage in the method, the sequence 5' of the cleavage site forms an upstream primer with sufficient melting temperature (Tm) to remain hybridised to its reverse complementary strand under the desired reaction conditions and to displace the strand downstream of the cleavage site following extension of the 3' hydroxyl group by the strand displacement DNA polymerase. Thus an additional "stabilising" region may be included at the 5' end of the oligonucleotide primers, the optimum length of which is determined by the position of the cleavage site relative to the recognition sequence for the relevant restriction enzyme and other factors such as the temperature to be employed for the amplification in step a). Thus in an embodiment the first and/or second oligonucleotide primers comprise a stabilising sequence upstream of the restriction enzyme recognition sequence and cleavage site, such as at the 5' end, and e.g. of 5 or 6 bases in length.

During primer design it is necessary to define the sequence and length of each hybridising region in order to permit optimal sequence specific hybridisation and strand displacement to ensure specific and sensitive amplification in the method. The positioning of the primers within the target nucleic acid to be detected, e.g. within the genome of a viral or bacterial pathogen, may be varied to define the sequence of the hybridising region of the primers and thus to select primers with the optimal sensitivity and specificity for amplification and compatibility with the oligonucleotide probes. Different primer pairs can therefore be screened to identify the optimal sequence and positioning for performance of the method. Typically the length of the hybridising region of the primers is designed such that its theoretical Tm permits efficient hybridisation at the desired reaction temperature but is also readily displaced following cleavage. During primer design, the theoretical Tm of the hybridising sequence and the sequence of the displaced strands are considered in the context of the likely temperature of the reaction and the restriction enzyme selected, which is balanced with the theoretical improvement to sequence-derived specificity of binding that can result as sequence length is increased. Our various investigations have indicated considerable versatility in the design of the primers to be used effectively in the method. In an embodiment the hybridising region of the first and/or second oligonucleotide primers is between 6 and 30, e.g. 9 and 16, bases in length. In further embodiments modifications, such as non-natural bases and alternative internucleotide linkages or abasic sites may be employed in the hybridising regions of the primers to refine their properties and the functioning of the method for a particular application. For example a modification that enhances Tm, such as PNA, LNA or G-clamp may permit a shorter and more specific primer hybridisation region which enables a shorter amplicon and thus enhances the rate of amplification.

Our various investigations have revealed that the rate of the method and its sensitivity may be enhanced by having a short amplicon and thus in certain embodiments it can be preferable to shorten both the overall length of the primers, including their hybridising sequence, and to position the primers with only a short gap, such as 10 or 15 nucleotide bases or less, between the first and second hybridisation sequences in the target nucleic acid. In an embodiment the first and second hybridisation sequences in the target nucleic acid are separated by 0 to 15 or 0 to 6 bases, in certain embodiments they are separated by 3 to 15 or 3 to 6 bases, e.g. 5, 7 or 11 bases. In a further embodiment the hybridisation sequences are overlapping, such as by 1 to 2 bases.

There are a number of considerations to the design of the sequence of the oligonucleotide probes for use in the method. Firstly, the region in the first oligonucleotide probe hybridising to the first single stranded detection sequence and the region in the second oligonucleotide probe hybridising to the second single stranded detection sequence are typically designed such that they are non-overlapping or have minimal overlap, to permit both oligonucleotide probes to bind at the same time to the at least one species within the amplification product. They are also typically designed to hybridise mainly to sequence that falls between the position of the cleavage site in one strand of the amplification product species and the position opposite the cleavage site on the reverse complementary strand thereto in order to ensure the one or more species within the amplification product are efficiently targeted and that both oligonucleotide probes bind to the same strand. For any given pair of primers, either strand may be selected for targeting by the oligonucleotide probes. Given that the oligonucleotide probes are not typically extended by a polymerase in the method, the hybridising sequences are designed based upon the relevant sequence of the species within the amplification product, which determines their Tm, % GC and the experimental performance data obtained. In an embodiment, the hybridising sequence of the first and second oligonucleotide probes is 9 to 20 nucleotide bases long. In an embodiment wherein the first and second hybridisation sequences in the target nucleic acid are separated by 0 bases, the sequence of the hybridising regions of one of the oligonucleotide probes may correspond to one of the oligonucleotide primers and the hybridising region of the other oligonucleotide probe would correspond to the reverse complement of the other oligonucleotide primer. However, the length of the hybridising sequences may be truncated in order to optimise the properties of the oligonucleotide probes for the desired embodiment of the method and avoid any inhibitory effects in the event that all or part of step b) is performed simultaneously to step a). In the event that the first or second oligonucleotide probe encompasses a recognition sequence and cleavage site for either the first or second restriction enzyme and said oligonucleotide probe is contacted with the sample simultaneously to the performance of step a), the cleavage site within said probe is typically blocked, for example by the inclusion of a modified internucleotide linkage, e.g. a phosphorothioate linkage, during the chemical synthesis of the probe or introduction of a mismatch to remove said recognition sequence. Other than the hybridising regions, there is considerable versatility to the sequence of the oligonucleotide probes and to any modified nucleotide bases, nucleotide linkages or other modifications that they may comprise. Modified bases that may be chemically inserted into oligonucleotides to alter their properties and may be employed in embodiments of the methods, such as 2-Amino-dA, 5-Methyl-dC, Super T®, 2-Fluoro bases and G clamp provide for an increase in Tm, whilst others such as Iso-dC and Iso-G, can enhance specificity of binding without increasing Tm. Other modifications such as inosine or abasic sites may decrease the specificity of binding. Modifications known to confer nuclease resistance include inverted dT and ddT and C3 spacers. Modifications can increase or decrease Tm and provide potential for control of the hybridisation events in embodiments of the method. Use of modified bases within the hybridising regions of the oligonucleotide probes provides an opportunity to improve the performance of the oligonucleotide probes such as by enhancing their binding affinity without increasing the length of the hybridising region. In an embodiment modified bases within one or both oligonucleotide probes permit them to hybridise more effectively than, and thus out-compete, any species within the amplification product with complementarity to the relevant single stranded detection sequence.

In embodiments wherein one of the first and second oligonucleotide probes is blocked at the 3' end from extension and is not capable of being cleaved and is contacted with the sample simultaneously to the performance of step a), typically said one oligonucleotide probe will comprise an additional 5' region, which provides the opportunity for the stabilisation of the pre-detector species as described (see FIG. 2). In an embodiment said one oligonucleotide probe comprises the exact sequence of one of the oligonucleotide primers, but contains a modification at the 3' end to block its extension by the strand displacement DNA polymerase and a single phosphorothioate internucleotide linkage to block the restriction enzyme cleavage site. Such an embodiment simplifies assay design and ensures that no additional sequence motifs are introduced which may lead to non-specific background amplification.

The first and second oligonucleotide probes that produce the detector species are preferably provided at a level wherein the number of copies of detector species produced is sufficiently above the limit of detection of the means employed for said detector species to be readily detected. Furthermore the efficiency of hybridisation by the first and/or second oligonucleotide probe(s) are influenced by their concentration. Typically the concentration of an oligonucleotide probe contacted with the sample simultaneously to the performance of step a) may be similar to the concentration of the oligonucleotide primers, e.g. 10 to 200 nM, although that should be considered non-limiting. In an embodiment the concentration of one or both oligonucleotide probes is provided in excess of the concentration of one or both oligonucleotide primers, whist in another embodiment the concentration of one or both oligonucleotide probes is provided at a lower concentration than one or both oligonucleotide primers. In the event one or both oligonucleotide probes is contacted to the sample subsequent to the performance of the amplification step a), a higher concentration may be permitted as necessary to accomplish the most efficient hybridisation, without any consideration of inhibition to the amplification step a) that may result.

Hybridisation sequences are a key feature of both the oligonucleotide primers and oligonucleotide probes for performance of the method. Hybridisation refers to sequence specific hybridisation which is the ability of an oligonucleotide primer or probe to bind to a target nucleic acid or species within the amplification product by virtue of the hydrogen bond base pairing between complementary bases in the sequence of each nucleic acid. Typical base pairings are Adenine-Thymine (A-T), or Adenine-Uracil in the case of RNA or RNA/DNA hybrid duplexes, and Cytosine-Guanine (C-G), although a range of natural and non-natural analogues of nucleic acid bases are also known with particular binding preferences. Furthermore, in the present invention, the complementarity region of an oligonucleotide probe or primer does not necessarily need to comprise wholly natural nucleic acid bases in a sequence with complete and exact complementarity to its hybridisation sequence in the target nucleic acid or species within the amplification product; rather for the performance of the method the oligonucleotide probes/primers only need to be capable of sequence specific hybridisation to their target hybridisation sequence sufficiently to form the double stranded sequence necessary for the correct functioning of the method, including the cleavage by the restriction enzymes and extension by the strand displacement DNA polymerase. Therefore such hybridisation may be possible without exact complementarity, and with non-natural bases or abasic sites. In an embodiment, the hybridising regions of an oligonucleotide primer or oligonucleotide probe used in the method may consist of complete complementarity to the sequence of the relevant region of the target nucleic acid or species within the amplification product, or its reverse complementary sequence, as appropriate. In other embodiments there are one or more non-complementing base pairs. In some circumstances it may be advantageous to use a mixture of oligonucleotide primers and/or probes in the method. Thus, by way of example, in the case of a target nucleic acid comprising a single nucleotide polymorphism (SNP) site having two polymorphic positions, a 1:1 mixture of oligonucleotide primers and oligonucleotide probes differing in that position (each component having complementarity to the respective base of the SNP) may be employed. During manufacture of oligonucleotides it is routine practice to randomise one or more bases during the synthesis process.

One skilled in the art will understand that amplification processes involving polymerases can suffer from non-specific background amplification such as that resulting from ab initio synthesis and/or primer-primer binding. Whilst the method of the invention typically exhibits more rapid amplification when the length of amplicon is designed to be as short as possible, e.g. by minimising the hybridising sequences of the primers, the gap between the first and second hybridisation sequences in the target nucleic acid and the length of any stabilising region, to the extent possible whilst still retaining function at the given reaction temperature. With shorter amplicons non-specific background may be exacerbated due to the fact that all necessary sequence to produce the amplification product species is provided by the oligonucleotide primers. In the event an amplicon is produced in a non-target specific manner comprising both the first oligonucleotide primer and the second oligonucleotide primer "connected" via an ab initio synthesised DNA or primer-primer binding, a false positive result could occur in the method. The use of two oligonucleotide probes in the present method allows for a variety of embodiments of the method encompassing additional features to minimise any possibility of non-target specific background signal. Such embodiments made possible by the use of two oligonucleotide probes present a substantial advantage over known methods in this regard.

Figure 8:
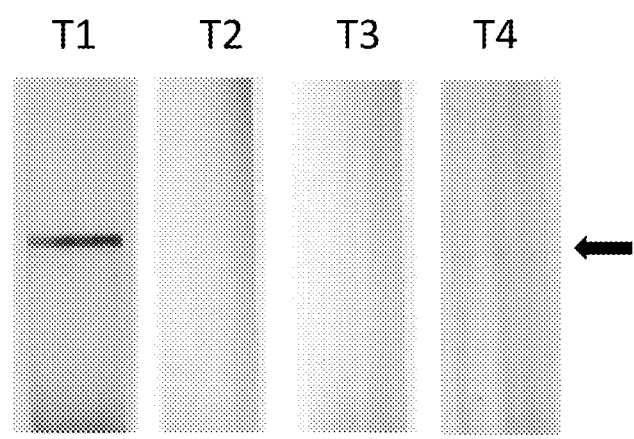
FIG. 8. Performance of the method wherein the first and second hybridisation sequences in the target nucleic acid are separated by 5 bases (see Example 4).

One approach is to separate the first and second hybridisation sequences in the target nucleic acid to provide a target-based sequence specificity check using the oligonucleotide probes of the method. Thus in an embodiment, the first and second hybridisation sequences in the target nucleic acid are separated by 3 to 15 or by 3 to 6 bases, e.g. 5, 7 or 11 bases. This gap between the primers presents the optimal size gap to provide for an additional specificity check on species within the amplification product whilst still maintaining the enhanced rate of a short amplicon. Thus in an embodiment, in step b) either the first or second single stranded detection sequence in the at least one species within the amplification product includes at least 3 bases of the sequence corresponding to said 3 to 15 or 3 to 6 bases. For example, we have demonstrated the potential to distinguish a specific target-dependent amplification product from non-target specific background amplification products, as shown in Example 4 (FIG. 8).

Figure 4:
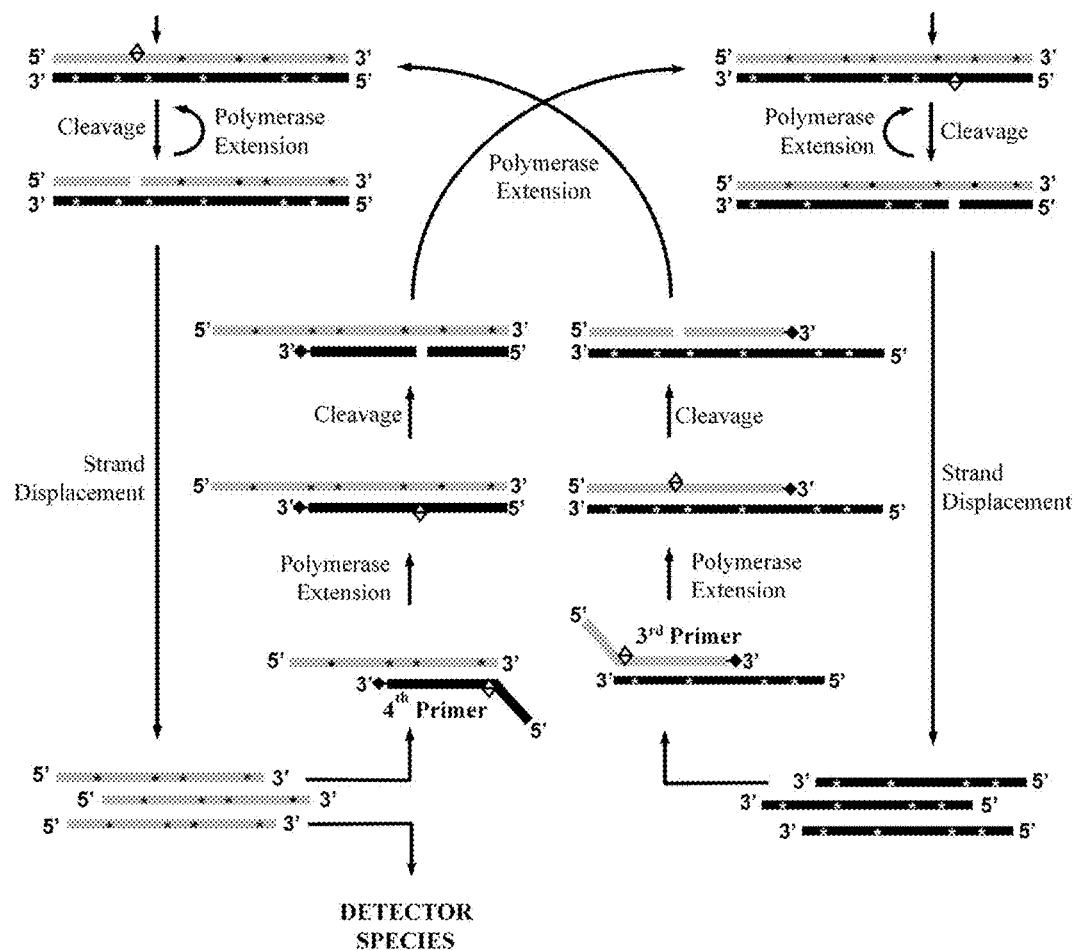
FIG. 4. Schematic representation of part of step a) of the method wherein the sample is additionally contacted with a third and fourth oligonucleotide primer in step a).

In an alternative approach the concentration of the first and/or second oligonucleotide primers is decreased to reduce the probability of background resulting from ab initio amplification and from primer-primer binding. In order to ensure the rate of the amplification is maintained, additional oligonucleotide primers that are blocked at the 3' end from extension by the strand displacement DNA polymerase may be used. In this embodiment, whilst the unblocked first and second oligonucleotide primers are available at sufficient concentration for the initial hybridisation and extension events to produce the amplicon from the target nucleic acid, subsequent amplification proceeds with the blocked primers, which are preferably provided at higher concentration, wherein cleavage of the blocked primers occurs prior to their extension and strand displacement in order to remove the 3' blocking modification and allow the amplification process to proceed without detriment (see FIG. 4). Thus in an embodiment, the sample additionally is contacted in step a) with: (A) a third oligonucleotide primer which third primer comprises in the 5' to 3' direction one strand of the recognition sequence and cleavage site for the first restriction enzyme and a region that is capable of hybridising to the first hybridisation sequence in the target nucleic acid and wherein said third primer is blocked at the 3' end from extension by the DNA polymerase; and/or (B) a fourth oligonucleotide primer which fourth primer comprises in the 5' to 3' direction one strand of the recognition sequence and cleavage site for the second restriction enzyme and a region that is capable of hybridising to the reverse complement of the second hybridisation sequence in the target nucleic acid and wherein said fourth primer is blocked at the 3' end from extension by the DNA polymerase. In a further embodiment, when present the third oligonucleotide primer is provided in excess of the first oligonucleotide primer and when present the fourth oligonucleotide primer is provided in excess of the second oligonucleotide primer. By reducing the concentration of the first and second oligonucleotide primers substantially, offset by the presence of the third and fourth oligonucleotide primers, the maximum potential benefit in terms of removal of non-target dependent background amplification is obtained. Other than the presence of the 3' modification to block polymerase extension which may readily be achieved through, for example, use of a 3' phosphate or C-3 modification during oligonucleotide primer synthesis, the same design parameters as employed for the first and second primers apply to the third and fourth primers.

Embodiments of the method of the invention that provide for enhanced specificity and removal of background amplification as described above, provide improved rigour of sequence verification, which enables low temperature reactions to be performed without loss of specificity and/or enables increased multiplexing, where multiple reactions are performed for the simultaneous detection of multiple targets. The benefits of this rigorous specificity also mean that the method can tolerate a broad temperature range and suboptimal conditions (e.g. reagent concentrations) without loss of specificity. For example, we have performed the method with a 20% increase or decrease in the concentration of all components and we have performed the method with a substantial period at ambient temperature following performance of the amplification in step a) in each case without any loss of specificity observed. Therefore such embodiments represent important advantages of the method of the invention over known methods and mean that it is ideally suited to exploitation in a low-cost and/or single-use diagnostic device.

Detection of the detector species in step c) can be accomplished by any technique which differentially detects the presence of the detector species from the other reagents and components present in the sample. Alternatively the presence or level of the detector species can be inferred from the depletion of one or more reaction components such as the first or second oligonucleotide probe. From a wide range of physicochemical techniques available for use in the detection of the detector species, those capable of generating a sensitive signal that only exists following hybridisation of the first oligonucleotide probe and second oligonucleotide probe to the relevant species in the amplification product are prioritised for use in the method. It will be apparent to a skilled person that a range of colorimetric or fluorometric dyes exist that may be readily attached to the first oligonucleotide probe and form the basis of its detection, either visually or using instrumentation, such as absorbance or fluorescence spectroscopy.

Thus in an embodiment, the moiety that permits the detection of the first oligonucleotide probe, is a colorimetric or fluorometric dye or a moiety that is capable of attachment to a colorimetric or fluorometric dye such as biotin.

Embodiments of the method employing colorimetric dyes have the advantage of not requiring an instrument to perform fluorescence excitation and detection and potentially of allowing the presence of the target nucleic acid to be determined by eye. Colorimetric detection can be achieved by directly attaching a colorimetric dye or moiety capable of attachment to a colorimetric dye to the first oligonucleotide probe prior to its use in the method, or alternatively specifically attaching or binding the dye or moiety to the probe fragment following cleavage. For example, the first oligonucleotide probe may contain a biotin moiety that permits its binding to a streptavidin conjugated colorimetric dye for its subsequent detection. One such example of a colorimetric dye that may be used in detection is gold nanoparticles Similar methods can be employed with a variety of other intrinsically colorimetric moieties, of which a very large number are known, such as carbon nanoparticles, silver nanoparticles, iron oxide nanoparticles, polystyrene beads, quantum dots etc. A high extinction coefficient dye also provides potential for sensitive real-time quantification in the method.

A number of considerations are taken into account when choosing an appropriate dye for a given application. For example, in embodiments where it is intended to perform visible colorimetric detection in solution, it would generally be advantageous to choose larger size particles and/or those with a higher extinction coefficient for ease of detection, whereas embodiments incorporating a lateral flow membrane intended for visible detection, might benefit from the ability of smaller sized particles to more rapid diffuse along a membrane. While various sizes and shapes of gold nanoparticles are available, a number of other colorimetric moieties of interest are also available which include polystyrene or latex based microspheres/nanoparticles. Particles of this nature are also available in a number of colours, which can be useful in order to tag and differentially detect different detector species during the performance of the method, or "multiplex" the colorimetric signal produced in a detection reaction.

Fluorometric detection can be achieved through the use of any dye that under appropriate excitation stimulus, emits a fluorescent signal leading to subsequent detection of the detector species. For example, dyes for direct fluorescence detection include, without limitation: quantum dots, ALEXA dyes, fluorescein, ATTO dyes, rhodamine and texas red. In embodiments of the method that employ a fluorescent dye moiety attached to an oligonucleotide probe, it is also possible to perform detection based on fluorescence resonance energy transfer (FRET), such as employed in Taqman quantitative PCR or Molecular Beacon based strategies for nucleic acid detection, whereby the signal would increase or decrease following attachment of the dye to the detector species. Generally, when a fluorometric approach is used a number of different detector devices can be used to record the generation of fluorescent signal, such as for example CCD cameras, fluorescence scanners, fluorescence based microplate readers or fluorescence microscopes.

In a further embodiment the moiety that permits the detection of the first oligonucleotide probe is an enzyme that yields a detectable signal, such as a colorimetric or fluorometric signal, following contact with a substrate. It will be apparent to a skilled person that a number of enzyme substrate systems are available and routinely used in the field of diagnostics, such as in ELISA and Immunohistochemistry detection. Horseradish peroxidase (HRP) is one example. Utilising an enzyme attached to the first oligonucleotide probe for detection of the detector species in step c), offers a number of potential advantages, such as enhanced sensitivity of detection and increased control of signal development through a separate step involving addition of substrate. Other suitable colorimetric enzymes might include: glycosyl hydrolases, peptidases or amylases, esterases (e.g. carboxyesterase), glycosidases (e.g. galactosidase), and phosphatases (e g alkaline phosphatase). This list should not be considered in any way limiting.

In another approach, the presence of the detector species in step c) is detected electrically, such as by a change in impedence or a change in conductimetric, amperometric, voltammetric or potentiometric signal, in the presence of the detector species. Thus in an embodiment the detector species is detected by a change in electrical signal. The electrical signal change may be facilitated by the moiety that permits the detection of the first oligonucleotide probe, such as a chemical group that leads to an enhanced change in electrical signal Since electrical signal detection can be so sensitive said detection moiety may be simply an oligonucleotide sequence, although in certain embodiments signal is enhanced by the presence of chemical groups known to enhance electrical signals, such as metals e.g. gold and carbon.

Whilst in an embodiment the electrical signal change resulting from accumulation of the detector species may be detected in an aqueous reaction during amplification, in other embodiments the electrical signal detection is facilitated by the localisation of the detector species to a particular site for its detection, such as the surface of an electrochemical probe, wherein said localisation is mediated by the second oligonucleotide probe.

Other techniques that are routinely employed for the detection of nucleic acids such as the detector species and may also be employed for detection in the method include: mass spectrometry (such as MALDI or LC-TOF), luminescence spectroscopy or spectrometry, fluorescence spectroscopy or spectrometry, liquid chromatography and fluorescence polarization.

In an embodiment, step c) produces a colorimetric or electrochemical signal using carbon or gold, preferably carbon.

In an embodiment the detector species is detected by nucleic acid lateral flow. Nucleic acid lateral flow, wherein nucleic acids are separated from other reaction components by their diffusion through a membrane, typically made of nitrocellulose, is a rapid and low-cost method of detection capable of coupling with a range of signal read-outs, including colorimetric, fluorometric and electrical signals. Nucleic acid lateral flow is well suited for use in the detection of the detector species in the method and offers a number of advantages. In an embodiment the nucleic acid lateral flow detection is performed wherein the first oligonucleotide probe within the detector species is used to attach a colorimetric or fluorometric dye and the second oligonucleotide probe within the detector species is used to localise said dye to a defined location on the lateral flow strip. In this way, rapid detection can be performed with results visualised by eye or by a reader instrument. Nucleic acid lateral flow may employ an antigen as the detector moiety in the second oligonucleotide probe with the associated antibody immobilised on the lateral flow strip. Alternatively in the present method sequence specific detection via hybridisation of the pre-detector species or detector species onto the lateral flow strip may be readily performed providing for a simple, low cost alternative to antibody based assays with improved multiplexing potential. Known methods, such as SDA, that do not utilise the two oligonucleotide probes of the present method, typically generate double stranded DNA products which are not available for detection based upon sequence specific hybridisation. In contrast in the present method, the detector species is particularly amenable to multiplex detection, by virtue of the use of location specific hybridisation based detection. Carbon or gold nanoparticles may be readily employed in nucleic acid lateral flow. Localisation of the detector species causes local concentration of carbon or gold, causing appearance of a black or red colour, respectively. In an embodiment the first oligonucleotide probe contains a moiety, such as a biotin, that permits its binding to a colorimetric dye prior to localisation on the strip by sequence specific hybridisation.

The spatial positioning of the detector species is closely associated with the technique employed for detection of the detector species, as it permits, for example, the hybridisation based binding of the detector species at a particular location. In addition to facilitating rapid and specific detection, such physical attachment can enhance the use of the method in the multiplex detection of multiple different target nucleic acids.

In an embodiment the second oligonucleotide probe is attached on a nucleic acid lateral flow strip or on the surface of an electrochemical probe, a 96-well plate, beads or an array surface. Thus the at least one species within the amplification product becomes localised to the physical location of the second oligonucleotide probe which is readily detected following the formation of the detector species at such location. Alternatively, it can be advantageous to use a single stranded oligonucleotide as the moiety attached to the second oligonucleotide probe that permits its attachment to a solid material. In this way the sequence of the solid phase attached oligonucleotide can be defined independently to the target nucleic acid sequence to enhance the efficiency of binding. Thus, in an embodiment the moiety that permits the attachment of the second oligonucleotide probe to a solid material is a single stranded oligonucleotide. Said single stranded oligonucleotide can be designed to have improved affinity and efficiency of hybridisation to enhance performance of the method. For example, in certain embodiments of the method rather than attaching the second oligonucleotide probe to the lateral flow strip directly, a separate oligonucleotide with a sequence optimised for on-strip hybridisation is employed that is capable of efficient hybridisation to the single stranded oligonucleotide moiety present within the second oligonucleotide probe.

In various investigations we have significantly enhanced performance of the method by nucleic acid lateral flow using a single stranded oligonucleotide as the attachment moiety of the second oligonucleotide probe, which provides for the on-strip hybridisation sequence to be enhanced. For example, a G-C rich sequence may be employed for the on-strip hybridisation, or a longer sequence with higher Tm may be employed, that supplements the length of the second oligonucleotide probe. Alternative, said single stranded oligonucleotide moiety may comprise one or more modified base or internucleotide linkage to enhance its affinity, such as a PNA, LNA or G-clamp. We have observed that when a repeating sequence motif is employed in the single stranded oligonucleotide moiety, a surprising enhancement of the hybridisation efficiency is observed which is not predicted by its predicted Tm. Thus in an embodiment the sequence of the single stranded oligonucleotide moiety comprises three or more repeat copies of a 2 to 4 base DNA sequence motif. For example, in various investigations employing such a sequence motif we have observed a substantial enhancement in the sensitivity of detection by nucleic acid lateral flow, frequently with a signal enhancement of 100-fold or more.

Thus in an embodiment wherein the presence of the detector species is detected by nucleic acid lateral flow, the nucleic acid lateral flow utilises one or more nucleic acids that is capable of sequence specific hybridisation to the moiety that permits the attachment of the second oligonucleotide probe to a solid material.

A further advantage is conferred by de-coupling the target nucleic acid sequence from the solid material for attachment or from the means of detection, this may be permitted by the use of the single stranded oligonucleotide as the detection moiety within the first oligonucleotide probe and/or the attachment moiety with the second oligonucleotide probe. In this way the relevant solid material for attachment, or device containing said solid material, such as the nucleic acid lateral flow strip, and/or the means of detection, can be optimised and defined without regard to the sequence of the target nucleic acid to be detected. Such a "universal" detection apparatus can be used from application to application and target to target without needing to be altered. For example a nucleic acid lateral flow strip with printed lines corresponding to a compatible set of oligonucleotide sequences which have the ability for efficient on-strip hybridisation and no unintended cross-talk can be defined, optimised and efficiently manufactured independently of the development of the oligonucleotide primers and probes of the method for detection of multiple target nucleic acid sequences.

Repeating sequence motifs as described above have also been found to have more general application in the capture and detection of nucleic acids by hybridisation-based binding to a substrate. Duplex, triplet and quadruplet repeats are all suitable for use and lead to highly efficient pull-down of oligonucleotides with appropriate regions of reverse complementarity. Thus there is also provided a substrate for capturing a detector nucleic acid having an immobilised oligonucleotide capture probe comprising a single stranded hybridisation region of at least 8 bases in length which comprises 3 or more repeat copies of a 2 to 4 base DNA sequence motif wherein the copies of the sequence motif are contiguous or separated by one base.

The capture probe may comprise at least 4 or at least 5 repeat copies of the sequence motif. The capture probe may comprise 3 to 100, such as 3 to 50, e.g. 3 to 20, 5 to 14 or 7 to 12, repeat copies of the 2 to 4 base DNA sequence motif. When the sequence motif is a 2 base DNA sequence motif, the capture probe may comprise 4 or more repeat copies of the sequence motif. In one embodiment the repeat copies of the DNA sequence motif are contiguous, i.e. not separated by additional bases.

In one embodiment the sequence motif is a 2 base DNA sequence motif, in a further embodiment it is a 3 base DNA sequence motif, and in a further embodiment it is a 4 base DNA sequence motif.

The single stranded hybridisation region of the capture probe may be at least 10, or at least 12, bases in length.

The capture probe may additionally comprise additional single or double stranded oligonucleotide regions 5' or 3' of the hybridisation region, for example the capture probe may comprise a single or double stranded spacer region between the hybridising region and the substrate. The capture probe may comprise a thymidine region 5' or 3' of the hybridisation region, the thymidine region may be 3 to 20, e.g. 5 to 12, bases in length.

The hybridisation region of the capture probe is capable of hybridisation to the detector nucleic acid.

Examples of sequence motifs which may be present in the capture probes include the following and their reverse complements: AG, AT, CA, AAG, AAT, AGT, CCA, AAT, CCT, CAA, AAC, GAC, AACT, TACC, CAGT, GACT, TAGT, GAGT, AAGT, TCAT, ATCT, TAGA, TACA, CACT, CCAA, CACT and AGAC.

Examples of specific capture probes include the following:

(SEQ ID No. 1)
TTTTTTTTTTAGAGAGAGAGAGAGAGAGAGAG, (SEQ ID No. 2)
TTTTTTTTTTAATAATAATAATAATAATAATAATAATAATAAT, (SEQ ID No. 3)
TTTTTTTTTACCACCACCACCACCACCACCACCACCACCACC,

-continued (SEQ ID No. 4)
TTTTTTTTTTAACTAACTAACTAACTAACTAACTAACTAACT,
and (SEQ ID No. 5)
TTTTTTTTTTGAGTGAGTGAGTGAGTGAGTGAGTGAGTGAGT.

The capture probe may comprise one or more modified base and/or modified internucleotide linkage. Modified bases and modified internucleotide linkages include those mentioned elsewhere in this application.

The substrates may be used for the capture of multiple different detector nucleic acids, thus the substrates may have two or more spatially distinct immobilised capture probes each comprising a different hybridisation region for capturing a different detector nucleic acid.

The substrates may comprise multiple zones, for example the capture probe may be immobilized to a test zone and the substrate may additionally comprise a sample pad and/or conjugate pad upstream of the test zone. The substrate may also comprise a control zone which may be located upstream or downstream of the test zone. When the substrate comprises a conjugate pad this may contain one or more additional reagents, such as an oligonucleotide probe comprising a hybridisation region capable of hybridising to the detector nucleic acid and a single stranded region capable of sequence specific hybridisation to the DNA sequence motif.

The substrates may be any substrate known in the art for the capture of nucleic acids using immobilised hybridisation probes. Such substrates include arrays, microarrays, beads, plates, microfluidic substrates, particular substrates which may be mentioned include lateral flow strips. The substrates may be homogeneous or non-homogeneous in composition and suitable material may be used for the substrates including glass, plastics, synthetic polymers, gold and other metal surfaces, and nitrocellulose membranes.

The capture probes may be immobilized on the substrate by any suitable methodology, e.g. UV cross-linking, adsorption, covalent, hydrophobic or charged based attachment. The capture probes may be immobilised on the substrate via a spacer oligonucleotide 5' or 3' of the hybridising region.

According to a further aspect there is provided an oligonucleotide probe comprising a single stranded hybridisation region of at least 8 bases in length which comprises 3 or more repeat copies of a 2 to 4 base DNA sequence motif wherein the copies of the sequence motif are contiguous or separated by one base. The oligonucleotide may comprise any of the features recited above in reference to the substrates.

According to a further aspect there is provided a method for capturing a detector nucleic acid comprising applying a sample containing the detector nucleic acid to a substrate as defined in any of the embodiments above wherein the detector nucleic acid is captured by hybridisation to the capture probe. The detector nucleic acid may comprise an amplification product produced by an amplification method such as PCR or an isothermal amplification method such as Loop-mediated Isothermal Amplification (LAMP), Helicase-Dependent Amplification (HDA), Recombinase Polymerase Assay (RPA), Transcription-Mediated Amplification (TMA), Nucleic Acid Sequence-Based Amplification (NASBA), Signal mediated amplification of RNA Technology (SMART), Strand Displacement Amplification (SDA), Nicking and Extension Amplification Reaction (NEAR), Rolling Circle Amplification (RCA), Isothermal Multiple Displacement Amplification (IMDA), Single Primer Isothermal Amplification (SPIA), Recombinase Polymerase Assay (RPA), and Self-sustained Sequence Replication (3SR). The isothermal amplification method may utilise a DNA polymerase and one or more restriction enzymes that are not nicking enzymes and be as described in any of the embodiments herein.

The detector nucleic acid may be RNA, DNA or an RNA/DNA hybrid and may be obtained or derived using any of the methods described elsewhere in this application, e.g. from a biological sample. The detector nucleic acid comprises a single stranded region that is capable of hybridisation to the hybridisation region of the capture probe. Thus the detector nucleic acid may comprise a single stranded region that comprises all or part of the reverse complement of the single stranded hybridisation region of the capture probe. In this context it is noted that this single stranded region of the detector nucleic acid whilst being a minimum of 8 bases in length and comprising at least 3 repeat copies of the reverse complement of the 2 to 4 base DNA sequence motif comprised in the capture probe, where the capture probe comprises more than 3 repeat copies of the 2 to 4 base DNA sequence motif, the single stranded region of the detector nucleic acid may comprise fewer copies of the sequence motif. For example, the detector nucleic acid may only comprise 3 to 6, e.g. or 3 or 4, copies of the reverse complement of the sequence motif.

In one embodiment of the method the detector nucleic acid is in the form of a detector species comprising a single stranded nucleic acid, such as a single stranded nucleic acid amplicon, hybridised to one or more oligonucleotide probes such as a probe which is attached to a moiety which permits its detection and/or a probe which comprises the single stranded region capable of sequence specific hybridisation to the hybridisation region of the capture probe. In one embodiment the detector species is a single stranded nucleic acid hybridised to the first oligonucleotide probe which is attached to a moiety that permits its detection and to a second oligonucleotide probe which comprises the single stranded region capable of sequence specific hybridisation to the hybridisation region of the capture probe. In some embodiments the moiety that permits the detection of an oligonucleotide probe is a colorimetric or fluorometric dye or a moiety that is capable of attachment to a colorimetric or fluorometric dye such as biotin. The colorimetric dye may be carbon or gold, preferably carbon, e.g. carbon adsorbed to biotin binding protein.

The method may additionally comprise the step of detecting a captured nucleic acid. Any of the detection means described throughout this application may be used for detection. Detection of the detector nucleic acid may be used for the diagnosis, prognosis or monitoring of a disease, e.g. an infectious disease, or a diseased state.

The substrates described above may be contained on a device, for example a diagnostic device such as a single-use diagnostic device. The device may also be suitable for performing the capture method as described above and additionally detecting the captured detector nucleic acid. Thus according to a further aspect there is provided a device comprising a substrate as described above and means to enable the detector nucleic acid to be applied to the substrate.

It is to be understood that all the aspects and optional and/or preferred embodiments of the invention described herein in relation to the methods for the detection of nucleic acids of defined sequence and kits and devices for use in said methods also apply in relation to the repeating sequence motif aspects of the invention and vice versa.

In a number of embodiments the detection method of the present invention may be performed in a quantitative manner Thus, the level of the single stranded target nucleic acid in the sample may be quantified in step c). Quantification may be accomplished e.g. by measuring the detector species colorimetrically, fluorometrically or electrically, during the time course of the reaction at multiple time-points rather than at a single end-point. Alternative strategies for quantification include sequential dilution of the sample, analogous to droplet digital PCR. In a further embodiment the level of the single stranded target nucleic acid in the sample may be determined semi-quantitatively. For example, where the intensity of a colorimetric signal on a nucleic acid lateral flow strip would correspond to the approximate level of the single stranded target nucleic acid in the sample. Alternatively an inhibitor may be used whereby the number of copies of the single stranded nucleic acid target must exceed a certain defined number of copies in order to overcome the inhibitor and produce a detectable number of copies of the detector species.

In the method of the invention the second oligonucleotide probe is attached to a solid material or to a moiety that permits its attachment to a solid material. Optionally, in embodiments, one or more of the other oligonucleotide primers and probes may also be attached to a solid material or to a moiety that permits their attachment to a solid material. It will be apparent to a skilled individual that attachment of oligonucleotides to a solid material may be accomplished in a variety of different ways. For example, a number of different solid materials are available which have or can be attached or functionalised with a sufficient density of functional groups in order to be useful for the purpose of attaching or reacting with appropriately modified oligonucleotide probes. Further, a wide range of shapes, sizes and forms of such solid materials are available, including beads, resins, surface-coated plates, slides and capillaries. Examples of such solid materials used for covalent attachment of oligonucleotides include, without limitation: glass slides, glass beads, ferrite core polymer-coated magnetic microbeads, silica micro-particles or magnetic silica micro-particles, silica-based capillary microtubes, 3D-reactive polymer slides, microplate wells, polystyrene beads, poly (lactic) acid (PLA) particles, poly(methyl methacrylate) (PMMA) micro-particles, controlled pore glass resins, graphene oxide surfaces and functionalised agarose or poly-acrylamide surfaces. Polymers such as polyacrylamide have the further advantage that a functionalised oligonucleotide can be covalently attached during the polymerisation reaction between monomers (e.g. acrylamide monomers) that is used to produce the polymer. A functionalised oligonucleotide is included in the polymerisation reaction to produce a solid polymer containing covalently attached oligonucleotide. Such polymerisation represents a highly efficient means of attaching oligonucleotide to a solid material with control over the size, shape and form of the oligonucleotide-attached solid material produced.

Typically in order to attach an oligonucleotide probe to any such solid materials, the oligonucleotide is synthesised with a functional group at either the 3' or 5' end; although functional groups may also be added during the oligonucleotide production process at almost any base position. A specific reaction may then be performed between the functional group(s) within an oligonucleotide and a functional group on the relevant solid material to form a stable covalent bond, resulting in an oligonucleotide attached to a solid material. Typically such an oligonucleotide would be attached to the solid material by either the 5' or 3' end. By way of example, two commonly used and reliable attachment chemistries utilise a thiol (SH) or amine ($NH_3$) group and the functional group in the oligonucleotide. A thiol group can react with a maleimide moiety on the solid support to form a thioester linkage, while an amine can react with a succinimidyl ester (NHS ester) modified carboxylic acid to form an amide linkage. A number of other chemistries can also be used. As well as chemical conjugation of an oligonucleotide probe to a solid material, it is possible and potentially advantageous to directly synthesise oligonucleotide probes on a solid material for use in the performance of the method.

In other embodiments the second oligonucleotide probe is attached to a moiety that permits its attachment to a solid material. One strategy is to employ a method of affinity binding whereby a moiety that permits specific binding may be attached to the oligonucleotide probe to facilitate its attachment to the relevant affinity ligand. This may be performed, for example, using antibody-antigen binding or an affinity tag, such as a poly-histidine tag, or by using nucleic acid based hybridisation wherein the complementary nucleic acid is attached to a solid material, e.g. a nitrocellulose nucleic acid lateral flow strip. An exemplary such moiety is biotin, which is capable of high affinity binding to streptavidin or avidin which itself is attached to beads or another solid surface.

The presence of two or more different target nucleic acids of defined sequence may be detected in the same sample. In an embodiment of the method, separate series of steps a), b), and c), using different oligonucleotide primers and oligonucleotide probes for each of the two or more target nucleic acids is performed, which separate steps may be conducted simultaneously. For example, in an embodiment, one set of oligonucleotide primers and oligonucleotide probes would be used for the detection of one target nucleic acid in a sample and another set of oligonucleotide primers and oligonucleotide probes would be used for the detection of another target nucleic acid in the same sample. The detection of the detector species produced from the two or more different sets of primers/probes could each be coupled to a particular signal, such as different colorimetric or fluorometric dyes or enzymes, to allow multiplex detection. Alternatively multiplex detection may be accomplished by the attachment of the second oligonucleotide probe to a solid material, directly or indirectly through a moiety that permits its attachment to a solid material. Such an approach utilises physical separation of the detector species produced by the different series of steps a), b) and c), rather than relying on a different detection means. Thus, for example, a single dye could be used on nucleic acid lateral flow to detect multiple different target nucleic acids wherein each different detector species produced is localised to a particular printed line on the lateral flow strip and direct or indirect sequence based hybridisation to the second oligonucleotide probe forms the basis of the differential detection. Alternatively an electrical detection array may be used wherein multiple different second oligonucleotide probes are attached to a particular region of the array and thus in a multiplex reaction wherein multiple different detector species are produced at the same time, each detector species becomes localised via hybridisation to a discrete region of the array permitting multiplex detection.

The foregoing detection processes, such as nucleic acid lateral flow and electrical detection, and their ability to readily detect multiple different target nucleic acids within the same sample, are enabled by the intrinsic requirement of the present method for two oligonucleotide probes. As such they powerfully demonstrate the advantages of the method of the invention over known methods.

The current invention is of broad utility to various fields and applications which require detection of a target nucleic acid of defined sequence in a sample. It represents a fast, cheap and convenient means of determination of the presence of a target nucleic acid sequence within a sample. By way of a list of applications that is in no way limiting, we envisage that the invention could be of value in fields such as; diagnostics, forensics, agriculture, animal health, environment, defence, human genetic testing, prenatal testing, blood contamination screening, pharmacogenomics or pharmacokinetics and microbiological, clinical and biomedical research. Suitably the sample is a biological sample such as a human sample. The sample may be a human sample, a forensic sample, an agricultural sample, a veterinary sample, an environmental sample or a biodefence sample.

Detection of target nucleic acid may be used for the diagnosis, prognosis or monitoring of disease or a diseased state such as an infectious disease, including but not limited to HIV, influenza, RSV, Rhinovirus, norovirus, tuberculosis, HPV, meningitis, hepatitis, MRSA, Ebola, *Clostridium difficile*, Epstein-Barr virus, malaria, plague, polio, chlamydia, herpes, gonorrhoea, measles, mumps, rubella, cholera or smallpox, or cancer, including but not limited to colorectal cancer, lung cancer, breast cancer, pancreatic cancer, prostate cancer, liver cancer, bladder cancer, leukaemia, esophageal cancer, ovarian cancer, kidney cancer, stomach cancer or melanoma, or in the fields of human genetic testing, prenatal testing, blood contamination screening, pharmacogenetics or pharmacokinetics.

The invention is amenable for use with a broad array of sample types, such as, for example: Nasal swabs or aspirates, nasopharyngeal swabs or aspirates, throat swabs or aspirates, cheek swabs or aspirate, blood or a sample derived from blood, urine or a sample derived from urine, sputum or a sample derived from sputum, stool or a sample derived from stool, cerebrospinal fluid (CSF) or a sample derived from CSF, and gastric fluids or a sample derived from gastric fluids, human or animal samples derived from any form of tissue biopsy or bodily fluid. We have also performed the method in a broad range of samples containing at least 10-20% of the following clinical specimens: Nasal swab in VTM, nasopharyngeal swab in VTM, thin prep media, throat swab in liquid Amies, HSV sore swab in M4 media, synovial fluid, sputum processed via 2M NaOH/isopropanol followed by DNA capture beads, rectal swab in TE, stool sample processed by homogenisation and DNA capture beads, CSF, APTIMA swab, amniotic fluid, oral swab in liquid Amies, urine, VRE swab in TE, pleural fluid, whole blood, K2EDTA plasma, L.Heparin plasma and blood serum. These experiments have demonstrated the remarkable versatility of the method to different clinical applications and the lack of inhibition observed in relevant samples. This is in stark contrast to other methods which are inhibited by inhibitors found in biological specimens, such as heparin and phytic acid which inhibit PCR, and therefore demonstrates the potential to use the method in a low-cost or single-use device without any requirement for complex sample preparation procedures.

The target nucleic acid may be (a) viral or derived from viral nucleic acid material (b) bacterial or derived from bacterial nucleic acid material (c) circulating, cell-free DNA released from cancer cells (d) circulating, cell-free DNA released from foetal cells or (e) micro RNA or derived from micro RNA inter alia.

The single stranded target nucleic acid for the method may be naturally occurring or non-naturally occurring. The target nucleic acid may be generated in situ or produced from a naturally occurring nucleic acid prior to performance of the method. A single stranded target nucleic acid for the method may be prepared by one or more additional steps performed prior to or simultaneously with step a), which additional steps may encompass one or more enzymes such as polymerases and restriction enzymes. Generating the target nucleic acid for the method in this way has a number of potential advantages, such as permitting even more highly multiplexed assays and/or overcoming ab initio background. A highly specific conversion of nucleic acid material in a biological sample may, for example, be performed without amplification prior to amplification in step a). The sample may be, for example, treated, purified, subject to buffer exchange, subject to exome capture, partially depleted of contaminating material and/or converted to a single stranded target nucleic acid for the method containing one or more modified dNTP. Provided that the "real" target nucleic acid in the sample to be detected is converted into the "surrogate" target nucleic acid for performance of the method with reliable conversion (which may be <1:1, 1:1 or 1:>1, i.e. possibly with some element of amplification) then detection of the "surrogate" target nucleic acid will allow the "real" nucleic acid to be detected and/or quantified. Furthermore, production of a surrogate target from a naturally occurring target in this way can be used to generate in a specific manner a target nucleic acid for the method with any desired sequence. In an embodiment wherein the single stranded target nucleic acid is derived from double stranded DNA following disassociation of the two strands, e.g. by strand invasion, two complementary single stranded nucleic acid targets are present and may be amplified and detected in a reciprocal process by the same oligonucleotide primers and probes. Wherein the target is the genome of a −ve strand single stranded RNA virus, the +ve strand transcript may also be present in the sample and either strand or both strands may be amplified and detected as the single stranded target nucleic acid in the method using the same oligonucleotide primers and probes.

It is also envisaged that the present invention has the potential to be of utility in screening samples for cell free DNA and epigenetic modifications such as, for example, CpG methylation of DNA sequences. Such epigenetic modification of particular cancer associated target genes can serve as useful biomarkers in a number of diseases and disease states. Given the growing appreciation of the importance of epigenetic modification in human disease, there is potential for the present invention to be used to specifically assess the epigenetic modification of particular target nucleic acid biomarkers based upon the differential activity of the strand displacement DNA polymerase and/or restriction enzymes. Therefore, in an embodiment, the target nucleic acid contains a site of epigenetic modification, such as methylation. Alternatively the "real" nucleic acid used to produce a "surrogate" target nucleic acid for the performance of the method, as described above, contains a site of epigenetic modification.

A further aspect of the invention relates to kits for use in the detection of nucleic acids of defined sequence in a sample. Thus the invention also provides a kit comprising the following:
  a) a first oligonucleotide primer and a second oligonucleotide primer wherein said first primer comprises in the 5' to 3' direction a restriction enzyme recognition sequence and cleavage site and a region that is capable of hybridising to a first hybridisation sequence in a single stranded target nucleic acid of defined sequence, and said second primer comprises in the 5' to 3' direction a restriction enzyme recognition sequence and cleavage site and a region that is capable of hybridising to the reverse complement of a second hybridisation sequence upstream of the first hybridisation sequence in the target nucleic acid;

b) a first restriction enzyme that is not a nicking enzyme and is capable of recognising the recognition sequence of and cleaving the cleavage site of the first primer and a second restriction enzyme that is not a nicking enzyme and is capable of recognising the recognition sequence of and cleaving the cleavage site of the second primer;

c) a strand displacement DNA polymerase;

d) dNTPs;

e) one or more modified dNTP;

f) a first oligonucleotide probe which is capable of hybridising to a first single stranded detection sequence in at least one species in amplification product produced in the presence of said target nucleic acid and which is attached to a moiety which permits its detection; and g) a second oligonucleotide probe which is capable of hybridising to a second single stranded detection sequence upstream or downstream of the first single stranded detection sequence in said at least one species in amplification product and which is attached to a solid material or to a moiety which permits its attachment to a solid material.

In an embodiment one of the first and second oligonucleotide probes of the kit is blocked at the 3' end from extension by the DNA polymerase and is not capable of being cleaved by either the first or second restriction enzymes, for example due to the presence of one or more sequence mismatch and/or one or more modifications such as a phosphorothioate linkage.

In an embodiment one of the first and second oligonucleotide probes of the kit has 5 or more bases of complementarity to the hybridising region or the reverse complement of the hybridising region of the first or second primer.

In another embodiment the first oligonucleotide probe of the kit has some complementarity, e.g. 5 or more bases of complementarity, to the hybridising region of one of the first and second oligonucleotide primers, and/or the second oligonucleotide probe of the kit has some complementarity, e.g. 5 or more bases of complementarity, to the reverse complement of the hybridising region of the other of the first and second oligonucleotide primer.

In further embodiments the first and/or second oligonucleotide probes may have some complementarity or reverse complementarity to the gap between the first and second hybridisation sequences in the target nucleic acid as described above.

The kit may also comprise a reverse transcriptase.

The kit may additionally comprise means to detect the presence of a detector species produced in the presence of the target nucleic acid. For example, the kit may additionally comprise a nucleic acid lateral flow strip, an electrochemical probe a 96-well plate, beads or an array surface, and/or a colorimetric or fluorometric dye and/or a device for the detection of a change in electrical signal, and/or carbon or gold.

In various embodiments the target nucleic acid and the components of the kits, such as, the first oligonucleotide primer and/or the second oligonucleotide primer and/or the first restriction enzyme and/or the second restriction enzyme and/or the DNA polymerase and/or the dNTPs and/or the one or more modified dNTP and/or the first oligonucleotide probe and/or the second oligonucleotide probe and/or the either the first or second single stranded detection sequence in the at least one species within the amplification product comprised in the kit are as defined herein for the methods of the invention. For example, the kit may comprise any combination of the features of such components described herein, such as, without limitation, the following: One of the first and second oligonucleotide probes is blocked at the 3' end from extension by the DNA polymerase and is not capable of being cleavage by either the first or second restriction enzymes optionally due to the presence of one or more sequence mismatch and/or one or more modifications such as a phosphorothioate linkage; the first restriction enzyme and the second restriction enzyme are the same restriction enzyme; the one or more modified dNTP is an alpha thiol modified dNTP; the moiety that permits the detection of the first oligonucleotide probe is a colorimetric or fluorometric dye or a moiety that is capable of attachment to a colorimetric or fluorometric dye, such as biotin; the moiety that permits the attachment of the second oligonucleotide probe to a solid material is a single stranded oligonucleotide, optionally comprising three or more repeat copies of a 2 to 4 based DNA sequence motif; the first and second oligonucleotide primers comprise a stabilising sequence upstream of the restriction enzyme recognition sequence and cleavage site, such as at the 5' end, and e.g. of 5 or 6 bases in length; the hybridising region of the first and/or second oligonucleotide primers is between 6 and 30, e.g. 9 and 16, bases in length; and, the first and second hybridisation sequences in the target nucleic acid are separated by 0 to 15 or 0 to 6 bases, in certain embodiments they are separated by 3 to 15 or by 3 to 6 bases, e.g. 5, 7 or 11 bases, or they are overlapping such as by 1 to 2 bases.

The kits may comprise means to detect the presence of a detector species produced in the presence of the target nucleic acid, such as a nucleic acid lateral flow strip. In a further embodiment, the kit additionally comprises the third and/or fourth oligonucleotide primers as defined herein.

The kits may also include reagents such as reaction buffers, salts e.g. divalent metal ions, additives and excipients.

The kits according to the invention may be provided together with instructions for the performance of the methods according to the invention.

The invention also provides the use of the kits of the invention for the detection of a single stranded target nucleic acid of defined sequence in a sample.

It is to be understood that all the optional and/or preferred embodiments of the invention described herein in relation to the methods of the invention also apply in relation to the kits of the invention and the use thereof, and vice versa.

As mentioned previously the methods and kits of the invention are ideally suited for use in a device, such as a single-use diagnostic device. Thus the invention also provides a device containing a kit as described above, in particular a kit comprising means to detect the presence of a detector species produced in the presence of the target nucleic acid, such as a nucleic acid lateral flow strip. The device may be a powered device, e.g. an electrically powered device, the device may also comprise heating means and may be a self-contained device, i.e. a device that requires no ancillary test instrument.

The method of the invention may also be used independently from the detection step c) for amplifying a nucleic acid signal from a target nucleic acid of defined sequence, such a method may be used, for example, if the amplified signal is to be stored and/or transported for detection of the target nucleic acid at a future date and/or alternative location if required. The amplified signal comprises the pre-detector species or detector species produced through performance of the method. Thus in a further embodiment the invention provides a method of amplifying a nucleic acid signal from a target nucleic acid of defined sequence in a sample comprising steps a) and all or part, e.g. part i. or ii., of step b) of the method of the invention.

The invention also provides the use of the kits of the invention for amplifying a nucleic acid signal from a target nucleic acid of defined sequence as defined above.

It is to be understood that all the optional and/or preferred embodiments of the invention described herein in relation to the methods of the invention for detecting the presence of a target nucleic acid of defined sequence in a sample also apply in relation to the method for amplifying a nucleic acid signal from a target nucleic acid of defined sequence.

The following examples serve to further illustrate various aspects and embodiments of the methods described herein. These examples should not be considered limiting in any way.

EXAMPLES

Materials and Methods
The following materials and methods are used in the examples below unless otherwise indicated.
Oligonucleotides: Except as otherwise indicated custom oligonucleotides were manufactured using the phosphoramidite method by Integrated DNA Technologies.
Nucleic Acid Lateral Flow: Carbon nanoparticles were conjugated via non-covalent adsorption to various biotin-binding proteins, e.g. streptavidin. Typically, a colloidal carbon suspension was prepared in Borate Buffer followed by sonication using a probe sonicator. Carbon was subsequently adsorbed to biotin-binding protein by incubation at room temperature. Carbon was either used directly in the reaction mixtures or applied to glass fibre conjugate pads. Lateral flow strips were constructed by combining a conjugate pad containing lyophilised sugars and additives used to improve visual appearance with a sample pad, nitrocellulose membrane and adsorbent pad (Merck Millipore) following the manufacturer's guidelines. Prior to its use in lateral flow strips, the relevant oligonucleotide(s) containing the reverse complement of the sequence to be detected in the method were printed onto the nitrocellulose membrane at a defined location and attached to the membrane via UV cross-linking Example 1

Performance of the Method Wherein the Second Oligonucleotide Probe is Attached to a Solid Material, a Nitrocellulose Lateral Flow Strip This example demonstrates the performance of the method wherein the second oligonucleotide probe is attached to a solid material, a nitrocellulose lateral flow strip, and the first oligonucleotide probe is not contacted with the sample simultaneously to the performance of the amplification step a).

The first oligonucleotide primer with a total length of 24 bases was designed comprising in the 5' to 3' direction: A stabilising region of 7 bases; the 5 bases of the recognition sequence for a restriction enzyme that is not a nicking enzyme; and a 12 base hybridising region comprising the reverse complementary sequence of the first hybridisation sequence in the target nucleic acid. The second oligonucleotide primer was designed to contain the same stabilising region and restriction enzyme recognition sequence, but with the 12 base hybridising region capable of hybridising to the reverse complement of the second hybridisation sequence in the target nucleic acid. In this example the first restriction enzyme and the second restriction enzyme are the same restriction enzyme. The restriction enzyme is an asymmetric double-strand cleaving restriction enzyme with a top strand cleavage site downstream of its 5 base recognition sequence. The first and second hybridisation sequences in the target nucleic acid are separated by 1 base.

The oligonucleotide primers were designed using the target nucleic acid, such that the nucleotide base downstream of the cleavage site in the reverse complement of the primers is Adenosine such that alpha thiol dATP is employed as the modified dNTP in the method. A phosphorothioate modification is inserted by the strand displacement polymerase to block cleavage of said reverse complementary strand.

The first oligonucleotide probe with a total length of 20 bases was designed comprising in the 5' to 3' direction: A 12 base region of complementarity to at least one species in the amplification product; a neutral spacer region of 6 bases; and a 3' biotin modification added during synthesis wherein said biotin modification permits attachment of the first oligonucleotide probe to a colorimetric dye, carbon nanoparticles. Carbon adsorbed to a biotin binding protein was prepared and saturated with the first oligonucleotide probe. The second oligonucleotide probe with a total length of 49 bases was designed to comprise, in the 5' to 3' direction: A neutral spacer comprising 10 X Thymidine bases; 3 X repeats of a 13 base region capable of hybridising to the second single stranded detection sequence downstream of the first single stranded detection sequence in said at least one species in the amplification product. Approximately 30 pmol of said second oligonucleotide probe was printed on the nucleic acid flow strip.

Reactions were prepared containing; 1.6 pmol of the first primer; 0.1 pmol of the second primer; 250 µM 2'-Deoxyadenosine-5'-O-(1-thiotriphosphate) Sp-isomer (Sp-dATP-α-S) from Enzo Life Sciences; 60 µM of each of dTTP, dCTP and dGTP; 2U of the restriction enzyme; and 2U of a *Bacillus* strand displacement DNA polymerase. The nucleic acid target (a single stranded DNA target) was added at various levels (++=1 amol, +=10 zmol, NTC=no target control) in a 10 µl total reaction volume in an appropriate reaction buffer. Reactions were incubated at 45° C. for 7 min or 10 min. 6.5 µl of the terminated reaction mix was then added to 60 µl lateral flow running buffer containing 0.056 mgml$^{-1}$ of the conjugated carbon before being loaded onto the nucleic acid lateral flow strip with the second oligonucleotide probe attached to it in a printed line.

Figure 5:
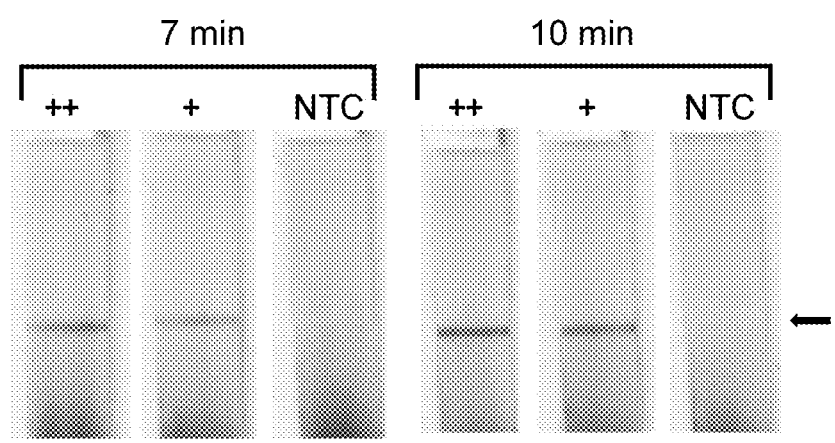
FIG. 5. Performance of the method wherein the second oligonucleotide probe is attached to a solid material, a nitrocellulose lateral flow strip (see Example 1).

FIG. 5 displays a photograph of the lateral flow strips obtained in the performance of the example. An arrow indicates the position where the second oligonucleotide probe has been printed on the nitrocellulose strip and hence where positive signal appears. A clear black line corresponding to the presence of the carbon signal was observed only in the presence of the target nucleic acid at both target levels and at both time points demonstrating the rapid and sensitive detection of the target nucleic acid sequence by the method of the invention.

Example 2

Performance of the Method Wherein the First Oligonucleotide Probe is Blocked at the 3' End From Extension by the DNA Polymerase and is Not Capable of Being Cleaved by Either the First or Second Restriction Enzyme and is Contacted With the Sample in Step a)

This example demonstrates the performance of embodiments of the methods wherein the first oligonucleotide probe is blocked at the 3' end from extension by the DNA polymerase and is not capable of being cleaved by either the first or second restriction enzyme and contacted with the sample simultaneously to the performance of step a). In such embodiments, we have not observed any significant inhibition of the rate of the amplification, indicating that the pre-detector species accumulates in real-time without disrupting the optimal cyclical amplification process. Not only have we not observed any inhibitory effects on the amplification process in said embodiments but we have observed a surprising enhancement of the signal produced corresponding to an increased amount of detector species, of at least 100-fold.

Example 2.1

A variant of the assay used in Example 1 was designed exploiting the embodiment of the method wherein the first oligonucleotide probe is blocked at the 3' end from extension by the DNA polymerase and is not capable of being cleaved by either the first or second restriction enzyme and contacted with the sample simultaneously to the performance of step a). The same oligonucleotide primers, restriction enzyme, dNTPs, modified dNTP and polymerase as employed in Example 1 were used, however, an alternative first oligonucleotide probe was designed with a total length of 21 bases comprising in the 5' to 3' direction: A 5' biotin modification; a neutral region of 8 bases; a 13 base region capable of hybridising to at least one species in the amplification product; and a 3' phosphate modification, wherein the biotin modification permits attachment of the first oligonucleotide probe to a colorimetric dye, carbon nanoparticles, and the phosphate modification blocks its extension by the strand displacement DNA polymerase. Carbon adsorbed to a biotin binding protein was prepared and saturated with the first oligonucleotide probe.

An alternative second oligonucleotide probe was designed with a total length of 51 bases comprising, in the 5' to 3' direction: A 14 base region capable of hybridising to the second single stranded detection sequence upstream of the first single stranded detection sequence in said at least one species in the amplification product; a 6 base neutral spacer sequence; a repeat of the 14 base hybridising region; a second 6 base neutral spacer sequence; and a 10 X Thymidine base spacer. Approximately 30 pmol of said second oligonucleotide probe was printed on the nucleic acid flow strip.

Reactions were prepared containing: 0.8 pmol of the first primer; 0.8 pmol of the second primer; 0.6 pmol of the first oligonucleotide probe; 300 μM Sp-dATP-α-S; 60 μM of each of dTTP, dCTP and dGTP; 2U of the restriction enzyme; and 2U of a *Bacillus* strand displacement DNA polymerase. The nucleic acid target (a single stranded DNA target) was added at various levels (++=1 amol, +=10 zmol, NTC=no target control) in a 10 μl total reaction volume in an appropriate reaction buffer. Reactions were incubated at 45° C. for 6 min. 5 μl of the terminated reaction mix was then added to 60 μl lateral flow running buffer containing 0.03 mgml$^{-1}$ conjugated carbon before being loaded onto the nucleic acid lateral flow strip. A control reaction was performed in order to demonstrate that no detector species is produced where no first oligonucleotide probe was present during the reaction. The equivalent level (0.6 pmol) of the probe was added to said control after step a) in order to control for any unintended impact of the presence of the probe during the lateral flow strip detection.

Figure 6A:
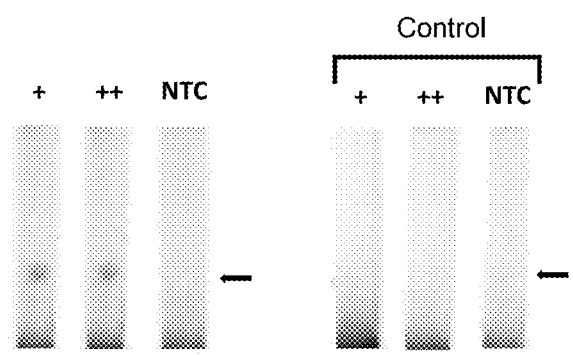
FIGS. 6A and 6B. Performance of the method wherein the first oligonucleotide probe is blocked at the 3' end from extension by the DNA polymerase and is not capable of being cleaved by either the first or second restriction enzyme and is contacted with the sample in step a) (see Example 2).

FIG. 6A presents a photograph of the nucleic acid lateral flow strips following their development. Clear signal corresponding to deposition of the carbon nanoparticles was observed at both target levels when the first oligonucleotide probe was provided during the reaction. As expected, no signal was detected at either target level when the first oligonucleotide was not provided during the reaction. This experiment demonstrates clearly the potential to substantially enhance the production of the detector species in embodiments of the method wherein the first oligonucleotide probe is blocked at the 3' end from extension by the DNA polymerase and is not capable of being cleaved by either the first or second restriction enzyme and contacted with the sample simultaneously to the performance of step a). It is noteworthy that, in contrast to Example 1, an equal concentration of the first and second oligonucleotide primers was provided, which enables more rapid amplification.

Example 2.2

A separate assay was next designed to demonstrate the versatility of the said embodiments of the method with an entirely different target nucleic acid. The oligonucleotide primers and oligonucleotide probes were designed for the relevant target nucleic acid, a single stranded DNA, in a similar manner as described in Examples 1 and 2.1.

Reactions were prepared containing; 0.8 pmol of the first primer; 0.4 pmol of the second primer; 0.6 pmol of the first oligonucleotide probe; 300 μM Sp-dATP-α-S; 60 μM of each of dTTP, dCTP and dGTP; 2U of the restriction enzyme; and 2U of a *Bacillus* strand displacement DNA polymerase. The nucleic acid target (a single stranded DNA target) was added at various levels (+=1 amol, NTC=no target control) in a 10 μl total reaction volume in an appropriate reaction buffer. Reactions were incubated at 45° C. for 6 min. 5 μl of the terminated reaction mix was then added to 60 μl lateral flow running buffer containing 0.08 mgml$^{-1}$ conjugated carbon before being loaded onto the nucleic acid lateral flow strip. A control reaction was performed comprising a truncated variant of the first oligonucleotide probe that was also contacted with the sample simultaneously to the performance of step a).

Figure 6B:
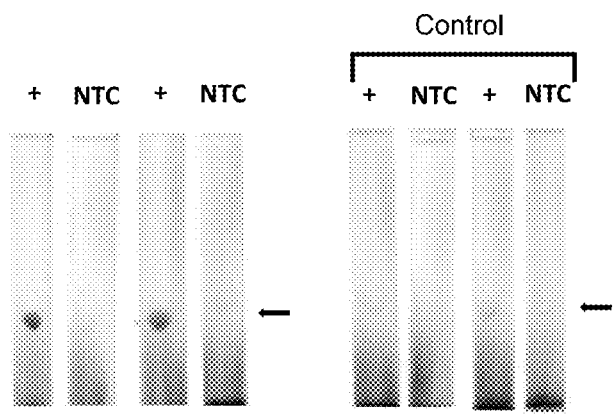

FIG. 6B presents a photograph of the nucleic acid lateral flow strips following their development. Clear positive signal was visible in the present of the target nucleic acid and not in the no target control demonstrating the correct design and functioning of the assay and the robust potential of the embodiments of the method wherein the first oligonucleotide probe is blocked at the 3' end from extension by the DNA polymerase and is not capable of being cleaved by either the first or second restriction enzyme and contacted with the sample simultaneously to the performance of step a). As expected only a very minimal signal was observed in the control assay employing a truncated form of the first oligonucleotide probe, demonstrating the requirement for correct hybridisation of the first oligonucleotide probe simultaneously to the performance of the amplification in step a) for the efficient production of the detector species.

Example 3

Performance of the Method Wherein the Presence of Two or More Different Target Nucleic Acids of Defined Sequence are Detected in the Same Sample This example demonstrates the potential of the method for the detection of two or more different target nucleic acids of defined sequence in a sample. The use of two oligonucleotide probes in addition to the primers in the method, provides an integral approach for detection of the amplification product in the method that is ideally suited to the detection of two or more different target nucleic acids in the same sample. In this example the ability to differentially detect alternative detector species based on the sequence specific hybridisation of the second oligonucleotide probe is demonstrated.

Firstly, in order to demonstrate the ability of the method to be employed for the detection of two or more different target nucleic acids we developed compatible sets of oligonucleotide primers and probes for detection of two distinct targets (A and B). In each case the first oligonucleotide probe was designed to contain the following features in the 5'-3' direction: a 5' Biotin modification, a 7 base stabilising region, the 5 bases of a restriction endonuclease recognition site, a 11-13 base region complementary to the 3' end of the target A or B comprising a phosphorothioate bond at the cleavage site for the restriction enzyme, and a 3' phosphate modification. The second oligonucleotide probes were designed to contain in the 5'-3' direction: A 12-14 base region complementary to the 5' end of the target A or B, a neutral spacer of 5 X Thymidine bases, and a single stranded oligonucleotide moiety of 12 bases as the moiety permitting the attachment of the second oligonucleotide probe to a solid material. The sequence of the single stranded oligonucleotide attachment moiety for each target was designed using a different sequence in order to permit the attachment of each detector species to a different location on the lateral flow strip. Nucleic acid lateral flow strips were prepared containing discrete spots of 30 pmol of an oligonucleotide containing the reverse complementary sequence to each single stranded oligonucleotide detection moiety at separate locations.

Reactions were assembled containing: 0 5 pmol of the first oligonucleotide probe for target A and target B; 0.5 pmol of the second oligonucleotide primer for target A and B, in 65 µl of an appropriate buffer containing 0.032 mgml$^{-1}$ carbon adsorbed to a biotin binding protein. Different levels of each target (+=0.1 pmol; ++=1 pmol) were added to separate reactions individually and both targets were added together. A no target control (NTC) was also performed.

Figure 7A:
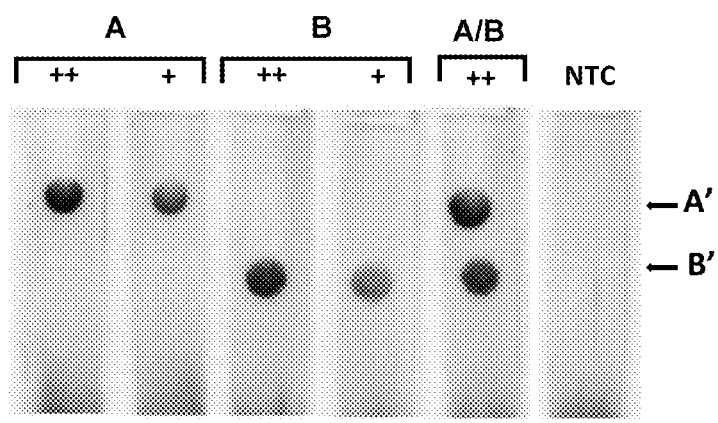
FIGS. 7A, 7B, 7C and 7D. Performance of the method wherein the presence of two of more different target nucleic acids of defined sequence are detected in the same sample (see Example 3).

FIG. 7A displays a photograph of the lateral flow strips obtained in the experiment. Clear black spots corresponding to the deposition of the carbon containing detector species were observed at both target levels and for both assays. Furthermore when both reactions were performed at the same time, the signal corresponding to both targets A and B was observed. No background signal or cross-talk between the different assays was observed.

Figure 7B:
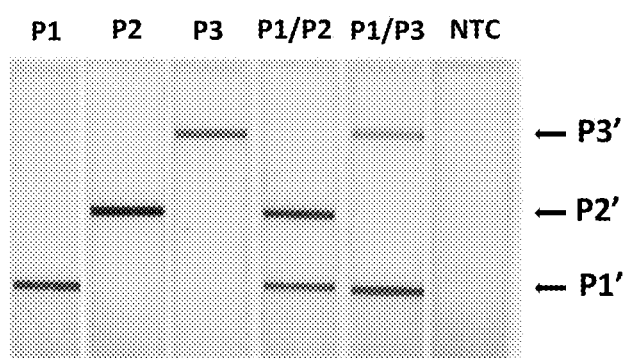
Figure 7C:
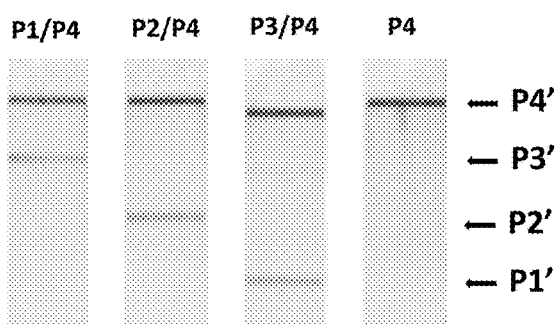
Figure 7D:
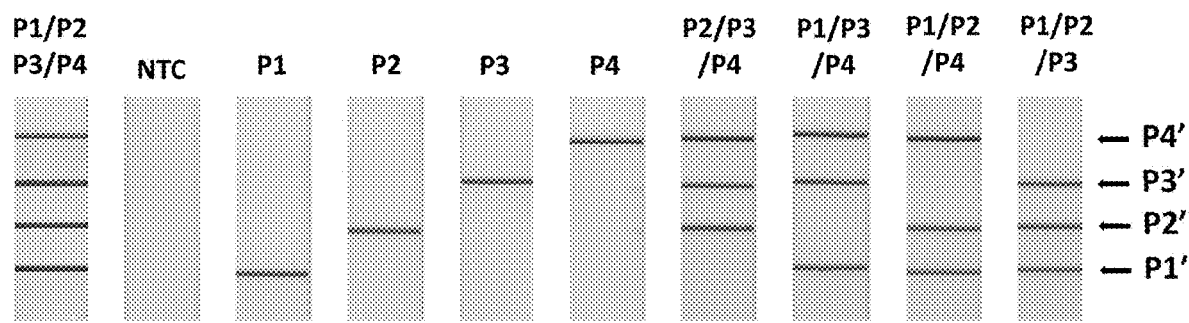

In order to demonstrate the robustness of the method, a further experiment went on to develop three separate assays to demonstrate the potential of the method for the detection of three different target nucleic acids of defined sequence in a sample. A similar methodology was employed as described above. FIG. 7B displays a photograph of the lateral flow strips obtained. The targets P1, P2 and P3 were added individually and in various combinations as indicated. The reverse complement to the single stranded oligonucleotide detection moiety of the second oligonucleotide probe was printed on the nucleic acid lateral flow strip in separate lines. In this experiment the single stranded oligonucleotide detection moiety was designed to contain repeating sequences in order to enhance the performance of the lateral flow detection (see Example 6). The second oligonucleotide probes comprised 4 copies of triplet sequence motifs (P1=ACT; P2=GGT; P3=CTT) and the capture probes on the lateral flow test strip comprised 10-12 copies of the reverse complement of the corresponding sequence motifs (P1=AGT; P2=ACC; P3=AAG). The black signal indicates the deposition of the carbon attached detector species localised to the expected location in all cases for rapid sensitive detection with no unintended cross-talk between the assay nor any background signal. An equivalent experiment comprising four separate assays demonstrates the potential of the method for the detection of four different target nucleic acids (P1, P2, P3 and P4) of defined sequence in a sample with the results displayed in FIG. 7C. In this four-target experiment, P4 was present in all reactions as a positive control and the other targets were added individually to separate reactions. The photographs of the lateral flow strips displayed reveal clear black bands at the expected locations, corresponding to the presence of the relevant detector species bound to carbon. Such multiplex assays demonstrate the potential of the method to be used for diagnostic tests for diseases that are caused by a number of different pathogens wherein detecting the presence of the detector species of the control assay indicates that the method has been performed successfully and the visualisation of one or more of the other detector species on the lateral flow strip indicates the presence of the relevant causative pathogen(s) in an appropriate clinical specimen. Whilst it would be rare in such diagnostic applications, such as in the field of infectious diseases, to observe co-infections wherein more than one pathogen is present at the same specimen, the method of the invention is highly versatile for any combination of the targets in a multiplex reaction to be detected. FIG. 7D, displays the results of an experiment wherein different combinations of four targets (P1, P2, P3 and P4) are added. The ability to detect each target individually and the detect the other three targets when each target is omitted without non-specific background demonstrates the remarkable specificity of detection of the method of the invention.

In the above described and various other experiments, we have also performed multiplex assays for the detection of 3-5 targets at very low target concentrations, e.g. 1 zmol (600 copies) or 17 ymol (10 copies). In this example, we have clearly demonstrated the potential of the method to detect the presence of two or more different target nucleic acids of defined sequence in a sample, and its potential for rapid, low-cost signal detection, e.g. by nucleic acid lateral flow. It is an unusual and advantageous feature of the method of the invention that two or more different target nucleic acids of defined sequence can be readily detected in the same sample. For each additional target to be detected, an additional set of oligonucleotide primers is required, which in prior art methods without temperature cycling presents a significant challenge to detecting the presence of two or more different target nucleic acids, because the additional primers lead to an increased propensity to form non-specific amplification products. In the method of the invention, this challenge is overcome by specificity enhancement, such as that resulting from the use of modified bases, improved enzyme selection and the formation of a detector species using the oligonucleotide probes that exploit additional sequence specific hybridisation events.

Example 4

Performance of the Method Wherein the First and Second Hybridisation Sequences in the Target Nucleic Acid are Separated by 5 Bases This example demonstrates the performance of the method wherein the first and second hybridisation sequences in the target nucleic acid are separated by 5 bases. The ability to use the target derived sequence that is not present in the oligonucleotide primers and is only produced in the amplification product in a target dependent manner when the two oligonucleotide primers are designed to have a gap between the first and second hybridisation sequences, provides the potential for enhanced specificity in embodiments of the method that can overcome any background signal arising from ab initio synthesis or primer-primer binding. In said embodiments the sequence specific hybridisation of the first or second oligonucleotide probe is designed to exploit the gap between the two hybridisation regions in order that the detector species is only produced when the amplification product contains the correct target derived sequence.

In this example we designed a range of assays to demonstrate the hybridisation of the second oligonucleotide probe to various different amplification products that differ only in the sequence of the gap between the first and second hybridisation sequences within the target nucleic acid. The second oligonucleotide probe was designed to contain an 11 base hybridising region for the at least one species in the amplification product at its 5' end. Said region was made up of a 7 base sequence that is the reverse complementary sequence of the first oligonucleotide primer and a 5 base sequence that is reverse complementary sequence to additional target derived sequence in the amplification product derived from the gap between the two primers. The second oligonucleotide probe also contained in the 5' to 3' direction a neutral spacer of 5 X thymidine bases and a 12 base single stranded oligonucleotide moiety for its attachment to a solid material. A nitrocellulose nucleic acid flow strip printed with 30 pmol of an oligonucleotide with the reverse complementarity sequence of said moiety was prepared. The first oligonucleotide probe was designed to contain the same sequence as the second oligonucleotide primer but with a 5' biotin modification, a 3' phosphate modification and a phosphorothioate internucleotide linkage at the position of the restriction enzyme cleavage site.

Four different artificial target nucleic acid sequences (T1, T2, T3 and T4) were designed, each of which had the exact sequence corresponding to the first and second hybridisation sequences, but which differed in the five bases between the first and second hybridisation sequences: T1 contains the correct bases for detection with full complementarity to the 11 base hybridising region of the second oligonucleotide probe; T2 contains four mismatches out of the five bases of the gap; T3 was designed so that four bases out of the five bases of the gap are removed and therefore the species of the amplification product are four bases shorter. T4 contains two mismatches out of the five bases of the gap.

Reactions were assembled containing: 3.6 pmol of the first oligonucleotide primer; 1.8 pmol of the second oligonucleotide primer; 2.4 pmol of the first oligonucleotide probe; 300 µM Sp-dATP-α-S, 60 µM dTTP, dCTP, dGTP; 12U Restriction enzyme; 12U of a *Bacillus* strand displacement DNA polymerase in a total reaction volume of 60 µl in an appropriate reaction buffer. 1 amol target (T1, T2, T3 or T4) was added to each reaction before incubation at 45° C. for 6.5 min before 53.5 µl of the 60 µl reaction was run on the lateral flow strip. Prior to application of the reaction to the lateral flow strip, 1.5 pmol of the second oligonucleotide probe and 2 µg carbon adsorbed to biotin binding protein were deposited onto the conjugate pad and left to dry for 5 min.

FIG. 8 displays a photograph of the nucleic acid lateral flow strips obtained in the experiment. The strip obtained with target T1 shows a clear black line corresponding to carbon attached detector species attached to the solid material of the nitrocellulose and evidencing that the assay developed in this example including the oligonucleotide primers and probes functions correctly and has the potential for rapid and sensitive detection. Reactions performed with targets T2 and T3 did not reveal any carbon corresponding to positive signal, evidencing that both four mismatches and the removal of four bases removes the ability for the second oligonucleotide to hybridise effectively to the pre-detector species produced in the reaction. A very faint signal was observed on the strip produced using T4 indicating that the presence of only two mismatch bases leads to a substantial loss in the ability of the second oligonucleotide probe to successfully hybridise to the pre-detector species to product the detector species capable of binding to the line on the strip. Polyacrylamide gel electrophoresis was performed using repeat reactions to confirm that all reactions with all targets functioned correctly and produced a significant amount of amplification product. An expected a size shift was visible in the reaction performed with the four base truncated target T3.

This example demonstrates how the first and second oligonucleotide probes, an integral feature of the present invention, provide not only for the rapid and sensitive detection of the amplification product, but can also be used to provide a further target sequence based specificity check on the amplification product beyond that resulting from primer hybridisation alone. This powerful technique overcomes the known problems of prior art methods resulting from non-target specific background amplification in certain assays resulting from ab initio synthesis or primer-primer binding. It demonstrates the method of the invention exhibits enhanced specificity compared to prior art methods, whilst retaining sensitive detection and rapid, low-cost results visualisation.

Example 5

Performance of the Method Wherein the Moiety That Permits the Attachment of the Second Oligonucleotide Probe to a Solid Material is an Antigen and the Corresponding Antibody is Attached to a Solid Surface, a Nitrocellulose Lateral Flow Strip In the method of the invention, a number of different moieties may be employed as the moiety for the attachment of the second oligonucleotide probe to a solid material. This example demonstrates that the method can be performed wherein the moiety that permits the attachment of the second oligonucleotide probe to a solid material is an antigen and the corresponding antibody is attached to a solid surface, a nitrocellulose lateral flow strip.

A second oligonucleotide probe was designed to comprise a 32 base sequence comprising a region of homology to at least one species in an amplification product and a 3' Digoxigenin NHS Ester modification which was added during synthesis. A Fab fragment anti-digoxigenin antibody purified from sheep (Sigma-Aldrich) was immobilised onto a nucleic acid lateral flow strip by spotting and air drying.

The performance of the second oligonucleotide probe was demonstrated in an experiment wherein various levels of the target (+++=1 pmol; ++=0.1 pmol; +=10 fmol; NTC=no target control) were added to 60 µl of a contrived reaction buffer containing the necessary reagents for detection using a carbon nucleic acid lateral flow reaction, including 0.016 mgml$^{-1}$ of carbon adsorbed to biotin binding protein. The strip was prepared with 0.5 µg of anti-digoxigenin Fab fragment spotted onto the strip in 0.2 µl buffer containing 2.5 mM Borate and 0.5% Tween 20. The solution was allowed to dry into the nitrocellulose membrane of the lateral flow strip for 2 h. Reactions were incubated at 45° C. for 2 min to form the contrived detector species before the entire reaction mix of each reaction was applied to a lateral flow strip.

Figure 9:
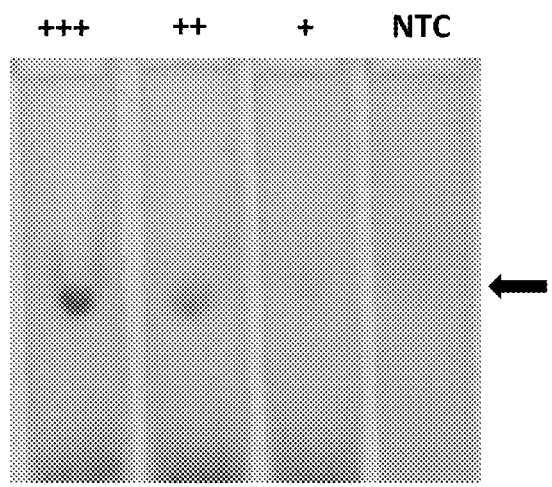
FIG. 9. Performance of the method wherein the moiety that permits the attachment of the second oligonucleotide probe to a solid material is an antigen and the corresponding antibody is attached to a solid surface, a nitrocellulose lateral flow strip (see Example 5).

FIG. 9 displays a photograph of the lateral flow strips produced in the experiment. Black spots corresponding to the deposition of carbon on the lateral flow strip are visible at each target level and not visible in the NTC indicating the specific detection of the detector species. A combination of a biotin based affinity interaction for attachment of the detection moiety (carbon) and an antibody based affinity interaction for solid material attachment moiety has been demonstrated. This example serves to demonstrate the versatility of the method in terms of different approaches available for the attachment of the second oligonucleotide probe to a solid material.

Example 6

Performance of the Method Wherein the Moiety That Permits the Attachment of the Second Oligonucleotide Probe to a Solid Material is a Single Stranded Oligonucleotide Comprising Four Repeat Copies of a Three Base DNA Sequence Motif and the Reverse Complement of Said Single Stranded Oligonucleotide Sequence is Attached to a Solid Material, and Demonstration of the Use of Repeating Sequence Motifs to Enhance Hybridisation-Based Detection of Nucleic Acids This example demonstrates the performance of the method wherein the moiety that permits the attachment of the second oligonucleotide probe to a solid material is a single stranded oligonucleotide comprising four repeat copies of a three base DNA sequence motif. As described above, embodiments of the method employing a single stranded oligonucleotide as the detection moiety of the second oligonucleotide probe presents a straightforward and versatile aspect of the method, which facilitates detection by nucleic acid lateral flow and readily enables the detection of multiple different target nucleic acids in the same sample. Further, the single stranded oligonucleotide detection moieties may be defined in advance and optimised for efficient on-strip hybridisation to enhance the sensitivity of detection and provide for efficient scale-up manufacture of the nucleic acid lateral flow strip.

In one aspect of the invention we observed a surprising improvement to the on-strip hybridisation by use of a single stranded oligonucleotide detection moiety comprised of multiple repeat copies of a DNA sequence motif. This example presents the results of multiple side-by-side experiments wherein the performance of an assay with the second oligonucleotide attached directly to the lateral flow strip is substantially enhanced by the use of a single stranded detection moiety comprising four repeat copies of a three base DNA sequence motif and wherein the reverse complement of said single stranded oligonucleotide sequence is attached to the lateral flow strip.

Example 6.1

An assay was designed exploiting the embodiment of the method wherein the first oligonucleotide probe is blocked at the 3' end from extension by the DNA polymerase and is not capable of being cleaved by either the first or second restriction enzyme and contacted with the sample simultaneously to the performance of step a). A first oligonucleotide probe was designed with a total length of 25 bases comprising in the 5' to 3' direction: A 5' Biotin modification; a neutral region of 7 bases; the 5 bases of a restriction enzyme recognition site that is not a nicking enzyme; a 13 base region capable of hybridising to the first hybridisation region in the target comprising a phosphorothioate bond at the cleavage site for the restriction enzyme; and a 3' phosphate modification, wherein the biotin modification permits attachment of the first oligonucleotide probe to a colorimetric dye, carbon nanoparticles, and the phosphate modification blocks its extension by the strand displacement DNA polymerase.

Two alternative second oligonucleotide probes were designed to detect the same target species (I and II). The second oligonucleotide probe 'I' was designed to contain in the 5' to 3' direction: 3 X repeats of a 14 base region capable of hybridising to the reverse complement of the second hybridisation sequence in the target; and a 9 X Thymidine base spacer. Nucleic acid lateral flow strips were prepared with spots containing 30 pmol of the probe.

The alternative second oligonucleotide probe 'II' was designed to contain in the 5'-3' direction: A 14 base region capable of hybridising to the reverse complement of the second hybridisation region in the target; a neutral spacer of 5 X Thymidine bases; and a single stranded oligonucleotide moiety of 12 bases comprising 4 X repeat of a 3 base sequence motif (GGT) which acts as the moiety permitting the attachment of the second oligonucleotide probe to a solid material. An additional single stranded oligonucleotide was designed comprising in the 5' to 3' direction: an 11 X Thymidine base spacer; a 36 base region comprising a 12 X repeat of the reverse complement to the 3 base sequence motif (ACC) which forms the moiety permitting attachment of the second oligonucleotide II to a solid material. For the second oligonucleotide probe II nucleic acid lateral flow strips were prepared spotted with 30 pmol of said additional single stranded oligonucleotide.

Reactions to test the performance of the oligonucleotide probes I and II were performed containing: 0.5 pmol of the first oligonucleotide probe in 60 µl of an appropriate buffer containing 0.016 mgml−1 carbon adsorbed to biotin binding protein. Reactions for II were assembled in the same manner but with the addition of 0.5 pmol of the second oligonucleotide probe II. The nucleic acid target (a single stranded DNA target representative of at least one species within the amplification product resulting from the designed assay reagents) was added at various levels (+++=1 pmol, ++=0.1 pmol, NTC=no target control). Assembled reactions were incubated for 2 min at 45° C. before the entire reaction mix was loaded onto the appropriate nucleic acid lateral flow strip.

Figure 10A:
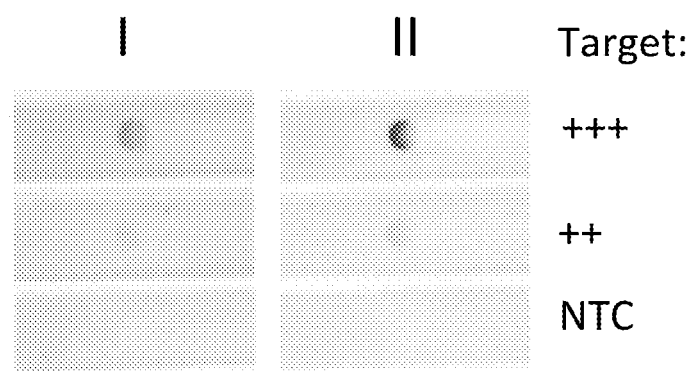
FIGS. 10A and 10B. Performance of the method wherein the moiety that permits the attachment of the second oligonucleotide probe to a solid material is a single stranded oligonucleotide comprising four repeat copies of a three base DNA sequence motif and the reverse complement of said single stranded oligonucleotide sequence is attached to a solid material (see Example 6).

FIG. 10A displays a photograph of the lateral flow strips obtained in the experiment, with the left panel displaying results with second oligonucleotide probe I and the right panel displaying results with second oligonucleotide probe II. Black spots corresponding to the deposition of carbon attached detector species were visualised in the presence of target. For the second oligonucleotide probe II comprising the repeat sequence motif a stronger signal was observed at all target levels.

Example 6.2

Figure 10B:
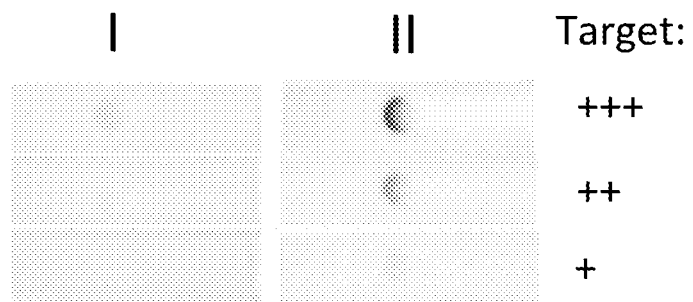

A separate assay was next designed for an entirely different target nucleic acid to demonstrate the versatility of the said embodiments of the method and its broad applicability. The oligonucleotide probes were designed for the relevant target nucleic acid, a single stranded DNA, in a similar manner to that described in Example 6.1; again with two versions of the second oligonucleotide probe referred to as 'I' and 'II' and various target levels (+++=1 pmol, ++=0.1 pmol, +=0.001 pmol). An even more striking effect was observed as displayed in the photograph of the lateral flow strips produced displayed in FIG. 10B. At the lower two target levels tested the second oligonucleotide probe I did not produce any signal whereas the corresponding repeat sequence oligonucleotide probe II produced a clear positive signal indicated by the black spots of deposited carbon.

Example 6.3

A separate experiment was performed to further evidence and explore the remarkable enhancement in binding efficiency that occurs as a result of the use of repeating sequences within the capture probe printed on the nucleic acid lateral flow test strip and to explore the parameters of the repeating sequence. A comparison of capture probes having repeat sequence motifs with capture probes having non-repeat sequences was performed. Nucleic acid lateral flow test strips were constructed as described above by spotting 0.3 µl of a 250 µM solution of one of the following 11 different capture probes (see below) onto the nitrocellulose prior to UV cross-linking.

1.
(SEQ ID No. 1)
TTTTTTTTTTAGAGAGAGAGAGAGAGAGAGAG 2.
(SEQ ID No. 2)
TTTTTTTTTTAATAATAATAATAATAATAATAATAATAATAAT 3.
(SEQ ID No. 3)
TTTTTTTTTACCACCACCACCACCACCACCACCACCACCACC 4.
(SEQ ID No. 4)
TTTTTTTTTTAACTAACTAACTAACTAACTAACTAACTAACT 5.
(SEQ ID No. 5)
TTTTTTTTTTGAGTGAGTGAGTGAGTGAGTGAGTGAGTGAGT 6.
(SEQ ID No. 6)
TTTTTTTTTTGTCGACTCGGAGTCGACTCGGAGTCGACTCGGA 7.
(SEQ ID No. 7)
TTTTTTTTTTGGATATCCCGTGGATATCCCGTGGATATCCCGT 8.
(SEQ ID No. 8)
TTTTTTTTTTGCCATCACGTGCCATCACGTGCCATCACG 9.
(SEQ ID No. 9)
TTTTTTTTTTCAGTTGCGTGAACAGTTGCGTGAACAGTTGCGTGAA 10.
(SEQ ID No. 10)
TTTTTTTTTTCGCTGTATTCACGCTGTATTCACGCTGTATTCA 11.
(SEQ ID No. 11)
TTTTTTTTTTTAACAGTATGGAAATAACAGTATGGAAATAACAGTATGGAAA

Figure 10C:
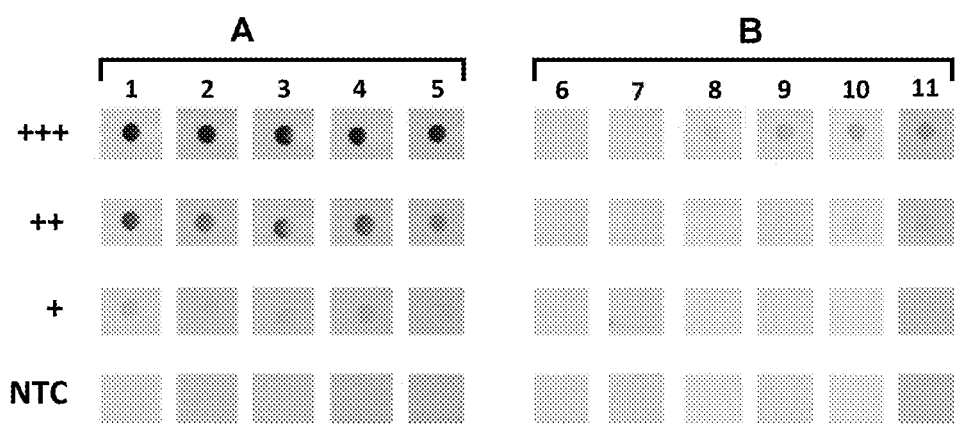
FIG. 10C. Use of repeating sequence motifs to enhance hybridisation-based detection of nucleic acids on nucleic acid lateral flow (see Example 6).

In order to test the efficiency of binding of each capture probe sequence, appropriate target probes comprising 3 or more copies of the reverse complement of the relevant repeating sequences attached to carbon via a biotin moiety were applied to the sample pad of the appropriate test strip at various levels (+++=1 pmol, ++=0.1 pmol, +=0.001 pmol, NTC=no target control) in 100 µl of an appropriate running buffer. The lateral flow test strips were developed and photographed to record the intensity of signal obtained. The data obtained is displayed in FIG. 10C and reveals that the capture probes comprising repeating sequence motifs (capture probes 1-5) lead to a greatly enhanced signal intensity compared to random sequences of similar length and Tm (capture probes 6-11). Typically, sensitivity of detection of 100-fold or more is observed. The random sequences were designed to cover a range of different GC vs AT % ratios although no correlation was observed. This experiment demonstrates conclusively that repeating sequence motifs lead to a remarkable enhancement in hybridisation affinity and to the performance of nucleic acid lateral flow based on sequence-specific hybridisation. This invention is broadly applicable to any detection method using hybridisation-based binding to a substrate, leading to an enhancement in both signal intensity and the sensitivity of detection. Duplex, triplet and quadruplet repeats are all capable of use and lead to highly efficient pull-down of oligonucleotides with appropriate regions of reverse complementarity. Multiplexing can be readily accomplished without any interference between the target probes or capture probes (see Example 3). The invention is therefore simple to employ and highly versatile.

This example reveals a striking improvement to lateral flow hybridisation based detection employing a second oligonucleotide detection moiety comprising repeat copies of a DNA sequence motif. It demonstrates that an improvement to the sensitivity of the nucleic acid lateral flow based detection of the detector species of 100-fold can be obtained. The intensity of the signal is enhanced and the signal develops more rapidly, demonstrating the potential for said embodiments of the invention to be readily applicable to applications involving rapid detection, such as by nucleic acid lateral flow. Furthermore the potential of using a single stranded oligonucleotide as the detection moiety attached to the second oligonucleotide probe is exemplified.

Example 7

Use of the Method for the Detection of an RNA Virus in Clinical Specimens

This example demonstrates the performance of the method to detect an RNA virus in clinical specimens, using the embodiment of the method wherein the first oligonucleotide probe is contacted with the sample simultaneously to the performance of the amplification step a) and the moiety that permits the attachment of the second oligonucleotide probe to a solid material is a single stranded oligonucleotide comprising of four repeat copies of a three base DNA sequence motif and the reverse complement of said single stranded oligonucleotide sequence is attached to a solid material. In various investigations we have routinely detected very low copies of RNA targets, such as viral genome extracts. For example, using quantified viral genome extracts we have employed the method of the invention to detect less than 100 genome equivalent copies of a virus in under 10 min total time to result, with an amplification step a) of less than 5 min. This remarkable rate and sensitivity demonstrates the potential of the method for application in the field of diagnostics. As such, in this example, we have developed an assay to detect a pathogenic single stranded RNA virus and demonstrated the performance of that assay using clinical specimens infected with the virus.

The first oligonucleotide primer with a total length of 25 nucleotide bases was designed comprising in the 5' to 3' direction: A stabilising region of 8 bases synthesised to contain phosphorothioate bonds between each base; the 5 bases of a recognition site for a restriction enzyme that is not a nicking enzyme; and a 12 base hybridising region comprising the reverse complementary sequence of the first hybridisation sequence in the target nucleic acid, designed to target a region within the single stranded RNA virus genome. The second oligonucleotide primer was designed to contain the same stabilising region but without the phosphorothioate bonds and the same restriction enzyme recognition sequence, but with the 12 base hybridising region capable of hybridising to the reverse complement of the second hybridisation sequence. In this example the first restriction enzyme and the second restriction enzyme are the same restriction enzyme. The first and second hybridisation sequences in the target nucleic acid are separated by 0 bases.

The oligonucleotide primers were designed using the target nucleic acid, such that the nucleotide base downstream of the cleavage site in the reverse complement of the primers is Adenosine such that alpha thiol dATP is employed as the modified dNTP for use in the method. A phosphorothioate modification is inserted by the strand displacement DNA polymerase, or the reverse transcriptase to block cleavage of said reverse complementary strand.

The first oligonucleotide probe with a total length of 24 bases was designed comprising in the 5' to 3' direction: A 5' Biotin modification added during synthesis wherein said biotin modification permits attachment of the first oligonucleotide probe to a colorimetric dye, carbon nanoparticles, a stabilising region of 8 bases; the 5 bases of the recognition sequence for a restriction enzyme that is not a nicking enzyme wherein the cleavage site for said restriction enzyme in the first oligonucleotide probe is protected by a phosphorothioate internucleotide linkage added during synthesis; an 11 base region capable of hybridising to at least one species in the amplification product; and a 3' phosphate modification which prevents extension by the strand displacement DNA polymerase.

The second oligonucleotide probe with a total length of 31 bases was designed comprising in the 5' to 3' direction: a 14 base region capable of hybridising to the second single stranded detection sequence downstream of the first single stranded detection sequence in said at least one species in the amplification product; a spacer comprising 5 X Thymidine bases; 4 X repeats of a three base DNA sequence motif (GGT), the reverse complement to which is immobilised on the lateral flow strip. The immobilised lateral flow printed oligonucleotide with a total length of 47 bases is designed comprising: A neutral spacer comprising 11 X Thymidine bases; a 12 X repeat of a 3 base sequence motif (ACC), which is complementary to the 3 base sequence motif of the second oligonucleotide probe. A lateral flow control oligonucleotide with a length of 20 bases was designed comprising in the 5' to 3' direction: a 5 X triplet repeat (CTT) which is different from that on the second oligonucleotide probe; a neutral spacer comprising 5 X Thymidine bases and a 3' Biotin molecule, added during synthesis. The control oligonucleotide binds to its reverse complement on the lateral flow strip comprising 11 X Thymidine bases and a 12X repeat of the reverse complement to the triplet repeat (AAG) to verify a successful carbon lateral flow procedure.

Reactions were prepared containing: 1.8 pmol of the first primer; 9.6 pmol of the second primer; 3.6 pmol of the first probe; 1 pmol of the second probe; 300 µM Sp-dATP-α-S from Enzo Life Sciences; 60 µM of each of dTTP, dCTP and dGTP; 28U of the restriction enzyme; 14U of a *Bacillus* strand displacement DNA polymerase; 35U of a viral reverse transcriptase enzyme; 3.5U RNaseH and 3 µg carbon adsorbed to biotin binding protein. 5 µl of nasopharyngeal swab sample collected from patients in a clinical setting (sourced from Discovery Life Sciences) which included 7 virus positive samples and 6 virus negative clinical samples (verified by PCR assay). Reactions were performed in a 70 µl volume in an appropriate reaction buffer. Reactions were incubated at 45° C. for 4 min 30 sec before the entire reaction was loaded onto a nucleic acid lateral flow strip printed with approximately 50 pmol of the reverse complement to the 3 base triplet repeat moiety of the second oligonucleotide probe (bottom) and the reverse complement to the control oligonucleotide (top line).

Figure 11:
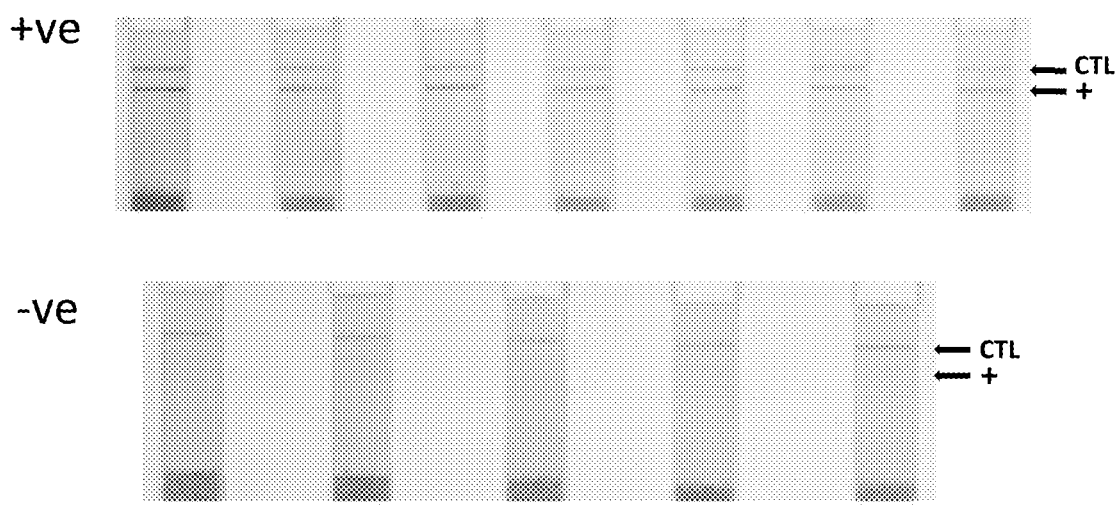
FIG. 11. Use of the method for the detection of an RNA virus in clinical specimens (see Example 7).

FIG. 11 displays a photograph of the lateral flow strips obtained in the performance of the example. The arrows indicate the position where the reverse complement to the triplet repeat moiety of the second oligonucleotide probe has been printed (+) and hence where the positive signal appears, and the position of the reverse complement to the control oligonucleotide (CTL) which verifies a successful lateral flow run and hence appears in both positive and negative assays. The top panel (+ve) shows the results obtained with the virus positive clinical samples and the bottom panel (−ve) those with the virus negative samples. A clear black line indicating the presence of target nucleic acid is present in each of the positive samples, demonstrating the rapid detection of clinical specimens by the method of the invention. No false positives were observed, demonstrating the complete absence of non-specific production of the detector species, such as through ab initio synthesis or primer-primer binding. No false negatives were observed evidencing the robustness of the method and its sensitivity across the different target nucleic acid copy number levels present within different clinical specimens.

Example 8

Performance of the Method at Different Temperatures

The method of the invention may be performed efficiently over a wide range of temperatures and does not require temperature cycling, nor any hot or warm start, pre-heating or a controlled temperature decrease. This example demonstrates the performance of a typical assay over a range of different temperatures. By selecting enzymes with the desired temperature optima, and using a phosphorothioate base that reduces the melting temperature of hybridisation following its incorporation, as assay has been readily developed wherein the amplification is performed over a surprisingly wide range of temperatures and covering an usually low temperature range. A separate experiment further demonstrates that assays developed using the method of the invention can be developed with no requirement to preheat the sample prior to the initiation of step a), and wherein no loss of performance is observed when the temperature is increased during the performance of the amplification in step a).

Example 8.1

An assay was designed exploiting the embodiment of the method wherein the first oligonucleotide probe is blocked at the 3' end from extension by the DNA polymerase and is not capable of being cleaved by either the first or second restriction enzyme and is contacted with the sample simultaneously to the performance of step a). A first primer was designed containing in the 5' to 3' direction: a neutral region of 7 bases; the recognition site of a restriction enzyme; and, a 11 base region capable of hybridising to the first hybridisation sequence in the target nucleic acid, a DNA target. A second primer was designed containing in the 5' to 3' direction: a neutral region of 7 bases; the recognition site for the same restriction enzyme as the first primer; and a 12 base region capable of hybridising to the reverse complement of the second hybridisation sequence in the target nucleic acid.

A first oligonucleotide probe was designed with a total length of 21 bases comprising in the 5' to 3' direction: a 5' Biotin modification; a neutral region of 6 bases; the bases of the recognition site of the restriction enzyme containing a mismatch at the $2^{nd}$ position; a 10 base region capable of hybridising to the first hybridisation region in the target comprising a G-clamp modification at the $6^{th}$ position; and a 3' phosphate modification, wherein the biotin modification permits attachment of the first oligonucleotide probe to a colorimetric dye, carbon nanoparticles, and the phosphate modification blocks its extension by the strand displacement DNA polymerase.

A second oligonucleotide probe was designed containing in the 5' to 3' direction: an 11 base region capable of hybridising to the reverse complement of the second hybridisation sequence in the target; a 4 X Thymidine base spacer and 12 bases comprising 4 X repeats of a 3 base sequence motif (CTT) which acts as the moiety permitting the attachment of the second oligonucleotide probe to a solid material. An additional single stranded oligonucleotide was designed comprising in the 5' to 3' direction: an 11 X Thymidine base spacer; a 33 base region comprising a 11 X repeat of the reverse complement to the 3 base sequence motif (AAG) which forms the moiety permitting attachment of the second oligonucleotide to a solid material. For the second oligonucleotide probe nucleic acid lateral flow strips were prepared spotted with 30 pmol of said additional single stranded oligonucleotide.

Reactions were prepared in appropriate buffer containing: 1.5 pmol of the first primer; 1.0 pmol of the second primer; 1 pmol of the first oligonucleotide probe; 60 µM Sp-dATP-α-S from Enzo Life Sciences; 60 µM of each of dTTP, dCTP and dGTP; and, various levels of target DNA (++=1 amol, +=10 zmol, NTC=no target control). Assembled reactions were incubated for 2 min at the target temperature (I=37° C.; II=45° C., III=50° C. and IV=55° C.) before being initiated by final addition of 5U of the restriction enzyme and 5U of a Bacillus strand displacement DNA polymerase to a final reaction volume of 25 82 l. Reactions were then incubated for 5 min (T1) or 8 min (T2) at the relevant target temperature. Following incubation, each reaction was transferred to 75 µl of buffer containing 1.5 pmol of the second oligonucleotide probe and 8 µg of carbon adsorbed to biotin binding protein before application to the sample pad of thenucleic acid lateral flow strip.

Figure 12A:
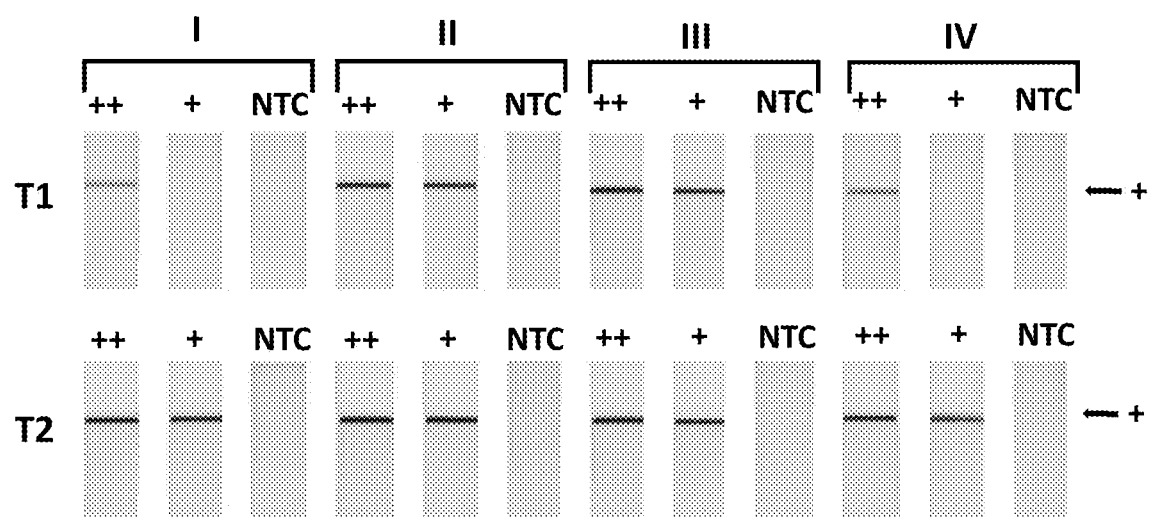
FIGS. 12A and 12B. Performance of the method at different temperatures (see Example 8).

FIG. 12A displays photographs of the lateral flow strips obtained in the experiment at each target level, temperature and timepoint. The clear black lines observed correspond to the deposition of carbon attached detector species produced in the presence of target. At all temperatures a very strong signal appeared in the presence of target at both target levels within 8 min demonstrating the broad temperature range of efficient amplification of the method. No non-specific amplification was observed in the NTC samples. Strong amplification was also observed after just 5 min at 45° C. and 50° C. indicating that the optimum temperature for this assay is likely to be between 40° C. and 50° C.

Example 8.2

A second assay was designed exploiting the embodiment of the method wherein the first oligonucleotide probe is blocked at the 3' end from extension by the DNA polymerase and is not capable of being cleaved by either the first or second restriction enzyme and contacted with the sample simultaneously to the performance of step a). Both the first and second primers were designed to contain in the 5' to 3' direction: a neutral region of 6 bases; the recognition site of a restriction enzyme; and a 12 base hybridisation region for the target nucleic acid. The primers were designed such that the first and second hybridisation sequences in the target are separated by 10 bases.

A first oligonucleotide probe was designed with a total length of 23 bases comprising in the 5' to 3' direction: a 5' Biotin modification; a neutral region of 6 bases; the bases of the recognition site of the restriction enzyme containing a mismatch at the 4th position; a 12 base region capable of hybridising to the first hybridisation region in the target; and a 3' phosphate modification, wherein the biotin modification permits attachment of the first oligonucleotide probe to a colorimetric dye, carbon nanoparticles, and the phosphate modification blocks its extension by the strand displacement DNA polymerase.

A second oligonucleotide probe was designed containing in the 5' to 3' direction: a 13 base region capable of hybridising to 3 bases of the reverse complement of the second hybridisation sequence in the target and the 10 base gap between the first and second hybridisation sequences; a 3 X Thymidine base spacer and 12 bases comprising 4 X repeats of a 3 base sequence motif (ATT) which acts as the moiety permitting the attachment of the second oligonucleotide probe to a solid material. An additional single stranded oligonucleotide was designed comprising in the 5' to 3' direction: an 11 X Thymidine base spacer; and a 36 base region comprising a 12 X repeat of the reverse complement to the 3 base sequence motif (AAT) which forms the moiety permitting attachment of the second oligonucleotide to a solid material. For the second oligonucleotide probe nucleic acid lateral flow strips were prepared spotted with 30 pmol of said additional single stranded oligonucleotide.

Reactions were prepared in appropriate buffer containing: 6 pmol of the first oligonucleotide primer; 8 pmol of the second oligonucleotide primer; 6 pmol of the first oligonucleotide probe; 60 µM Sp-dATP-α-S from Enzo Life Sciences; 60 µM of each of dTTP, dCTP and dGTP; 60 µg of carbon adsorbed to biotin binding protein; and, where applicable, target. Assembled reactions were incubated for 2 min at the starting temperature (I=15° C.; II=45° C.) before reactions were initiated by final addition of 20U of the restriction enzyme, 20U of a *Bacillus* strand displacement DNA polymerase and 40U of reverse transcriptase to a final reaction volume of 100 µl. Following enzyme addition, the reactions with the 15° C. starting temperature were immediately transferred to 45° C. alongside the other reactions.

Figure 12B:
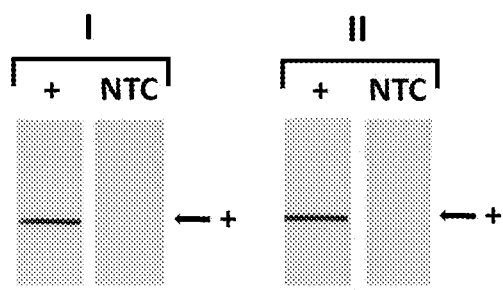

Reactions were then incubated for 6 min at 45° C. Following incubation, each reaction was transferred to the sample pad of a nucleic acid lateral flow strip, which sample pad contained 3 pmol of the second oligonucleotide probe. FIG. 12B displays photographs of the lateral flow strips obtained in the experiment at each temperature incubation conditions. The clear black lines observed correspond to the deposition of carbon attached detector species produced in the presence of target. No difference was observed in the reaction wherein the temperature had been increased from 15° C. to 45° C. during the amplification step a). The same remarkable rate of amplification occurred as in the pre-heated reaction, and no non-specific amplification was observed in the NTC sample.

This Example 8 demonstrates that the method of the invention can be used to readily develop assays with a lower optimal temperature profile compared to known methods, and which can be exploited for sensitive detection over an unusually broad range of temperatures. It also demonstrates that the method of the invention can be performed without preheating wherein the temperature is increased during the performance of step a). Such features are highly attractive for use of the method in a low-cost diagnostic device, where high temperatures and precisely controlled heating impose complex physical constraints that increase the cost-of-goods of such a device to a point where a single-use or instrument-free device is not commercially viable. Furthermore by avoiding the requirement of known methods to pre-heat the sample prior to the initiation of amplification, the method of the invention can be performed with fewer user steps and a simpler sequence of operations, thus increasing the usability of such a diagnostic device and decreasing the overall time to result.

Example 9

Performance of the Method Wherein the Target Nucleic Acid is Derived From Double Stranded DNA by Strand Invasion This example demonstrates the use of the method wherein the single stranded target nucleic acid is a single stranded site within double stranded DNA that is detected without any requirement for specific action to separate the DNA strands, such as temperature denaturation, bump primers or use of an additional enzyme (e.g. helicase or recombinase). The ability to use the method of the invention readily for the detection of both single-stranded RNA and double-stranded DNA targets makes it highly versatile for use in diagnostic applications, without additional user steps, components or physical requirements imposed on the device used to perform the method.

Example 9.1

An assay was developed for a protein coding region within the double-stranded DNA genome a viral target. It is possible to use either the double-stranded genome or the mRNA transcript as a biomarker for the presence of the virus in clinical diagnosis. The assay was designed exploiting the embodiment of the method wherein the first oligonucleotide probe is blocked at the 3' end from extension by the DNA polymerase and is not capable of being cleaved by either the first or second restriction enzyme and is contacted with the sample simultaneously to the performance of step a). The design of the oligonucleotide primers and oligonucleotide probes was performed following a similar approach to that described in other examples, with no gap between the first and the second hybridisation sequences in the target nucleic acid.

Reactions were prepared in appropriate buffer containing: 4 pmol of the first oligonucleotide primer; 2 pmol of the second oligonucleotide primer; 2 pmol of the first oligonucleotide probe; 60 µM Sp-dATP-α-S from Enzo Life Sciences; 60 µM of each of dTTP, dCTP and dGTP; 60 µb of carbon adsorbed to biotin binding protein; and either double stranded DNA target (I) or single-stranded RNA target (II) or no target. Assembled reactions were incubated for 2 min at the 45° C. before being initiated by final addition of 20U of the restriction enzyme, 20U of a *Bacillus* strand displacement DNA polymerase and 25U of reverse transcriptase to a final reaction volume of 100 µl. Following enzyme addition, the reactions were incubated at 45° C. for 7 min.

Figure 13A:
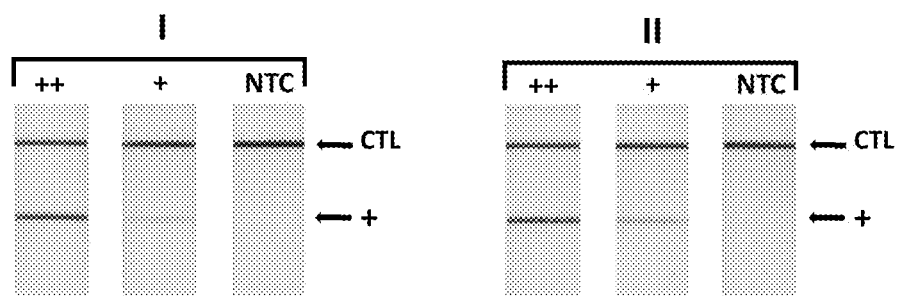
FIGS. 13A and 13B. Performance of the method wherein the target nucleic acid is derived from double stranded DNA by strand invasion (see Example 9).

Following incubation, 1.5 pmol of the second oligonucleotide probe was added to each reaction and the entire reaction volume was transferred to the sample pad of a nucleic acid lateral flow strip. A nucleic acid lateral flow control target was also added to all samples. FIG. 13A displays photographs of the lateral flow strips obtained in the experiment with each target. The clear black lines observed correspond to the deposition of carbon attached detector species produced in the presence of target, with a fainter signal corresponding to the lower target level (+) than the higher target lever (++). No difference in the rate of amplification was observed between the single stranded RNA and double stranded DNA targets.

Example 9.2

An assay was designed for a single stranded target nucleic acid within the c.2.5 megabase double stranded DNA genome of a bacterial pathogen. The assay was designed exploiting the embodiment of the method wherein the first oligonucleotide probe is blocked at the 3' end from extension by the DNA polymerase and is not capable of being cleaved by either the first or second restriction enzyme and is contacted with the sample simultaneously to the performance of step a). The design of the oligonucleotide primers and oligonucleotide probes was performed following a similar approach to that described in other examples, with a gap of 4 bases between the first and the second hybridisation sequences in the target nucleic acid.

Reactions were prepared in appropriate buffer containing 2 pmol of the first oligonucleotide primer and 0.5 pmol of the second oligonucleotide primer. Due to the use of a double stranded DNA target, two single stranded target nucleic acids are in fact added at the same time and it is assumed that a second reciprocal process also occurs, wherein the second oligonucleotide primer for detection of the target nucleic acid is the first oligonucleotide primer for the detection of the second target nucleic acid, being the reverse complement of the target nucleic acid. This fact has little impact on the performance of the method. 2 pmol of the first oligonucleotide probe; 60 µM Sp-dATP-α-S from Enzo Life Sciences; 60 µM of each of dTTP, dCTP and dGTP; 15 µg of carbon adsorbed to biotin binding protein; and genome extract of the bacteria containing the target at various levels (++=1 amol; +=10 zmol; NTC=no target control). A further specificity control reaction was also performed containing 1 amol of genome extract of *E. coli*. Assembled reactions were incubated for 3 min at 45° C. before being initiated by final addition of 4U of the restriction enzyme and 2U of a *Bacillus* strand displacement DNA polymerase to a final reaction volume of 25 µl. Following enzyme addition, the reactions were incubated at 45° C. for 6 min.

Figure 13B:
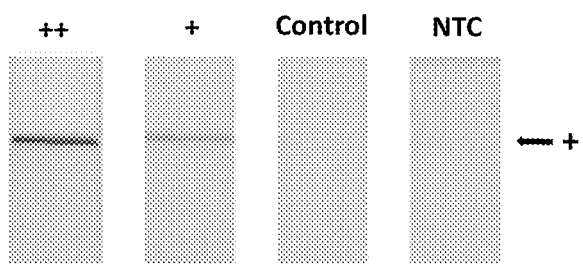

Following incubation, 75 µl buffer containing 3 pmol of the second oligonucleotide probe was added to each reaction and the entire volume was then transferred to the sample pad of a nucleic acid lateral flow strip. FIG. 13B displays photographs of the lateral flow strips obtained in the experiment with each target. Clear black lines corresponding to the deposition of carbon attached detector species produced in the presence of target are observed at both target levels tested. No non-specific signal was observed in the no target control or in the presence of *E. coli* genomic DNA demonstrating that the method can be employed for the specific detection of a complex double-stranded DNA genome at a clinically relevant copy number within just 6 min.

This example demonstrates that the method of the invention can be readily used for the detection of single stranded nucleic acid targets within double stranded DNA. Remarkably, a similar rate of amplification is observed for the detection of single stranded RNA target and the same target sequence within double stranded DNA, without any requirement for specific action such as temperature denaturation to separate the DNA duplex. Instead the single stranded site is exposed sufficiently for hybridisation and extension of the first oligonucleotide primer to initiate the method by "strand invasion" wherein transient opening of one or more DNA base pairs within the double stranded DNA occurs sufficiently to permit hybridisation and extension of the 3' hydroxyl of the first oligonucleotide primer. This contrasts with known methods such as SDA wherein heat denaturation and bump primers are utilised in assays for double stranded nucleic acids. The ability to use the method of the invention readily to detect targets within double-stranded DNA in addition to those within single stranded DNA and single stranded RNA makes it highly versatile for use in diagnostic applications, such as in the detection of bacterial, fungal and viral pathogens that have a double stranded DNA genome. The fact that the method has no requirement for complex additional user steps, enzymes, components or physical constraints to detect organisms with double stranded DNA genomes means it is particularly well-suited for testing in a simple, low-cost diagnostic device. For example, the requirement for heat denaturation prior to performance of amplification reported for known methods would necessitate expensive additional components and increase the costs of goods of such a device and the total time to result, meaning that a single-use or self-contained, instrument free device would not be viable.

Example 10

Comparative Performance of the Method of the Invention Versus Known Methods

This example presents a comparative evaluation of the method of the invention against the known method disclosed in WO2014/164479 for the detection of a viral target. The known method is fundamentally different to the method of the invention in that it requires nicking enzymes and does not require the use of one or more modified dNTP. The method of the invention is demonstrated to have vastly superior sensitivity and specificity.

For this comparative evaluation an assay was first developed for a viral target with a single-stranded RNA genome using the method of the invention. Said assay was designed exploiting the embodiment of the method wherein the first oligonucleotide probe is blocked at the 3' end from extension by the DNA polymerase and is not capable of being cleaved by either the first or second restriction enzyme and contacted with the sample simultaneously to the performance of step a). The design of the oligonucleotide primers and oligonucleotide probes was performed following a similar approach to that described in other examples, with a gap of 6 bases between the first and second hybridisation sequences in the target nucleic acid.

For the assay using the known method, similar primers were designed containing the same 6 base neutral region at the 5' ends and the same hybridisation regions at the 3' end as the equivalent primers used in the method of the invention. In this way consistency was ensured as much as possible between the two assays for an accurate comparison of the methods. However, the bases of the restriction enzyme recognition site were replaced with those of the exemplary nicking enzyme reported in WO2014/164479, Nt.BbvCI (see Example 5 on p.20-21).

Example 10.1

In the first instance, reactions for each method were performed using equal primer ratios. For the method of the invention, reactions were prepared in appropriate buffer containing: 2 pmol of the first oligonucleotide primer; 2 pmol of the second oligonucleotide primer; 1.6 pmol of the first oligonucleotide probe; 60 µM Sp-dATP-α-S from Enzo Life Sciences; 60 µM of each of dTTP, dCTP and dGTP; and viral genomic RNA extract at various levels as target (+++=10 zmol; ++=100 copies; +=10 copies; NTC=no target control). Assembled reactions were preincubated for 5 min at ambient conditions (c.20° C.) before reactions were initiated by addition of 5U of the restriction enzyme, 5U of a *Bacillus* strand displacement DNA polymerase and 10U of reverse transcriptase in a final reaction volume of 25 µl. Following enzyme addition, the reactions were incubated at 45° C. for 8 min (T1) or 15 min (T2). Following incubation, 60 µg of carbon adsorbed to biotin binding protein in 75 µl buffer was added to each reaction and the entire 100 µl volume was transferred to a nucleic acid lateral flow strip containing 1.5 pmol of the second oligonucleotide probe on the sample pad.

For the known method, reactions were prepared in appropriate buffer containing: 6.25 pmol of the first oligonucleotide primer; 6.25 pmol of the second oligonucleotide primer; 200 µM of each of dATP, dTTP, dCTP and dGTP; and viral genomic RNA extract at various levels as target (+++=10 zmol; ++=100 copies; +=10 copies; NTC=no target control). Assembled reactions were preincubated for 5 min at ambient conditions (c.20° C.) before reactions were initiated by addition of 4U of Nt.BbvCI, 20U of Bst large fragment DNA polymerase and 10U of M-MuLV reverse transcriptase in a final reaction volume of 25 µl. Following enzyme addition, the reactions were incubated at 45° C. for 8 min (T1) and 15 min (T2). Following incubation, 75 µl buffer containing 60 µg carbon adsorbed to biotin binding protein and 5 pmol of the first oligonucleotide probe was added to each reaction and the entire 100 µl volume was transferred to a nucleic acid lateral flow strip containing 5 pmol of the second oligonucleotide probe on the sample pad.

Figure 14A:
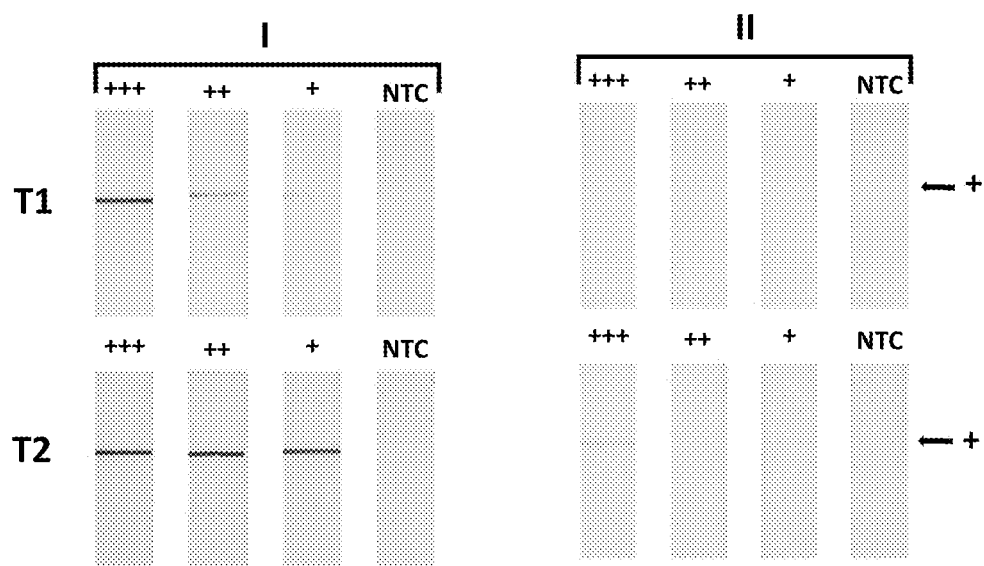
FIGS. 14A and 14B. Comparative performance of the method of the invention versus known methods (see Example 10).

FIG. 14A displays photographs of the lateral flow strips obtained in the experiment with the method of the invention (I) and with the known method (II), at the various target levels and time points indicated. The black lines observed correspond to the deposition of carbon attached detector species produced in the presence of target. Several attempts were required before it was possible to observe any signal at all using the known method and it was necessary to use a particular combination of enzymes and buffer and significantly higher levels of primers, dNTPs and enzymes. With the method of the invention (I), even at the shortest time point after just 8 min without a pre-heat it was possible to clearly see the detector species produced even at the lowest target level of just 10 copies of target. Even after efforts to optimise the known method which would not have been obvious to the skilled person, only a faint signal was observed at the highest target level (+++=10 zmol) and at the longest time point (15 min).

Example 10.2

After extensive further, non-obvious, attempts it was possible to increase the performance of the known method, but only by using a 2:1 ratio of the first and second oligonucleotide primers, with a very high concentration of the first primer, as described in this Example 10.2. The method of the invention was performed again as described in Example 10.1. For the known method, the reactions were performed as described in Example 10.1 except that the level of the first oligonucleotide primer was increased to 12.5 pmol. In each case the following target levels were used: +++=1 zmol; ++=100 copies; +=10 copies; NTC=no target control.

Figure 14B:
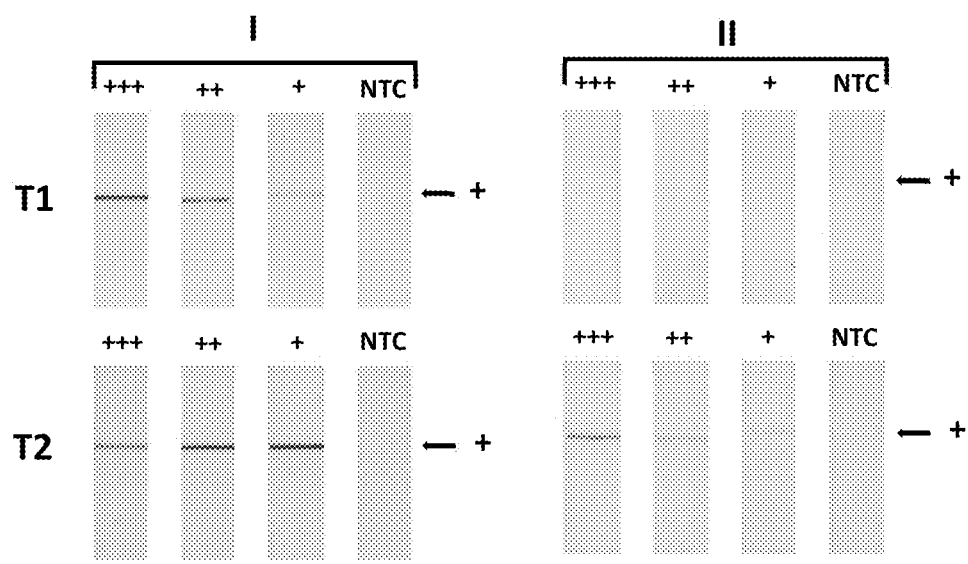

FIG. 14B displays photographs of the lateral flow strips obtained in the experiment with the method of the invention (I) and with the known method (II), at the various target levels and time points indicated. The black lines observed correspond to the deposition of carbon attached detector species produced in the presence of target. Again, the method of the invention (I) demonstrated a remarkable rate with signal visible even at the shortest time point and at the lowest target level of just 10 copies of target. With the known method only a faint signal was observed at the highest target level (+++=1 zmol) and a very faint signal was visible in the 100 copy sample at the longest time point (15 min). However, a faint signal was also observed in the NTC strip which may correspond to non-specific product as a result of the very high oligonucleotide primer levels and enzyme levels required to get the method to work at all. These data are consistent with the data in WO2014/164479 wherein an incubation time of 30 min was reported. The requirement to add unusually high primer levels in order to speed up the amplification performed using this known method would greatly limit its potential application to the detection of two or more different targets in the same sample, as there would be very limited scope to further increase the total primer level without exacerbating the problem with non-specific products.

This Example 10 demonstrates the striking superiority of the method of the invention over the known method disclosed in WO2014/164479 with amplification performed much more rapidly, with greater sensitivity and with a more clear results signal produced. In just 8 min without pre-incubation the method of the invention produced a stronger signal with just 100 copies of target than the known method was able to in 15 min at the highest target level with 60X the level of target. The advantages of the method of the invention over this known method arise from its requirement for a different class of enzyme, being restriction enzymes that are not nicking enzymes, and from its requirement for use of one or more modified dNTP, such as a phosphorothioate base which enhances the sensitivity and specificity of amplification. Furthermore, the embodiment of the method wherein one of the first and second oligonucleotide probes is blocked at the 3' end from extension by the DNA polymerase and is not capable of being cleaved by either the first or second restriction enzyme and is contacted with the sample simultaneously to the performance of step a), enables efficient coupling of amplification to signal detection and facilitates enhanced specificity derived from efficient sequence based hybridisation during the formation of the detector species. These advantages make the method of the invention ideally suited to exploitation in the field of diagnostics and to the development of simple, ultra-rapid, user-centred, low-cost diagnostic devices, such as a single-use or instrument free molecular diagnostic test device.

Throughout the specification and the claims which follow, unless the context requires otherwise, the word "comprise", and variations such as "comprises" and "comprising", will be understood to imply the inclusion of a stated integer, step, group of integers or group of steps but not to the exclusion of any other integer, step, group of integers or group of steps.

Additional aspects of the invention include those listed below:

1. A method for detecting the presence of a single stranded target nucleic acid of defined sequence in a sample comprising:
   a) contacting the sample with:
      i. a first oligonucleotide primer and a second oligonucleotide primer wherein said first primer comprises in the 5' to 3' direction one strand of a restriction enzyme recognition sequence and cleavage site and a region that is capable of hybridising to a first hybridisation sequence in the target nucleic acid, and said second primer comprises in the 5' to 3' direction one strand of a restriction enzyme recognition sequence and cleavage site and a region that is capable of hybridising to the reverse complement of a second hybridisation sequence upstream of the first hybridisation sequence in the target nucleic acid;
      ii. a strand displacement DNA polymerase;
      iii. dNTPs;
      iv. one or more modified dNTP;
      v. a first restriction enzyme that is not a nicking enzyme but is capable of recognising the recognition sequence of the first primer and cleaving only the first primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP; and
      vi. a second restriction enzyme that is not a nicking enzyme but is capable of recognising the recognition sequence of the second primer and cleaving only the second primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP;
to produce, without temperature cycling, in the presence of said target nucleic acid, amplification product;
b) contacting the amplification product of step a) with:
i. a first oligonucleotide probe which is capable of hybridising to a first single stranded detection sequence in at least one species within the amplification product and which is attached to a moiety that permits its detection; and
ii. a second oligonucleotide probe which is capable of hybridising to a second single stranded detection sequence upstream or downstream of the first single stranded detection sequence in said at least one species within the amplification product and which is attached to a solid material or to a moiety that permits its attachment to a solid material;
where hybridisation of the first and second probes to said at least one species within the amplification product produces a detector species; and
c) detecting the presence of the detector species produced in step b) wherein the presence of the detector species indicates the presence of the target nucleic acid in said sample.
2. A method according to aspect 1 wherein one of the first and second oligonucleotide probes is blocked at the 3' end from extension by the DNA polymerase and is not capable of being cleaved by either the first or second restriction enzymes.
3. A method according to aspect 2 wherein the one oligonucleotide probe is rendered not capable of being cleaved by either the first or second restriction enzymes due to the presence of one or more sequence mismatch and/or one or more modifications such as a phosphorothioate linkage.
4. A method according to aspect 2 or 3 wherein the one oligonucleotide probe is contacted with the sample simultaneously to the performance of step a).
5. A method according to any of the preceding aspects wherein the sample additionally is contacted in step a) with: (A) a third oligonucleotide primer which third primer comprises in the 5' to 3' direction one strand of the recognition sequence and cleavage site for the first restriction enzyme and a region that is capable of hybridising to the first hybridisation sequence in the target nucleic acid and wherein said third primer is blocked at the 3' end from extension by the DNA polymerase; and/or (B) a fourth oligonucleotide primer which fourth primer comprises in the 5' to 3' direction one strand of the recognition sequence and cleavage site for the second restriction enzyme and a region that is capable of hybridising to the reverse complement of the second hybridisation sequence in the target sequence and wherein said fourth primer is blocked at the 3' end from extension by the DNA polymerase.
6. A method according to aspect 5 wherein when present the third oligonucleotide primer is provided in excess of the first oligonucleotide primer and when present the fourth oligonucleotide primer is provided in excess of the second oligonucleotide primer.
7. A method according to any of the preceding aspects wherein the one or more modified dNTP is an alpha thiol modified dNTP.
8. A method according to any of the preceding aspects wherein the first and second restriction enzyme are the same restriction enzyme.
9. A method according to any of the preceding aspects wherein two or more of steps a), b) and c) are performed simultaneously.
10. A method according to any of the preceding aspects wherein step (a) is performed at a temperature of not more than 50° C.
11. A method according to any of the preceding aspects wherein the moiety that permits the detection of the first oligonucleotide probe, is a colorimetric or fluorometric dye or a moiety that is capable of attachment to a colorimetric or fluorometric dye such as biotin.
12. A method according to any of the preceding aspects wherein the detector species is detected by a change in electrical signal.
13. A method according to any of the preceding aspects wherein the moiety that permits the detection of the first oligonucleotide probe is an enzyme that yields a detectable signal, such as a colorimetric or fluorometric signal, following contact with a substrate.
14. A method according to any of the preceding aspects wherein the moiety that permits the attachment of the second oligonucleotide probe to a solid material is a single stranded oligonucleotide.
15. A method according to aspect 14 wherein the sequence of the single stranded oligonucleotide moiety comprises three or more repeat copies of a 2 to 4 base DNA sequence motif.
16. A method according to any of the preceding aspects wherein in step c) the presence of the detector species is detected by nucleic acid lateral flow.
17. A method according to aspect 16 wherein the nucleic acid lateral flow utilises one or more nucleic acids that is capable of sequence specific hybridisation to the moiety that permits the attachment of the second oligonucleotide probe to a solid material.
18. A method according to any of the preceding aspects wherein step c) produces a colorimetric or electrochemical signal using carbon or gold, preferably carbon.
19. A method according to any of the preceding aspects wherein the first and/or second oligonucleotide primers comprise a stabilising sequence at the 5' end, e.g. of 5 bases in length upstream of the restriction enzyme recognition sequence and cleavage site.
20. A method according to any of the preceding aspects wherein the hybridising region of the first and/or second oligonucleotide primers is between 9 and 16 bases in length.
21. A method according to any of the preceding aspects wherein one of the first and second oligonucleotide primers is provided in excess of the other.
22. A method according to any of the preceding aspects wherein the first and second hybridisation sequences in the target nucleic acid are separated by 0 to 6 bases.
23. A method according to any of the preceding aspects wherein the first and second hybridisation sequences in the target nucleic acid are separated by 3 to 6 bases.
24. A method according to any of the preceding aspects wherein in step b) either the first or second single stranded detection sequence in the at least one species within the amplification product includes the sequence corresponding to the 3 to 6 bases defined in claim 23.
25. A method according to any of the preceding aspects wherein the level of the target nucleic acid in said sample is quantified in step c).
26. A method according to any of the preceding aspects wherein the target nucleic acid is single stranded RNA, including single stranded RNA derived from double stranded RNA and single stranded RNA derived from double stranded DNA, or single stranded DNA, including single stranded DNA derived from single stranded RNA and single stranded DNA derived from double stranded DNA.

27. A method according to aspect 26 wherein said single stranded DNA is derived from double stranded DNA by use of a nuclease, such as a restriction endonuclease or exonuclease III or derived from single stranded RNA by use of reverse transcriptase.

28. A method according to any of the preceding aspects wherein the presence of two or more different target nucleic acids of defined sequence are detected in the same sample.

29. A method according to any of the preceding aspects wherein the sample is a biological sample, such as a nasal or nasopharyngeal swab or aspirate, blood or a sample derived from blood, or urine.

30. A method according to any of the preceding aspects wherein the target nucleic acid is viral or derived from viral nucleic acid material, is bacterial or derived from bacterial nucleic acid material, is circulating, cell-free DNA released from cancer cells or foetal cells, is micro RNA or derived from micro RNA.

31. A method according to any of the preceding aspects wherein the target nucleic acid contains a site of epigenetic modification, such as methylation.

32. A method according to any of the preceding aspects wherein the detection of the target nucleic acid is used for the diagnosis, prognosis or monitoring of a disease or a diseased state.

33. A method according to aspect 32 wherein said disease is an infectious disease, including but not limited to HIV, influenza, RSV, Rhinovirus, norovirus, tuberculosis, HPV, meningitis, hepatitis, MRSA, Ebola, *Clostridium difficile*, Epstein-Barr virus, malaria, plague, polio, chlamydia, herpes, gonorrhoea, measles, mumps, rubella, cholera or smallpox.

34. A method according to aspect 32 wherein said disease is a cancer, including but not limited to colorectal cancer, lung cancer, breast cancer, pancreatic cancer, prostate cancer, liver cancer, bladder cancer, leukaemia, esophageal cancer, ovarian cancer, kidney cancer, stomach cancer or melanoma.

35. A method according to any of the preceding aspects wherein the detection of said target nucleic acid is used for human genetic testing, prenatal testing, blood contamination screening, pharmacogenomics or pharmacokinetics.

36. A method according to any of the preceding aspects wherein the sample is a human sample, a forensic sample, an agricultural sample, a veterinary sample, an environmental sample or a biodefence sample.

37. A kit comprising:
   a) a first oligonucleotide primer and a second oligonucleotide primer wherein said first primer comprises in the 5' to 3' direction a restriction enzyme recognition sequence and cleavage site and a region that is capable of hybridising to a first hybridisation sequence in a single stranded target nucleic acid of defined sequence, and said second primer comprises in the 5' to 3' direction a restriction enzyme recognition sequence and cleavage site and a region that is capable of hybridising to the reverse complement of a second hybridisation sequence upstream of the first hybridisation sequence in the target nucleic acid;
   b) a first restriction enzyme that is not a nicking enzyme and is capable of recognising the recognition sequence of and cleaving the cleavage site of the first primer and a second restriction enzyme that is not a nicking enzyme and is capable of recognising the recognition sequence of and cleaving the cleavage site of the second primer;
   c) a strand displacement DNA polymerase;
   d) dNTPs;
   e) one or more modified dNTP;
   f) a first oligonucleotide probe which has some complementarity to the hybridising region of one of the first and second oligonucleotide primers and is attached to a moiety that permits its detection; and
   g) a second oligonucleotide probe which has some complementarity to the reverse complement of the hybridising region of the other of the first and second oligonucleotide primer and is attached to a solid material or to a moiety that permits its attachment to a solid material.

38. A kit according to aspect 37 which additionally comprises means to detect the presence of the detector species.

39. A kit according to aspect 37 or 38 wherein the first oligonucleotide primer and/or the second oligonucleotide primer and/or the first restriction enzyme and/or the second restriction enzyme and/or the DNA polymerase and/or the dNTPs and/or the one or more modified dNTP and/or the first oligonucleotide probe and/or the second oligonucleotide probe are as defined in any one of aspects 2, 3, 7, 8, 11, 13 to 17, 19, 20 or 22 to 24.

40. A kit according to any of aspects 37 to 39 which additionally comprises third and/or fourth oligonucleotide primers as defined in aspect 5 or 6.

41. A method for detecting the presence of a single stranded target nucleic acid of defined sequence in a sample comprising:
   a) contacting the sample with:
      i. a first oligonucleotide primer and a second oligonucleotide primer wherein said first primer comprises in the 5' to 3' direction one strand of a restriction enzyme recognition sequence and cleavage site and a region that is capable of hybridising to a first hybridisation sequence in the target nucleic acid, and said second primer comprises in the 5' to 3' direction one strand of a restriction enzyme recognition sequence and cleavage site and a region that is capable of hybridising to the reverse complement of a second hybridisation sequence upstream of the first hybridisation sequence in the target nucleic acid;
      ii. a strand displacement DNA polymerase;
      iii. dNTPs;
      iv. one or more modified dNTP;
      v. a first restriction enzyme that is not a nicking enzyme but is capable of recognising the recognition sequence of the first primer and cleaving only the first primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP; and
      vi. a second restriction enzyme that is not a nicking enzyme but is capable of recognising the recognition sequence of the second primer and cleaving only the second primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP;

to produce, without temperature cycling, in the presence of said target nucleic acid, amplification product;

b) contacting the amplification product of step a) with:
  i. a first oligonucleotide probe which is capable of hybridising to a first single stranded detection sequence in at least one species within the amplification product and which is attached to a moiety that permits its detection; and
  ii. a second oligonucleotide probe which is capable of hybridising to a second single stranded detection sequence upstream or downstream of the first single stranded detection sequence in said at least one species within the amplification product and which is attached to a solid material or to a moiety that permits its attachment to a solid material;

wherein one of the first and second oligonucleotide probes is blocked at the 3' end from extension by the DNA polymerase and is not capable of being cleaved by either the first or second restriction enzymes, and where hybridisation of the first and second probes to said at least one species within the amplification product produces a detector species; and c) detecting the presence of the detector species produced in step b) wherein the presence of the detector species indicates the presence of the target nucleic acid in said sample;

and wherein either the first or second oligonucleotide probe defined in step b) is contacted with the sample simultaneously to the performance of step a).

All patents and patent applications referred to herein are incorporated by reference in their entirety.

The invention claimed is:

1. A method for detecting the presence of a single stranded target nucleic acid of defined sequence in a sample comprising:
   a) contacting the sample with:
      (i) a first oligonucleotide primer and a second oligonucleotide primer wherein said first primer comprises in the 5' to 3' direction one strand of a restriction enzyme recognition sequence and cleavage site and a region that is capable of hybridising to a first hybridisation sequence in the target nucleic acid, and said second primer comprises in the 5' to 3' direction one strand of a restriction enzyme recognition sequence and cleavage site and a region that is capable of hybridising to the reverse complement of a second hybridisation sequence upstream of the first hybridisation sequence in the target nucleic acid;
      (ii) a strand displacement DNA polymerase;
      (iii) dNTPs;
      (iv) one or more modified dNTP;
      (v) a first restriction enzyme that is not a nicking enzyme but is capable of recognising the recognition sequence of the first primer and cleaving only the first primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP; and
      (vi) a second restriction enzyme that is not a nicking enzyme but is capable of recognising the recognition sequence of the second primer and cleaving only the second primer strand of the cleavage site when said recognition sequence and cleavage site are double stranded, the cleavage of the reverse complementary strand being blocked due to the presence of one or more modifications incorporated into said reverse complementary strand by the DNA polymerase using the one or more modified dNTP;
   to produce, without temperature cycling, in the presence of said target nucleic acid, amplification product;
   b) contacting the amplification product of step a) with:
      (i) a first oligonucleotide probe which is capable of hybridising to a first single stranded detection sequence in at least one species within the amplification product and which is attached to a moiety that permits its detection; and
      (ii) a second oligonucleotide probe which is capable of hybridising to a second single stranded detection sequence upstream or downstream of the first single stranded detection sequence in said at least one species within the amplification product and comprises a repeat motif sequence comprising 3 or more repeat copies of a 2 to 4 base DNA sequence motif;
   wherein one of the first and second oligonucleotide probes is blocked at the 3' end from extension by the DNA polymerase and is not capable of being cleaved by either the first or second restriction enzymes, and wherein the blocked oligonucleotide probe is contacted with the sample simultaneously to the performance of step a);
   and where hybridisation of the first and second probes to said at least one species within the amplification product produces a detector species; and
   c) detecting the presence of the detector species produced in step b) by contacting the detector species with a substrate having an immobilised oligonucleotide capture probe comprising a single stranded hybridisation sequence complementary to the repeat motif sequence, wherein the presence of the detector species indicates the presence of the target nucleic acid in said sample.

2. The method according to claim 1, wherein the blocked oligonucleotide probe is rendered not capable of being cleaved by either the first or second restriction enzymes due to the presence of one or more sequence mismatch(es) and/or one or more modification(s).

3. The method according to claim 2, wherein the one or more modification(s) are phosphorothioate linkage(s).

4. The method according to claim 1, wherein the blocked oligonucleotide probe comprises an additional region such that the 3' end of the species within the amplification product to which the blocked oligonucleotide probe hybridises can be extended by the strand displacement DNA polymerase.

5. The method according to claim 1, wherein the one or more modified dNTP is an alpha thiol modified dNTP.

6. The method according to claim 5, wherein the first and second hybridisation sequences in the target nucleic acid are separated by 3 to 15 bases and wherein in step b) either the first or second single stranded detection sequence in the at least one species within the amplification product includes at least 3 bases of the sequence corresponding to the 3 to 15 bases separating the first and second hybridisation sequences in the target nucleic acid.

7. The method according to claim 1, wherein the first and second restriction enzyme are the same restriction enzyme.

8. The method according to claim 1, wherein the moiety that permits the detection of the first oligonucleotide probe, is a colorimetric or fluorometric dye or a moiety that is capable of attachment to a colorimetric or fluorometric dye.

9. The method according to claim 8, wherein the moiety that is capable of attachment to a colorimetric or fluorometric dye is biotin.

10. The method according to claim 1, wherein the detector species is detected by a change in electrical signal.

11. The method according to claim 1, wherein the presence of the detector species is detected by nucleic acid lateral flow, wherein the nucleic acid lateral flow comprises the oligonucleotide capture probe immobilized on the lateral flow strip.

12. The method according to claim 1, wherein step c) produces a colorimetric or electrochemical signal using carbon or gold.

13. The method according to claim 1, wherein the first and second hybridisation sequences in the target nucleic acid are separated by 0 to 15 bases.

14. The method according to claim 1, wherein the target nucleic acid is selected from
   (i) single stranded RNA, including single stranded RNA derived from double stranded RNA and single stranded RNA derived from double stranded DNA; or
   (ii) single stranded DNA, including single stranded DNA derived from single stranded RNA including by use of a reverse transcriptase, single stranded DNA derived from double stranded DNA by strand invasion, and single stranded DNA derived from double stranded DNA by use of a nuclease.

15. The method according to claim 1, wherein the presence of two or more different target nucleic acids of defined sequence are detected in the same sample.

16. The method according to claim 1, wherein the sample is a biological sample, including a nasal or nasopharyngeal swab or aspirate, blood or a sample derived from blood, urine, a human sample, a forensic sample, an agricultural sample, a veterinary sample, an environmental sample or a biodefence sample.

17. The method according to claim 1, wherein the target nucleic acid is viral or derived from viral nucleic acid material, is bacterial or derived from bacterial nucleic acid material, is circulating, cell-free DNA released from cancer cells or foetal cells, is micro RNA or derived from micro RNA.

18. The method according to claim 1, wherein the target nucleic acid is derived from a pathogen.

19. The method of claim 18, wherein the pathogen is viral.

20. The method of claim 19, wherein the pathogen is HIV, influenza, RSV, Rhinovirus, norovirus, HPV, Ebola, or Epstein-Barr virus.

21. The method of claim 18, wherein the pathogen is bacterial.

22. The method of claim 21, wherein the pathogen is MRSA or *Clostridium difficile*.

23. The method of claim 18, wherein the pathogen is the relevant causative pathogen of an infectious disease.

24. The method of claim 23, wherein the infectious disease is meningitis, hepatitis, malaria, tuberculosis, plague, polio, chlamydia, herpes, gonorrhoea, measles, mumps, rubella, cholera or smallpox.

25. The method according to claim 1, wherein both the first and second oligonucleotide probes are blocked at the 3' from extension by the DNA polymerase and are not capable of being cleaved by either the first or second restriction enzymes.

26. The method of claim 1, wherein the target nucleic acid is derived from a cancer.

27. The method of claim 26, wherein the cancer is colorectal cancer, lung cancer, breast cancer, pancreatic cancer, prostate cancer, liver cancer, bladder cancer, leukaemia, esophageal cancer, ovarian cancer, kidney cancer, stomach cancer or melanoma.

* * * * *